United States Patent
Lee et al.

(10) Patent No.: US 12,006,515 B2
(45) Date of Patent: Jun. 11, 2024

(54) COMPOSITION AND METHOD FOR PREVENTING OR TREATING EYE DISORDER

(71) Applicant: Buddhist Tzu Chi Medical Foundation, Hualien (TW)

(72) Inventors: Yuan-Chieh Lee, Hualien (TW); Li-Yi Sun, Hualien (TW)

(73) Assignee: Buddhist Tzu Chi Medical Foundation, Hualien (TW)

( * ) Notice: Subject to any disclaimer, the term of this patent is extended or adjusted under 35 U.S.C. 154(b) by 198 days.

(21) Appl. No.: 17/136,080

(22) Filed: Dec. 29, 2020

(65) Prior Publication Data

US 2021/0198631 A1    Jul. 1, 2021

Related U.S. Application Data

(60) Provisional application No. 62/954,738, filed on Dec. 30, 2019.

(51) Int. Cl.
| | |
|---|---|
| *C12N 5/0775* | (2010.01) |
| *A61P 27/02* | (2006.01) |
| *C12N 5/00* | (2006.01) |

(52) U.S. Cl.
CPC ............ *C12N 5/0668* (2013.01); *A61P 27/02* (2018.01); *C12N 5/0018* (2013.01); *C12N 2500/32* (2013.01); *C12N 2501/115* (2013.01); *C12N 2501/999* (2013.01)

(58) Field of Classification Search
CPC ................ C12N 5/0668; C12N 5/0018; C12N 2500/32; C12N 2501/115; C12N 2501/999; C12N 5/0621; C12N 5/0667; A61P 27/02; A61K 35/28
See application file for complete search history.

(56) References Cited

U.S. PATENT DOCUMENTS

| | | | | |
|---|---|---|---|---|
| 2014/0243227 | A1* | 8/2014 | Clevers | A61P 3/10 506/10 |
| 2016/0158293 | A1* | 6/2016 | Harris | C12N 5/062 424/93.7 |
| 2021/0046122 | A1* | 2/2021 | Nishida | A61P 1/02 |
| 2021/0284965 | A1* | 9/2021 | Germeroth | C12N 5/0657 |

OTHER PUBLICATIONS

By Pankajakshan et al. (Mesenchymal Stem Cell Paracrine Factors in Vascular Repair and Regeneration. J Biomed Technol Res, vol. 1, Aug. 2014) (Year: 2014).*
Beyazyildiz et al (Efficacy of Topical Mesenchymal Stem Cell Therapy in the Treatment of Experimental Dry Eye Syndrome Model. Stem Cells Int., Jun. 2014) (Year: 2014).*
The American Academy of Opthamology EyeWiki : eyewiki.aao.org/Corneal_Epithelial_Defect (Year: 2015).*
National Institutes of Advancing Translational Sciences: Rare disease Info: rarediseases.info.nih.gov/diseases/9732/epithelial-basement-membrane-corneal-dystrophy (Year: 2015).*
The definition and classification of dry eye disease: Report of the definition and classification subcommittee of the International Dry Eye WorkShop (2007), The Ocular Surface, vol. 5, No. 2, pp. 75-92, 2007 (Year: 2007).*
Thulasi et al (Update in Current Diagnostics and Therapeutics of Dry Eye Disease. American Academy of Ophthalmology, vol. 124, Nov. 2017) (Year: 2017).*
Villatoro et al (Regenerative Therapies in Dry Eye Disease: From Growth Factors to Cell Therapy. Int Journal of Mol Sci, vol. 18, Oct. 2017) (Year: 2017).*
Huang et al (Animal models of dry eye disease: Useful, varied and evolving (Review). Exp & Therapeutic Med, 2021) (Year: 2021).*
Pawitan et al (Prospect of Stem Cell Conditioned Medium in Regenerative Medicine. BioMed Research International, Aug. 2014) (Year: 2014).*
Sun et al (Expansion of Semi-Automatic Processed Human Adipose-Derived Stem Cells in Medium Supplemented with Autologous Serum and Antioxidants. Journal of Stem Cell Research & Therapy, vol. 4, 2014). (Year: 2014).*
Wang et al (Integrated Analyses of Mouse Stem Cell Transcriptomes Provide Clues for Stem Cell Maintenance and Transdifferentiation. Frontiers in Genetics, 2020) (Year: 2020).*
Nahar et al (A Comparison of Proteins Expressed between Human and Mouse Adipose-Derived Mesenchymal Stem Cells by a Proteome Analysis through Liquid Chromatography with Tandem Mass Spectrometry. Int. J. Mol. Sci. 2018, 19). (Year: 2018).*
Sagaradze et al (Conditioned Medium from Human Mesenchymal Stromal Cells: Towards the Clinical Translation. International Journal of Molecular Sciences, vol. 20, Apr. 2019) (Year: 2019).*
Temnov et al (The effect of a mesenchymal stem cell conditioned medium fraction on morphological characteristics of hepatocytes in acetaminophen-induced acute liver failure: a preliminary study. Hepatic Medicine: Evidence and Research, vol. 11, Jul. 2019). (Year: 2019).*

\* cited by examiner

*Primary Examiner* — Valarie E Bertoglio
*Assistant Examiner* — Matasha Dhar
(74) *Attorney, Agent, or Firm* — Amin, Turocy & Watson, LLP

(57) ABSTRACT

Provided is a method for preparing mesenchymal stem cell-conditioned medium, including isolating mesenchymal stem cells from a subject, maintaining the mesenchymal stem cells in a mesenchymal stem cell maintenance medium, collecting the mesenchymal stem cells at passages 2 to 5, culturing the mesenchymal stem cells in a medium supplemented with fetal bovine serum and mesenchymal stem cell culture adjuvant for hours to obtain a mesenchymal stem cell-conditioned medium, harvesting the medium and centrifuging followed by filtering. Also provided is a method for preventing or treating epithelial tissue disorder of eyes such as dry eye syndrome, including applying the medium to an eye of a subject. Further provided is a medical composition including the medium.

8 Claims, 63 Drawing Sheets

COMPOSITION AND METHOD FOR PREVENTING OR TREATING EYE DISORDER

BACKGROUND

1. Technical Field

The present disclosure relates to an adipose-derived stem cell-conditioned medium, and particularly to an adipose-derived stem cell-conditioned medium for preventing or treating eye disorder. The present disclosure also relates to a method for preparing the adipose-derived stem cell-conditioned medium.

2. Description of Associated Art

The prevalence of dry eye syndrome (DES) is increasing. Dry eyes cause ocular discomfort and impairs quality of vision (1). Current treatment strategy for the dry eye syndrome includes providing lubricants, anti-inflammatory drugs such as corticosteroids or cyclosporine, punctal occlusion, or even autoserum. Punctal occlusion decreases tear film loss, but increases inflammatory cytokines or enzymes in the tear film (2). Topical application of autologous serum drops provides lubrication and some biochemical components mimicking natural tears. However, the preparation and preservation of autoserum are inconvenient, and its effects on symptoms and signs of dry eyes are either inconsistent or lacking (3). Since conventional treatment modalities are not ideal in daily practice, further exploration is needed.

Stem cells are believed to have a fascinating role in degenerative disorders, and it has been reported that paracrine factors produced by stem cells may enhance tissue regeneration and healing processes (4-6). Their restoring capabilities in epithelial damage and anti-inflammatory effects have also been demonstrated (7, 8). Since corneal and conjunctival epithelial damage and inflammation are two important causes of dry eyes, the effects of stem cells and the paracrine factors on dry eyes deserve more investigation. While stem cells per se may possess tumorigenic or antigenic properties, it is an urgent problem to be solved in the relevant art to develop a medical composition for efficiently preventing or treating dry eyes.

SUMMARY

The present disclosure provides a method for treating epithelial tissue disorder of eyes in a subject in need thereof, comprising administering to said subject a therapeutically effective amount of a bioactive formulation comprising a composition prepared by: obtaining mesenchymal stem cells; culturing the mesenchymal stem cells in a medium; harvesting the medium; and obtaining a fraction less than 30 kDa from the medium harvested. In at least one embodiment, the medium is supplemented with serum and mesenchymal stem cell culture adjuvant (MCA). In some embodiments, the serum is fetal bovine serum or human serum having a concentration in a range of from 5% to 15% in the medium. In some embodiments, the medium is supplemented with about 10% serum and the mesenchymal stem cell culture adjuvant (MCA). In some embodiments, the serum (e.g., FBS) is supplemented in 5%, 6%, 7%, 8%, 9%, 10%, 11%, 12%, 13%, 14% or 15% for 36 hours, 48 hours, 60 hours, 72 hours, 84 hours, 96 hours, 108 hours, 120 hours or 132 hours.

In at least one embodiment, the mesenchymal stem cell culture adjuvant (MCA) comprises at least one of fibroblast growth factor 2 (FGF2), N-acetyl-L-cysteine (NAC) and L-ascorbic acid-2-phosphate (AsA2P). In some embodiments, the fibroblast growth factor 2 (FGF2) has a concentration in a range of from 5 ng/mL to 15 ng/mL in the mesenchymal stem cell culture adjuvant (MCA). In some embodiments, the FGF2 has a concentration of 5 ng/mL, 6 ng/mL, 7 ng/mL, 8 ng/mL, 9 ng/mL, 10 ng/mL, 11 ng/mL, 12 ng/mL, 13 ng/mL, 14 ng/mL or 15 ng/mL in the mesenchymal stem cell culture adjuvant (MCA).

In at least one embodiment, the N-acetyl-L-cysteine (NAC) has a concentration in a range of from 1 mM to 5 mM in the mesenchymal stem cell culture adjuvant (MCA). In some embodiments, the NAC has a concentration of 1 mM, 2 mM, 3 mM, 4 mM or 5 mM in the mesenchymal stem cell culture adjuvant (MCA).

In at least one embodiment, the L-ascorbic acid-2-phosphate (AsA2P) has a concentration in a range of from 0.1 mM to 0.5 mM in the mesenchymal stem cell culture adjuvant (MCA). In some embodiments, the AsA2P has a concentration of 0.1 mM, 0.2 mM, 0.3 mM, 0.4 mM or 0.5 mM in the mesenchymal stem cell culture adjuvant (MCA).

In some embodiments, the MCA comprises about 10 ng/mL fibroblast growth factor 2 (FGF2), about 2 mM N-acetyl-L-cysteine (NAC), and about 0.2 mM L-ascorbic acid-2-phosphate (AsA2P).

In at least one embodiment, the mesenchymal stem cells are cultured in the medium for at least 2 passages, e.g., two passages, three passages, four passages, or five passages.

In at least one embodiment, the mesenchymal stem cells are obtained from a subject. In some embodiments, the subject is a mammal. In some embodiments, the subject is human. In some embodiments, the mesenchymal stem cells are obtained from the adipose tissue of the subject.

In at least one embodiment, the present disclosure provides a composition comprising the <30 kDa (less than 30 kDa) fraction prepared by obtaining mesenchymal stem cells from a subject; culturing the mesenchymal stem cells in a medium; harvesting the medium; and obtaining the <30 kDa fraction from the harvested medium.

In at least one embodiment, a fraction less than 10 kDa (e.g., less than 8 kDa, less than 5 kDa, less than 3 kDa, less than 2 kDa or less than 1 kDa) is obtained from the harvested medium.

In at least one embodiment, the present disclosure also provides a use of the composition comprising the <30 kDa fraction for topical treatment of epithelial tissue disorder of eyes. In some embodiments, the epithelial tissue disorder of eyes is dry eye syndrome. In some embodiments, the dry eye syndrome is resulted from at least one of lack of tears, dry air or aging.

The present disclosure provides a method for treating dry eye syndrome in a subject in need thereof, comprising administering to said subject a therapeutically effective amount of a bioactive formulation that comprises a composition prepared by: obtaining adipose-derived stem cells (ADSCs); maintaining the ADSCs in a first medium; culturing the ADSCs in a second medium; harvesting the second medium; and obtaining <30 kDa fraction from the second medium.

In some embodiments, the present disclosure provides a method for preparing an adipose-derived stem cell-conditioned medium (ADSC-CM), comprising: isolating adipose-derived stem cells from a subject; maintaining the ADSCs in a mesenchymal stem cell maintenance medium; collecting the ADSCs at passages 2 to 5; culturing the ADSCs in a non-phenol red Iscove's Modified Dulbecco's Medium (IMDM) supplemented with 1 mM to 5 mM glutamine, 5% to 15% FBS and mesenchymal stem cell culture adjuvant (MCA) for 36 hours to 132 hours to obtain the adipose-derived stem cell-conditioned medium (ADSC-CM); harvesting the ADSC-CM; and centrifuging followed by filtering. In some embodiments, the glutamine is supplemented in 1 mM, 1.5 mM, 2 mM, 2.5 mM, 3 mM, 3.5 mM, 4 mM, 4.5 mM or 5 mM, and the FBS is supplemented in 5%, 6%, 7%, 8%, 9%, 10%, 11%, 12%, 13%, 14% or 15% for 36 hours, 48 hours, 60 hours, 72 hours, 84 hours, 96 hours, 108 hours, 120 hours or 132 hours.

In at least one embodiment of the present disclosure, the ADSC-CM comprises active ingredients having molecular weights less than 30 kDa, e.g., less than 20 kDa, less than 10 kDa, less than 8 kDa, less than 5 kDa, less than 3 kDa, less than 2 kDa and less than 1 kDa.

The present disclosure also provides an adipose-derived stem cell-conditioned medium (ADSC-CM) for preventing or treating dry eyes, wherein the ADSC-CM is obtained from the aforementioned method, and the ADSC-CM comprises active ingredients having molecular weights less than 30 kDa, e.g., less than 20 kDa, less than 10 kDa, less than 8 kDa, less than 5 kDa, less than 3 kDa, less than 2 kDa and less than 1 kDa.

In at least one embodiment of the present disclosure, the ADSC-CM comprises active ingredients having molecular weights less than 3 kDa.

The present disclosure also provides an adipose-derived stem cell-conditioned medium (ADSC-CM) for preventing or treating dry eyes, wherein the ADSC-CM is obtained from the aforementioned method, and the ADSC-CM comprises active ingredients having molecular weights less than 3 kDa.

In at least one embodiment of the present disclosure, the ADSC-CM comprises active ingredients having molecular weights less than 1 kDa.

The present disclosure also provides an adipose-derived stem cell-conditioned medium (ADSC-CM) for preventing or treating dry eyes, wherein the ADSC-CM is obtained from the aforementioned method, and the ADSC-CM comprises active ingredients having molecular weights less than 1 kDa.

The present disclosure also provides a method for preventing or treating dry eyes, comprising administering the ADSC-CM obtained from the aforementioned method to an eye of a subject in need thereof, wherein the ADSC-CM comprises active ingredients having molecular weights less than 30 kDa.

The present disclosure also provides a method for preventing or treating dry eyes, comprising administering the ADSC-CM obtained from the aforementioned method to an eye of a subject in need thereof, wherein the ADSC-CM comprises active ingredients having molecular weights less than 3 kDa.

The present disclosure also provides a method for preventing or treating dry eyes, comprising administering the ADSC-CM obtained from the aforementioned method to an eye of a subject in need thereof, wherein the ADSC-CM comprises active ingredients having molecular weights less than 1 kDa.

The present disclosure further provides a composition comprising the ADSC-CM obtained from the aforementioned method, wherein the ADSC-CM comprises active ingredients having molecular weights less than 30 kDa.

The present disclosure further provides a composition comprising the ADSC-CM obtained from the aforementioned method, wherein the ADSC-CM comprises active ingredients having molecular weights less than 3 kDa The present disclosure further provides a composition comprising the ADSC-CM obtained from the aforementioned method, wherein the ADSC-CM comprises active ingredients having molecular weights less than 1 kDa.

BRIEF DESCRIPTION OF THE DRAWINGS

The present disclosure can be more fully understood by reading the following descriptions of the embodiments, with reference made to the accompanying drawings, wherein:

FIG. 6A: non-dry control. FIGS. 6B to 6E: from mice in the CEC as dry control (FIG. 6B), and with topical application of R (FIG. 6C), IMMCA (FIG. 6D), and ADSC-CM (FIG. 6E). Magnification: 400×. Scale bars: 20 µm, 5 µm sections;

FIG. 8A: non-dry control; FIG. 8B: Dry control; FIG. 8C: R; FIG. 8D: IMMCA; FIG. 8E: ADSC-CM. Magnification: 40,000×. Scale bars: 500 nm;

FIG. 9A: non-dry control; FIG. 9B: Dry control; FIG. 9C: R; FIG. 9D: IMMCA; FIG. 9E: ADSC-CM. Magnification: 25,000×;

FIG. 17A: non-dry control. FIGS. 17B-17E: from mice in the CEC as dry control (FIG. 17B), and with ADSC-CM (FIG. 17C), ADSC-CM 30-100 kDa (FIG. 17D), and ADSC-CM 0-30 kDa (FIG. 17E). Magnification: 400×. Scale bars: 20 µm, 3 µm sections;

FIG. 18A: non-dry control. FIGS. 18B-18G: from mice in the CEC as Dry control (FIG. 18B), and with ADSC-CM (FIG. 18C), ADSC-CM>10 kDa (FIG. 18D), and ADSC-CM<10 kDa (FIG. 18E), ADSC-CM>3 kDa (FIG. 18F), and ADSC-CM<3 kDa (FIG. 18G). Magnification: 400×. Scale bars: 20 µm, 3 µm sections;

FIG. 19A: non-dry control. FIGS. 19B-19F: from mice in the CEC as dry control (FIG. 19B), and with ADSC-CM (FIG. 19C), ADSC-CM 0-3 kDa (FIG. 19D), ADSC-CM 0-1 kDa (FIG. 19E), and IMDM (FIG. 19F). Magnification: 400×. Scale bars: 50 µm, 3 µm sections;

FIG. 20A: non-dry control; FIG. 20B: dry control; FIG. 20C: ADSC-CM; FIG. 20D: ADSC-CM fraction having 30-100 kDa; FIG. 20E: ADSC-CM fraction having 0-30 kDa. Magnification: 400×. Scale bars: 20 µm, 3 µm sections. The data showed a higher conjunctival MUC16 expression in ADSC-CM and the ADSC-CM fraction 0-30 kDa treated conjunctiva in comparison to those with other eye drops and dry control. Arrow indicated the expression of MUC16 on the surface of conjunctival epithelium;

FIG. 21A: non-dry control; FIG. 21B: dry control; FIG. 21C: ADSC-CM; FIG. 21D: ADSC-CM fraction having >10 kDa; FIG. 21E: ADSC-CM fraction having <10 kDa; FIG. 21F: ADSC-CM fraction having >3 kDa; FIG. 21G: ADSC-CM fraction having <3 kDa. Magnification: 400×. Scale bars: 20 µm, 3 µm sections. The data showed a higher conjunctival MUC16 expression in ADSC-CM and the ADSC-CM fractions<10 kDa and <3 kDa treated conjunctiva in comparison to those with other eye drops and dry control. Arrow indicated the expression of MUC16 on the surface of conjunctival epithelium.

FIG. 22A: non-dry control; FIG. 22B: dry control; FIG. 22C: ADSC-CM; FIG. 22D: ADSC-CM fraction having 0-3 kDa; FIG. 22E: ADSC-CM fraction having 0-1 kDa; FIG. 22F: IMDM. Magnification: 200×. Scale bars: 50 µm, 3 µm sections. The data showed a higher conjunctival MUC16 expression in ADSC-CM and the ADSC-CM fractions having 0-3 kDa and 0-1 kDa treated conjunctiva in comparison to IMDM and dry control;

FIG. 25A: non-dry control; FIG. 25B: dry control; FIG. 25C: ADSC-CM; FIG. 25D: ADSC-CM fraction having 30-100 kDa; FIG. 25E: ADSC-CM fraction having 0-30 kDa. Magnification: 25,000×;

FIG. 26A: non-dry control, FIG. 26B: dry control; FIG. 26C: ADSC-CM; FIG. 26D: ADSC-CM fraction having >10 kDa; FIG. 21E: ADSC-CM fraction having <10 kDa; FIG. 26F: ADSC-CM fraction having >3 kDa; FIG. 26G: ADSC-CM fraction having <3 kDa. Magnification: 25,000×; FIG. 27A: non-dry control; FIG. 27B: dry control; FIG. 27C: ADSC-CM; FIG. 27D: ADSC-CM fraction having 0-3 kDa; FIG. 27E: ADSC-CM fraction having 0-1 kDa; FIG. 27F: IMDM. Magnification: 250,00×.

DETAILED DESCRIPTION OF THE EMBODIMENTS

Figure 1:
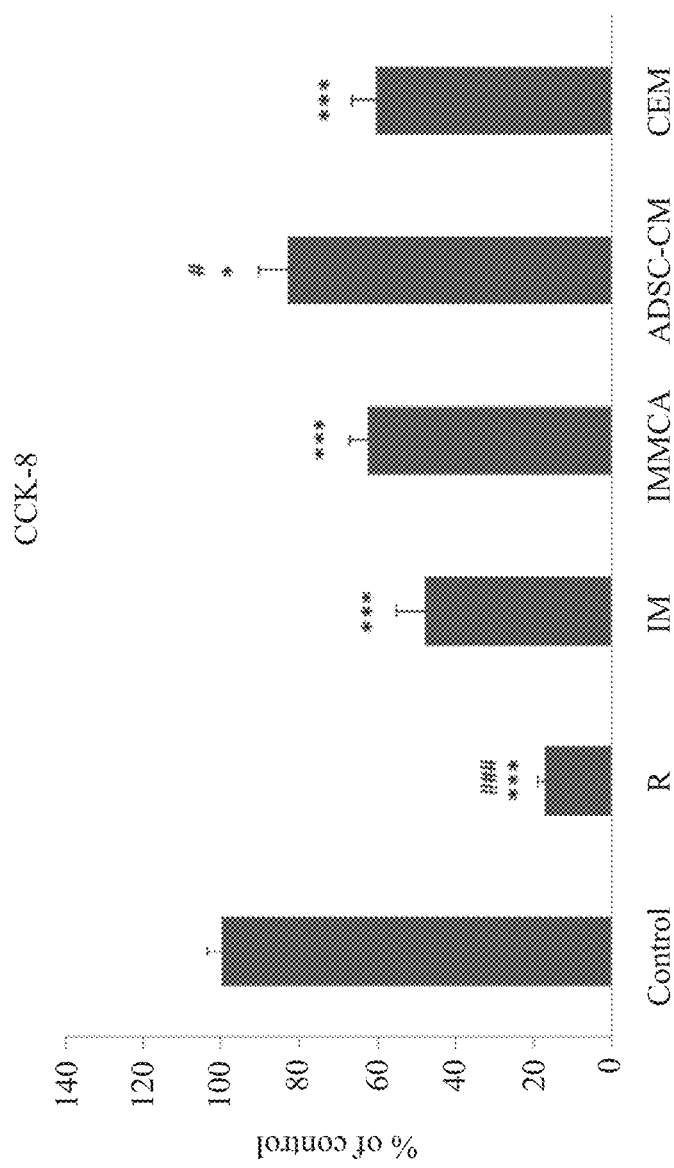
FIG. 1 shows the effect of different medium preparations on viability of human corneal epithelial cells (HCECs) estimated by Cell Counting Kit-8 (CCK-8 assay) in a desiccation stress study. HCECs were grown to approximately 80% confluence, and then left air dry for 10 min. After desiccation, the cells were then transferred into different culture media. After incubation for 2 hours, the cells were counted using the CCK-8 assay. Control represents HCECs without air dry treatment. R represents Refresh Plus Lubricant eye drops. IM represents IMDM supplemented with 10% fetal bovine serum and glutamine. IMMCA represents IM supplemented with 10 ng/mL fibroblast growth factor-2 (FGF-2), 2 mM N-acetyl-L-cysteine and 0.2 mM L-ascorbic acid-2-phosphate. ADSC-CM represents IMMCA conditioned by cultures of adipose-derived mesenchymal stem cells. CEM represents a corneal epithelial cell basal medium supplemented with corneal epithelial cell growth kit components. The values were presented as the means±SEM of three replicates. *P<0.05, P<0.01, *P<0.001 compared with the Control. *P<0.05, *P<0.001 compared with the CEM.

The following examples are used to exemplify the present disclosure. A person of ordinary skill in the art can conceive the other aspects of the present disclosure, based on the specification of the present disclosure. The present disclosure can also be implemented or applied as described in different examples. It is possible to modify and/or alter the examples for carrying out this disclosure without contravening its scope, for different aspects and applications.

It is further noted that, as used in this specification, the singular forms "a," "an," and "the" include plural referents unless expressly and unequivocally limited to one referent. The term "or" is used interchangeably with the term "and/or" unless the context clearly indicates otherwise.

The present disclosure provides a method for treating dry eye syndrome in a subject in need thereof, comprising administering to said subject a therapeutically effective amount of a bioactive formulation that comprises a composition prepared by: obtaining adipose-derived stem cells (ADSCs); maintaining the ADSCs in a first medium; culturing the ADSCs in a second medium; harvesting the second medium; obtaining a fraction less than 30 kDa from the second medium harvested.

For maintaining and culturing of the ADSCs, different types of media may be used and chosen by one of ordinary skill in the art. In at least one embodiment, the medium is selected from the group consisting of alpha minimum essential medium (MEM), Dulbecco's Modified Eagle's Medium (DMEM), Roswell Park Memorial Institute (RPMI) medium, Opti-MEM, improved minimum essential medium (IMEM), Iscove's Modified Dulbecco's Medium (IMDM) and AIM-V medium. Cells may be cultured in a variety of media for expansion that contain fetal calf serum, or other growth factors. In at least one embodiment, the cells are transferred to a medium substantially lacking serum, and preparation of the conditioned medium before administration may be performed by various means; for example, the conditioned medium may be filter sterilized, or concentrated in some conditions. In some embodiments, the conditioned medium undergoes further preparation steps to obtain different fractions containing different molecules with size in a range of greater than 100 kDa, greater than 30 kDa, greater than 3 kDa, greater than 1 kDa, less than 100 kDa, less than 50 kDa, less than 40 kDa, less than 30 kDa, less than 20 kDa, less than 10 kDa, less than 5 kDa, less than 3 kDa, less than 1 kDa, between more than 0 kDa and 100 kDa, between more than 0 kDa and 30 kDa, between more than 0 kDa and 3 kDa, or between more than 0 kDa and 1 kDa.

In some embodiments, the conditioned medium is used as an active ingredient for manufacture of a pharmaceutical formulation. In at least one embodiment, the stem cell conditioned medium may be administered as a therapeutic agent alone. In some embodiments, the administration may involve a way of known pharmaceutical formulations, including tablets, capsules or elixirs for oral administration, suppositories for rectal administration, sterile solutions or suspensions for parenteral or intramuscular administration, liposomal or encapsulated formulations, formulations of which the therapeutic agent is alone or conjugated to a delivery agent or vehicle, and the like. It will be appreciated that therapeutic entities of the disclosure will be administered with suitable carriers, excipients, and/or other agents that are incorporated into formulations to provide improved transfer, delivery, tolerance, and the like. A multitude of appropriate formulations can be found in the formulary known to all pharmaceutical chemists. These formulations include, for example, powders, pastes, ointments, jellies, waxes, oils, lipids, lipid (cationic or anionic) containing vesicles (such as Lipofectin), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present disclosure, provided that the active ingredient in the formulation is not inactivated by the formulation and the formulation is physiologically compatible and tolerable with the route of administration.

In some embodiments, the composition prepared by the present disclosure is administered by topical formulations. Topical formulations are useful in the treatment of conditions associated with dermal diseases. For example, topical forms of administration may consist of, for example, aqueous and nonaqueous gels, creams, multiple emulsions, microemulsions, liposomes, ointments, aqueous and non-aqueous solutions, lotions, aerosols, skin patches, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In at least one embodiment, the pharmaceutically acceptable carrier is a liposome or a transdermal enhancer. Topical formulations of the present disclosure may include a dermatologically acceptable carrier, e.g., a substance that is capable of delivering the other components of the formulation to the skin with acceptable application or absorption of those components by the skin. The carrier will typically include a solvent to dissolve or disperse the therapeutic agent, and optionally one or more excipients or other vehicle ingredients. Carriers useful in accordance with the topical formulations of the present disclosure may include, by way of non-limiting example, water, acetone, ethanol, ethylene glycol, propylene glycol, butane-1,3-diol, acrylates copolymers, isopropyl myristate, isopropyl palmitate, mineral oil, butter(s), aloe, talc, botanical oils, botanical juices, botanical extracts, botanical powders, other botanical derivatives, lanolin, urea, petroleum preparations, tar preparations, plant or animal fats, plant or animal oils, soaps, triglycerides, and keratin(s). Topical formulations of the present disclosure are prepared by mixing the composition of the disclosure with a topical carrier according to well-known methods in the art, for example, methods provided by standard reference texts, e.g., Remington: The Science and Practice of Pharmacy, 1577-1591, 1672-1673, 866-885 (Alfonso R. Gennaro ed. 19th ed. 1995) and Ghosh et al., Transdermal and Topical Drug Delivery Systems (1997). In some embodiments, moisturizers or humectants, sunscreens, fragrances, dyes, and/or thickening agents such as paraffin, jojoba, PABA and waxes, surfactants, occlusives, hygroscopic agents, emulsifiers, emollients, lipid-free cleansers, antioxidants and lipophilic agents, may be added to the topical formulations of the present disclosure if desired. A topical formulation of the disclosure may be designed to be left on the skin and not washed shortly after application. Alternatively, the topical formulation may be designed to be rinsed off within a given amount of time after application.

The present disclosure provides a method for preparing an adipose-derived stem cell-conditioned medium (ADSC-CM), comprising: isolating adipose-derived stem cells from a subject; maintaining the ADSCs in a mesenchymal stem cell maintenance medium; collecting the ADSCs at passages 2 to 5; culturing the ADSCs in a non-phenol red Iscove's Modified Dulbecco's Medium (IMDM) supplemented with 1 mM to 5 mM glutamine, 5% to 15% fetal bovine serum (FBS) and mesenchymal stem cell culture adjuvant (MCA) for 36 hours to 132 hours to obtain an adipose-derived stem cell-conditioned medium (ADSC-CM), wherein the MCA comprises 5 ng/mL to 15 ng/mL fibroblast growth factor 2 (FGF-2), 1 mM to 5 mM N-acetyl-L-cysteine (NAC), and 0.1 mM to 0.5 mM L-ascorbic acid-2-phosphate (AsA2P); harvesting the ADSC-CM; and centrifuging followed by filtering.

In at least one embodiment of the present disclosure, the IMDM is supplemented with 2 mM glutamine, 10% FBS and MCA for 72 hours.

In at least one embodiment of the present disclosure, the MCA comprises 5 ng/mL to 15 ng/mL fibroblast growth factor 2 (FGF2), 1 mM to 5 mM N-acetyl-L-cysteine (NAC) and 0.1 mM to 0.5 mM L-ascorbic acid-2-phosphate (AsA2P). In some embodiments of the present disclosure, the MCA comprises about 10 ng/mL FGF2, about 2 mM N-acetyl-L-cysteine and about 0.2 mM L-ascorbic acid-2-phosphate (AsA2P).

In at least one embodiment of the present disclosure, the method further comprises a step of freezing after filtering.

In at least one embodiment of the present disclosure, the subject is a mammal. In some embodiments, the subject is human, rats, mice, porcine, rabbits, sheep, goats, cats, dogs, calf or papion.

In at least one embodiment of the present disclosure, the ADSC-CM comprises active ingredients having molecular weights of less than 30 kDa.

In some embodiments of the present disclosure, the ADSC-CM comprises active ingredients having molecular weights of less than 3 kDa.

In some embodiments of the present disclosure, the ADSC-CM comprises active ingredients having molecular weights of less than 1 kDa.

The present disclosure also provides an adipose-derived stem cell-conditioned medium (ADSC-CM) for preventing or treating dry eyes. In at least one embodiment of the present disclosure, the ADSC-CM comprises active ingredients having molecular weights of less than 30 kDa. In some embodiments of the present disclosure, the ADSC-CM comprises active ingredients having molecular weights of less than 3 kDa. In some embodiments of the present disclosure, the ADSC-CM comprises active ingredients having molecular weights of less than 1 kDa.

As used herein, the term "dry eye" refers to a disorder of the tear film due to tear deficiency or excessive evaporation, which causes damage to the interpalpebral ocular surface and is associated with symptoms of ocular discomfort (37).

The present disclosure also provides a method for preventing or treating dry eyes, comprising applying the ADSC-CM obtained from the aforementioned method to an eye of a subject. In at least one embodiment, the ADSC-CM comprises active ingredients having molecular weights of less than 30 kDa. In some embodiments of the present disclosure, the ADSC-CM comprises active ingredients having molecular weights of less than 3 kDa. In some embodiments of the present disclosure, the ADSC-CM comprises active ingredients having molecular weights of less than 1 kDa. The present disclosure further provides a medical composition, comprising the ADSC-CM obtained from the aforementioned method. In at least one embodiment, the ADSC-CM comprises active ingredients having molecular weights of less than 30 kDa. In some embodiments of the present disclosure, the ADSC-CM comprises active ingredients having molecular weights of less than 3 kDa. In some embodiments of the present disclosure, the ADSC-CM comprises active ingredients having molecular weights of less than 1 kDa.

The following are embodiments further demonstrating the efficacy of the present disclosure, but not to limit the scope of the present disclosure.

EXAMPLES

Preparation Example 1: Isolation and Maintenance of ADSC-CM

This study was approved by the Buddhist Tzu Chi General Hospital Internal Review Board (IRB102-130), and informed consent was obtained from all study subjects. Human adipose tissues were harvested during cosmetic liposuction from abdominal subcutaneous fat of three women at ages of 23, 28, and 30, respectively. Stromal-vascular fraction cells were isolated using a method similar to that provided by Griesche and colleagues (9). Collagenase type I (Sigma) with a final concentration of 0.4 mg/mL was added for enzymatic digestion in a hybridization oven, which was performed at conditions of 37° C., 30° angle and 15 rpm for 45 min. Digested adipose tissues were centrifuged at 400×g for 10 min to generate the stromal vascular fraction (SVF) pellets for subsequent ADSCs culture. To maintain and expand ADSCs populations, the cells were cultured in a mesenchymal stem cell maintenance medium containing Iscove's modified Dulbecco's medium (IMDM, Gibco) and 10% fetal bovine serum (FBS, Gibco) with 10 ng/mL FGF-2 (R&D Systems) as previously described (10, 11). Experiments were conducted using ADSCs at passages 2 to 5 (P2 to P5).

Preparation Example 2: Preparation of ADSC-CM

ADSCs were seeded in 150 cm$^2$ tissue culture flasks (BD Falcon, 355001, Durham, N.C.) at 1×10$^6$ cells per flask and cultured with non-phenol red Iscove's Modified Dulbecco's Medium (IMDM) (Gibco) supplemented with 2 mM glutamine (Gibco), 10% FBS (HyClone) and mesenchymal stem cell culture adjuvant (MCA) comprising 10 ng/mL fibroblast growth factor 2 (FGF2, R&D Systems), 2 mM N-acetyl-L-cysteine (NAC, Sigma) and 0.2 mM L-ascorbic acid-2-phosphate (AsA2P, Sigma). ADSC-conditioned medium (ADSC-CM) was collected after 72 hours of culture, centrifuged at 300×g for 5 min, and filtered through a 0.22 μm syringe filter. ADSC-CM from P2 to P5 ADSCs were collected and mixed, and then aliquoted and frozen for further use.

Preparation Example 3: ADSC-CM in Different Size Fractions

Different size fractions of ADSC-CM were prepared using Millipore Amicon Ultra-15 centrifugal tube or Spectrum Labs hollow fiber filter. Specifically, fractions containing protein (as assessed by SDS-PAGE) were pooled and concentrated using an Amicon centrifugal concentrator (molecular weight cut-off (MWCO)=30 kDa, 3 kDa, or 1 kDa) to a final concentration of 1 mg/mL while the flow through was collected and concentrated to a final concentration of 1.5 mg/mL. The sample was flash frozen and stored at −20° C. until required.

The concentrated conditioned medium was diluted with IMDM adding to the cells for quantitation of viable cell number by Cell Counting Kit-8.

For lyophilized conditioned medium test, aliquots of the dialyzed samples (1 mL) were prepared in 5 mL lyophilized vials followed by lyophilization in a programmable freeze dryer.

For heat stable test, conditioned medium was incubated at either 56° C. for 30 minutes or 100° C. for 3 minutes.

For lipid extraction, conditioned medium was treated by hexane of 1:1 ratio for 3 times, and the lower layer aqueous phase was collected.

For electrically charged test, the conditioned medium was first dialyzed to 20 mM Tris (pH 8.0). After dialysis, the sample was applied to an SP-Sepharose cation exchange column. The column was eluted with 20 mM Tris, 1 M NaCl (pH 8.0) over 6 column volumes.

Example 1: In Vitro Human Corneal Epithelial Cells (HCECs) Desiccation Stress Study with ADSC-CM Normal primary HCECs from American Type Culture Collection (ATCC, Manassas, Va., USA) were maintained according to the instructions. The HCECs were grown in a corneal epithelial cell basal medium supplemented with corneal epithelial cell growth kit components (CEM, ATCC). The cells were cultured at 37° C. in a moist atmosphere with 5% carbon dioxide. The culture medium was changed every 2 or 3 days. In this embodiment, only sub-confluent HCECs at passage 4 were used.

A modified in vitro desiccation stress on HCECs was used (12-14). Briefly, HCECs were grown to approximately 80% confluence. The medium was aspirated, and the dishes were left dry for 10 min at 37° C. After the desiccation stress, the cells were then transferred into different culture media, comprising CEM (Refresh Plus Lubricant eye drops, abbreviated as R; Allergan, Westport, Ireland), IMDM supplemented with 10% fetal bovine serum and glutamine (abbreviated as IM), IMDM supplemented with 10% FBS, glutamine and MCA (abbreviated as IMMCA, used as a control medium that has not been conditioned by ADSCs), and ADSC-CM. After incubation for 2 hours, the cells were counted using the Cell Counting Kit-8 (CCK-8 assay, Enzo Life Sciences, Farmingdale, NY, USA) or lysed in a radio-immunoprecipitation assay (RIPA) buffer for western blot analysis.

For the cell viability assay, 10 μL CCK-8 reagent was added to cells that were grown on the 96-well culture plate containing 100 μL of the different culture media as described above. Cells were incubated at 37° C. for 3 hours. The absorbance at 450 nm was measured using a microplate reader (MicroQuant, BioTek Instruments, Inc., Winooski, VT, USA). Results were plotted as means±standard error of the mean of three replicates. As shown in FIG. 1, the results of in vitro HCECs desiccation stress showed that desiccation for 10 minutes caused significantly decreased cell viability or proliferation. However, the decline could be reversed, and ADSC-CM is shown to have the best protective effects against desiccating stress on the HCECs.

For the western blotting analysis, the cells were washed twice with ice-cold phosphate buffered saline (PBS) and lysed with RIPA buffer (Millipore, Billerica, MA, USA) containing Halt protease and phosphatase inhibitor cocktail (Pierce, Thermo Fisher Scientific, Rockford, IL, USA) for 20 minutes on ice. The cell extracts were centrifuged at 13,200 rpm for 10 minutes at 4° C., and the supernatants were collected for experiments. The protein concentrations of the cell extracts were determined by Bradford's method using the Bradford Method Protein Assay Kit (Amresco, Ohio, USA) with known concentrations of bovine serum albumin as standards.

The 50 μg protein samples were separated on 10% SDS-polyacrylamide gels, followed by electrophoresis and blotting onto polyvinylidene difluoride (PVDF) membranes (Sigma). The membranes were blocked with 5% nonfat milk in PBS containing 0.1% Tween-20 (PBS-T) for 1 hour at room temperature and then incubated overnight at 4° C. with appropriate primary antibodies of rabbit monoclonal anti-Erk1/2 (extracellular signal-regulated kinase 1/2) antibody, rabbit monoclonal anti-phospho-Erk1/2 (Thr202/Tyr204) antibody, rabbit monoclonal anti-P38 mitogen-activated protein kinase (MAPK) antibody, rabbit monoclonal anti-phospho-P38 MAPK (Thr180/Tyr182) antibody, rabbit monoclonal anti-SAPK/JNK (stress-activated protein kinase/c-Jun NH$_2$-terminal kinase) antibody, rabbit monoclonal anti-phospho-SAPK/JNK (Thr183/Tyr185) antibody (Cell Signaling Technology, Beverly, MA, USA) diluted with Seppro stripping buffer (Sigma) by 1:1000, or rabbit monoclonal anti-GAPDH (glyceraldehyde-3-phosphate dehydrogenase) antibody (Cell Signaling Technology) diluted by 1:5000. After washing with PBS-T, the membranes were incubated with horseradish peroxidase (HRP)-conjugated goat anti-rabbit IgG antibody (GeneTex, Irvine, CA, USA) for 1 hour at room temperature. Signals were developed using the VisGlow Chemiluminescent Substrate, Horseradish Peroxidase System (Visual Protein, Taipei, Taiwan). Images were acquired with a Wealtec KETA imaging system.

Figure 2:
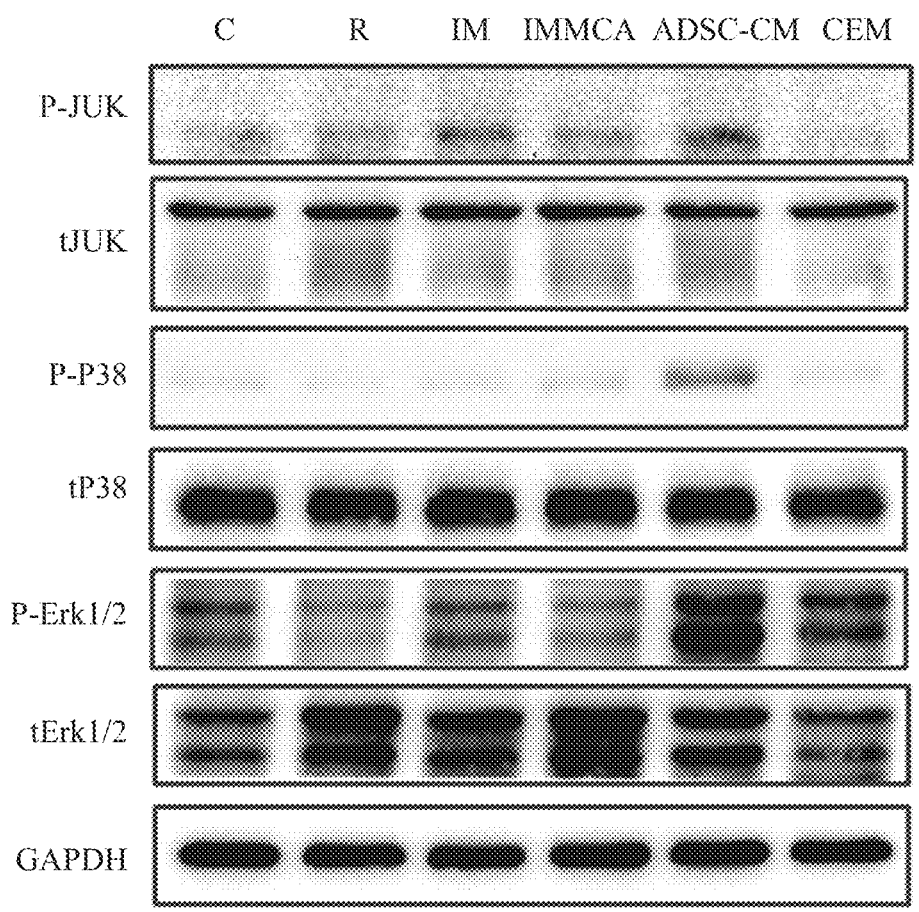
FIG. 2 shows western blot analysis of the expressions of JUK, P38 and Erk1/2 genes in HCECs from the desiccation stress study, where P stands for "phosphorylated," and t stands for "total"

Results shown in FIG. 2 revealed that ADSC-CM increased the expression of phosphorylated-JUK (P-JUK), phosphorylated P38 (P-P38) and phosphorylated Erk1/2 (P-Erk1/2) in HCECs.

Example 2: In Vivo Animal Study of Dry Eyes with ADSC-CM

1. Establishment of a Murine Dry Eye Model:

All experimental procedures were approved by the Laboratory Animal Care and Use Committee at Tzu Chi University. Dry eye-related ocular surface signs of BALB/c mice were induced in a controlled-environment chamber (CEC) as previously described (15). Briefly, 13-week-old female BALB/c mice were exposed to a CEC in which relative humidity of 10±3%, temperature of 21-25° C., and an air flow of 10-15 L/min were monitored and maintained. The mice were separated into five groups. Each experimental and control group consisted of 5 mice. Four groups were kept in the CECs as dry eye groups, and one group was kept in a chamber of humidity of 75±3% as the normal non-dry control. Among those four CEC-dry eye groups, one group as the dry eye control group did not receive any eye drops, while the other three groups respectively received the following eye drops of R, IMMCA (used as a control medium that has not been conditioned by ADSCs) and ADSC-CM culture media twice a day for 28 days. One drop of about 50 µL was given each time. Tear secretion assay was performed weekly.

At the end of the experiments (i.e., at the end of the $28^{th}$ day), the ocular surface was evaluated by fluorescein staining and rose bengal staining, and corneal thickness was estimated by optical coherence tomography. The mice were then sacrificed, and the eyeballs were preserved for immunohistochemical study and electric microscopic examination.

Moreover, the statistical analysis of data was expressed as means±standard error of the mean. One-way analysis of variance (ANOVA) and two-sample t test were used to compare CCK-8 assay, fluorescein and rose bengal staining, and conjunctival goblet cell density. $p<0.05$ was considered statistically significant.

2. Tear Secretion Assay

Tear secretion was estimated by the length of the tear-absorbed, color-changed region on Zone-Quick phenol red thread (Showa Yakuhin Kako Co., Ltd., Japan). Briefly, the excess tears were removed for a standard time of 4 seconds, and the Zone-Quick phenol red threads were then held with jeweler forceps and placed in the lateral fornix for 30 seconds. The left eyes were measured first and then the right eyes. The average of both eyes is calculated for analysis. In this embodiment, each experimental and control group consisted of 10 eyes (n=5 mice/group).

Figure 3:
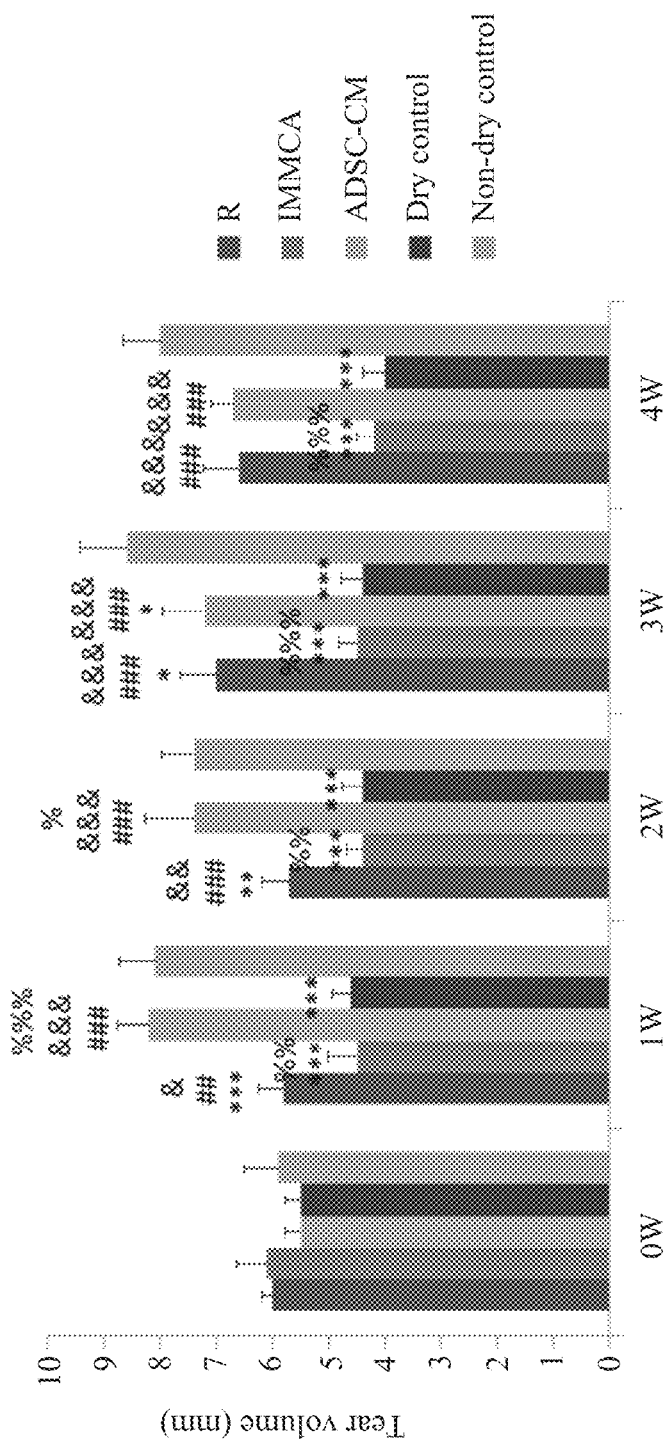
FIG. 3 shows the tear volume of BALB/c mice housed in controlled-environment chambers (CEC) treated with different eye drops. Tear volume is measured with phenol thread in millimeter. Mean tear volumes in each group of non-dry control, dry control, refresh, IMMCA, and ADSC-CM were shown. * denotes comparison with non-dry control, *p<0.05, p<0.01, *p<0.001. #denotes comparison with Dry control, #p<0.05, ##p<0.01, ###p<0.001. & denotes comparison with IMMCA, & p<0.05, && p<0.01, &&& p<0.001. % denotes comparison with Refresh, % p<0.05, %% p<0.01, %%% p<0.001. Mean±SEM, N=4. 0.2% benzalkonium chloride (BAK) were administered once daily in each eye.

As shown in FIG. 3, there was a significant difference of the tear volume secreted by mice in the ADSC-CM, comparing to the other groups in tear secretion assay. In the first and second week of treatment, mice in the ADSC-CM group have the tear volume comparable to that in the non-dry control, indicating that ADSC-CM is able to maintain the level of the tear volume as the non-dry control. In the third and fourth week, the tear volume secreted in the mice in the ADSC-CM group still has the tear volume that is significantly higher than that in the dry control and mice treated with IMMCA.

3. Fluorescein Staining and Rose Bengal Staining Assays

After applying a 1-µL drop of 1% fluorescein into the conjunctival sac for 90 seconds, the corneas were evaluated independently using the following fluorescein staining scoring system: 0=no staining; 1=slightly punctate staining (<30 spots); 2=punctate staining (>30 spots), but not diffuse; 3=severe diffuse staining, but no positive plaque; and 4=positive fluorescein plaque (16).

After instilling a 1-µL drop of 1% rose bengal into the conjunctival sac for 15 seconds, the rose bengal staining of the corneas was scored using the Van Bijsterveld system as follows: 1=few separated spots; 2=many separated spots; and 3=confluent spots (the maximum score is 9 points) (17).

Figure 4:
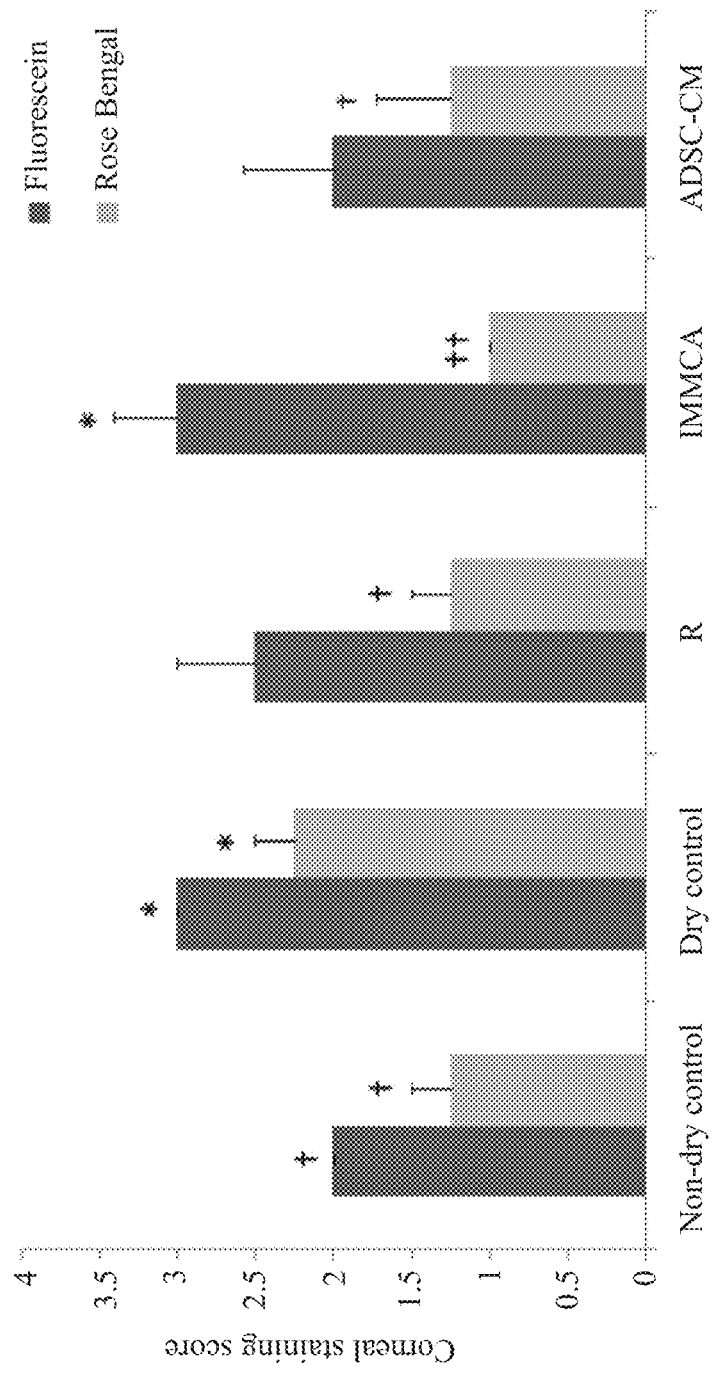
FIG. 4 shows fluorescein staining and rose bengal staining of BALB/c mice. The corneal staining was increased in the mice from CEC. Topical application of R, IMMCA or ADSC-CM reversed the rose bengal staining. Fluorescein staining scoring was as follows: 0=no staining; 1=slightly punctate staining (<30 spots); 2=punctate staining (>30 spots), but not diffuse; 3=severe diffuse staining, but no positive plaque; and 4=positive fluorescein plaque. The rose bengal staining of the corneas was scored as follows: 1=few separated spots; 2=many separated spots; and 3=confluent spots (the maximum score is 9 points). *p<0.05 compared with the non-dry control group. †p<0.05 compared with the dry control group. ††p<0.01 compared with the dry control group. N=5.

As shown in FIG. 4, results showed that the dry control group had the highest scores of staining, which was alleviated by application of R, IMMCA, or ADSC-CM. It is noted that the staining in the ADSC-CM group was alleviated the most and reverted to a level similar to the non-dry control group.

4. Immunofluorescence Double Staining

The eyes were fixed in 10% formaldehyde. After paraffin embedding, 3-µm-thick sections were dewaxed in xylene, rehydrated in a series of ethanol solutions, and washed twice in distilled water. Antigen retrieval was performed with DAKO Target Retrieval Solution, pH=9 (DAKO, Glostrup, Denmark) for 15 min at 90-95° C. Sections were blocked with 1% BSA in PBS with 0.3% Triton X-100 for at least 1 hour at room temperature. The slides were incubated with the rabbit anti-ZO-1 (Mid) (1:100; Invitrogen, Camarillo, CA, USA), mouse anti-Occludin (1:50; Thermo Scientific, Rockford, IL, USA) or goat anti-Cytokeratin 12 (1:50; Santa Cruz, Santa Cruz, CA, USA) overnight at 4° C., followed by Alexa Fluor 488 donkey anti-rabbit IgG (H+L) (1:800; Jackson ImmunoResearch, West Grove, PA, USA), Dylight 550-conjugated goat anti-mouse IgG (H+L) or Dylight 550-conjugated donkey anti-goat IgG (H+L) (1:500 Bethyl, Monthomery, TX, USA) for 1 hr at room temperature. The nucleus is counterstained with 4',6-diamidino-2-phenylindole (DAPI; Molecular Probes, Eugene, OR, USA). The slides were mounted and examined with a Zeiss LSM 510 META confocal microscope. In negative controls, the primary antibody was substituted with the blocking buffer.

Figure 5A:
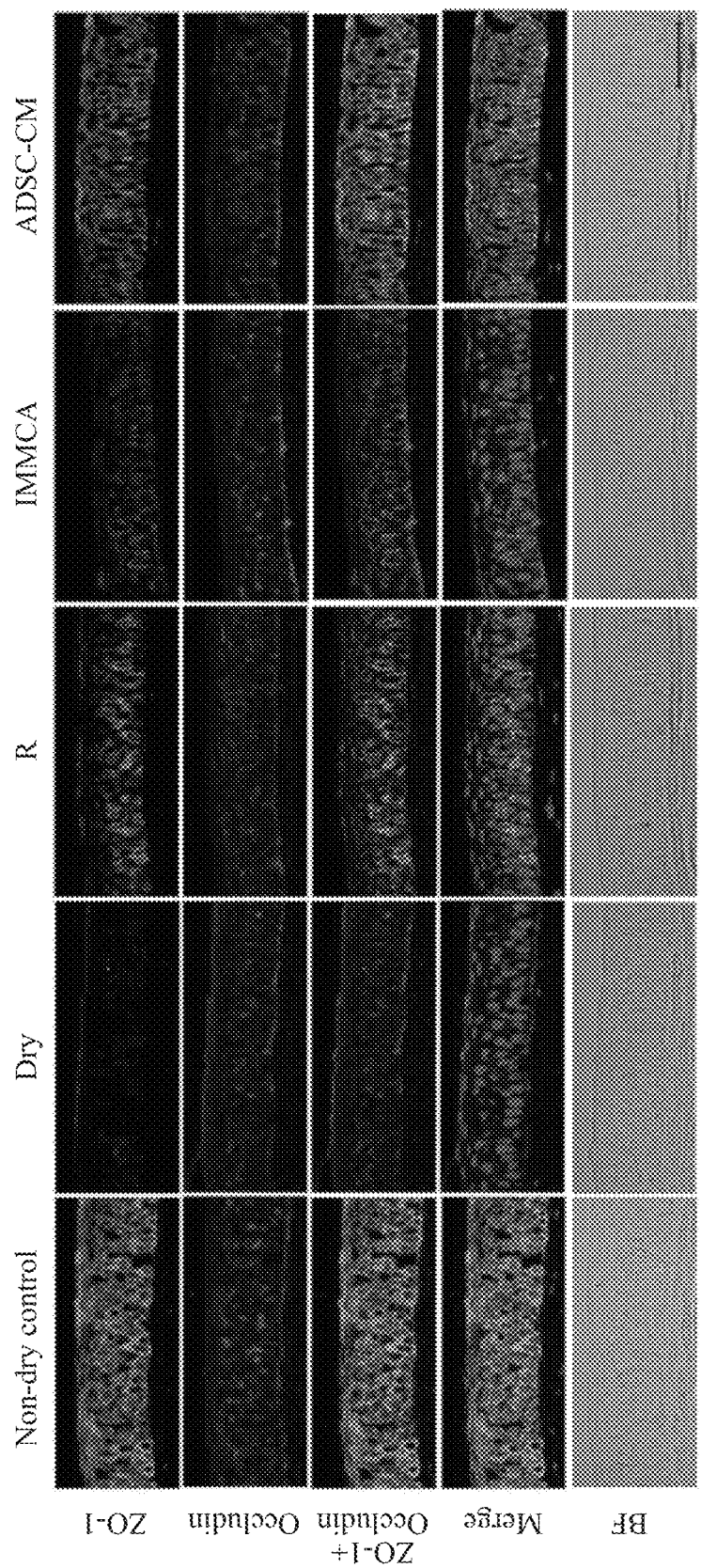
FIGS. 5A and 5B show the confocal microscopic examination of corneal epithelium and the integrity of tight junction barriers of corneal epithelium of BALB/c mice in the CEC-induced dry eye model. BF: Bright Field.
Figure 5B:
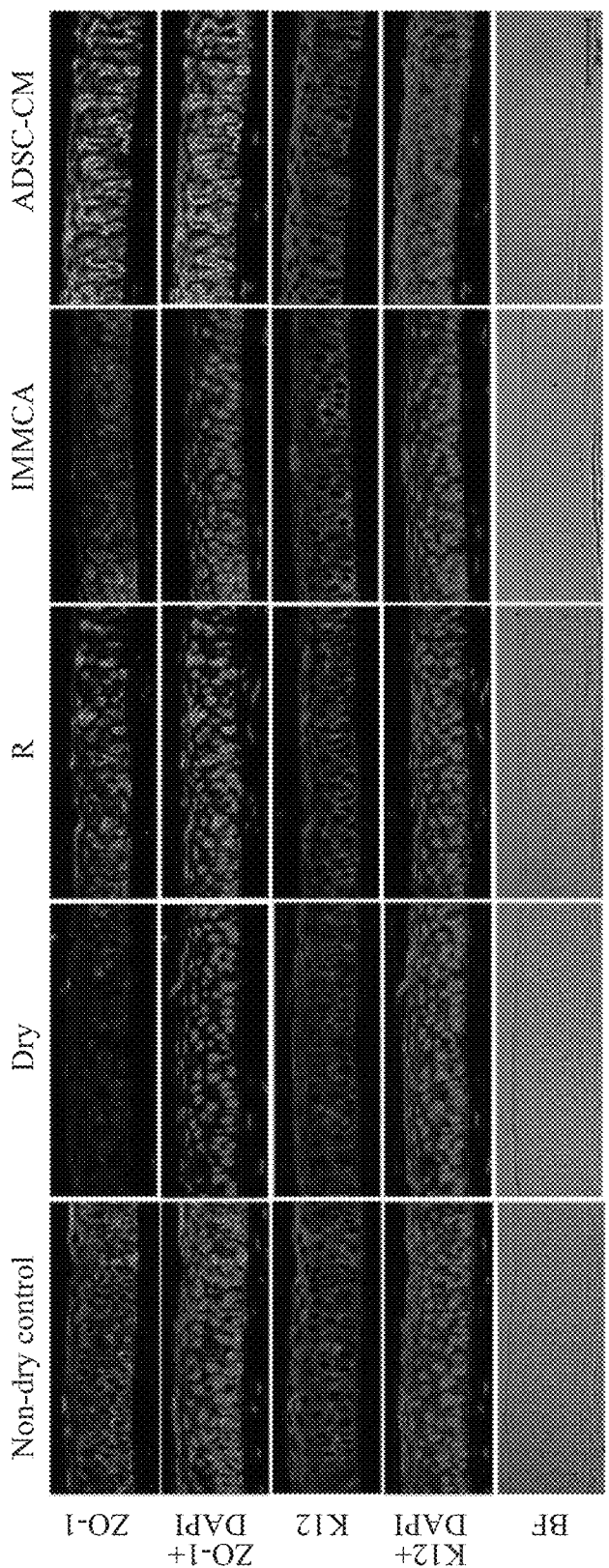

Results were shown in FIGS. 5A and 5B. FIG. 5A showed that zonula occludens-1 (ZO-1) and occludin expressions were suppressed in the BALB/c mice in CEC. Although topical application of R or IMMCA alleviated the suppressed expression, ADSC-CM showed the best rescue. In another experiment, FIG. 5B showed that ZO-1 and keratin 12 (K12) expressions were also suppressed in the BALB/c mice in CEC. Mice received topical application of ADSC-CM showed the best expression. Therefore, the results revealed a decreased expression of ZO-1, occludin, and K12 in the CEC-induced dry eyes. The decrease was partially reversed by R and IMMCA, but the best expression was noted in the ADSC-CM group.

5. Histological Analysis and Immunohistochemistry (IHC) Assay

For the histological assay, the eyes were fixed in 10% formaldehyde and embedded in paraffin. Central vertical plane sections of 3 µm thickness were stained with hematoxylin-eosin or periodic acid-Schiff (PAS). Corneal epithelial morphology and the thickness of epithelium and stromal at the central cornea were estimated, and the mean conjunctival goblet cell densities were calculated by the ImageJ assay.

Figure 6A:
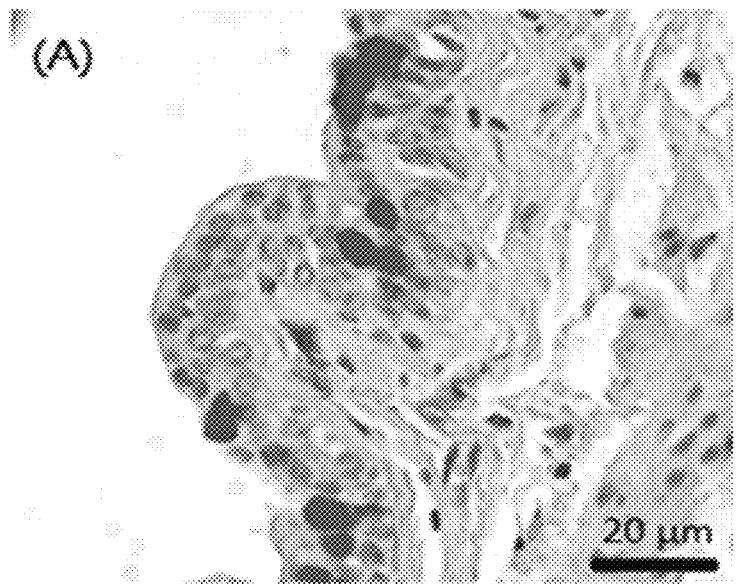
FIGS. 6A to 6E show the results of periodic acid-Schiff (PAS) staining of the conjunctival goblet cells in different groups of controlled-environment chamber (CEC)-induced dry eyes.
Figure 6B:
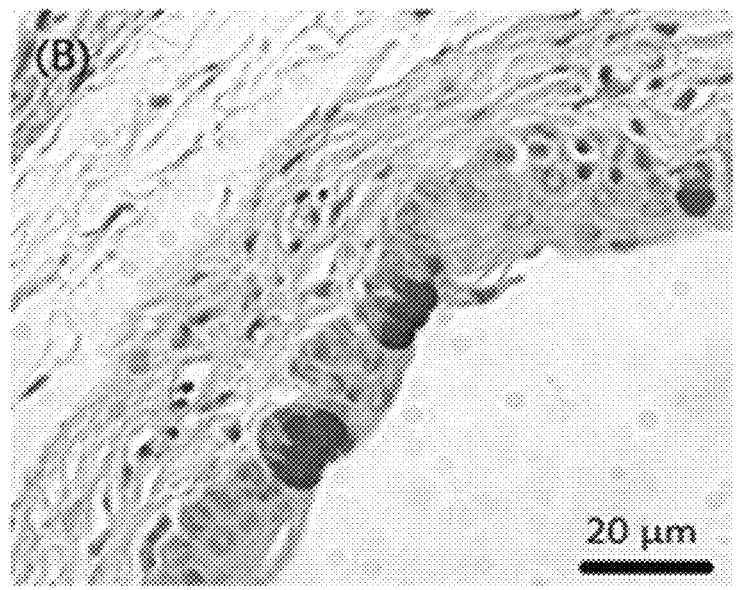
Figure 6C:
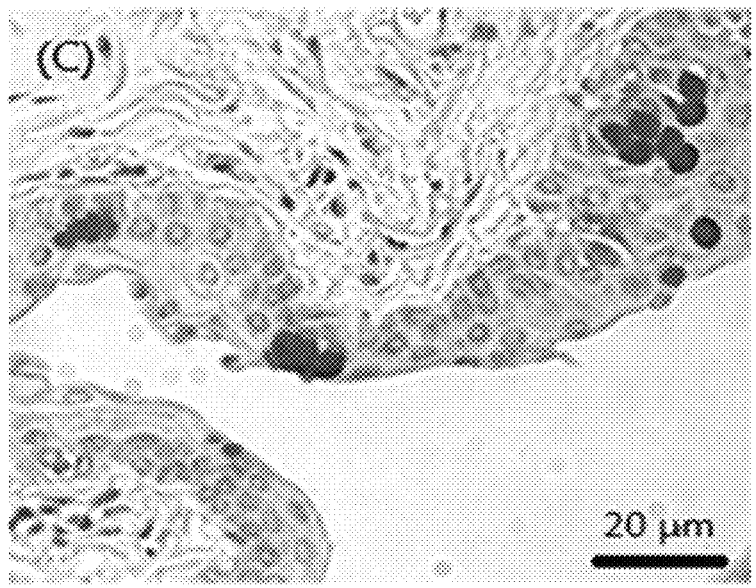
Figure 6D:
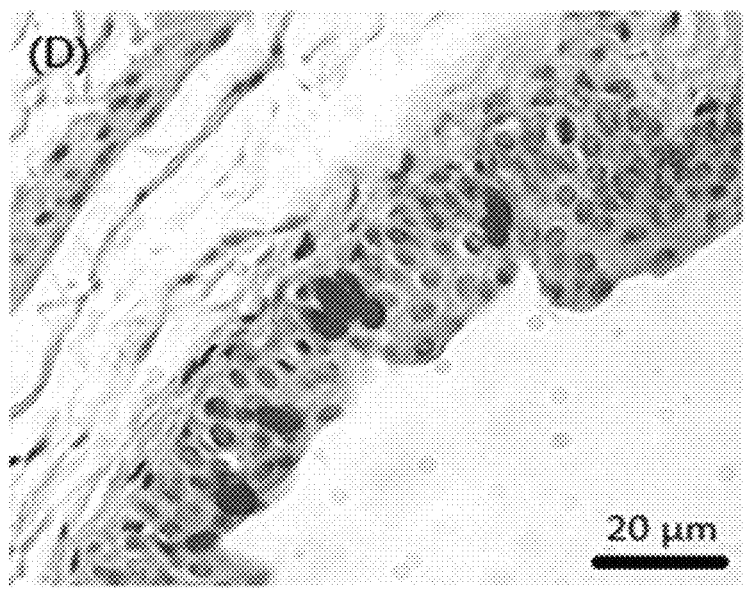
Figure 6E:
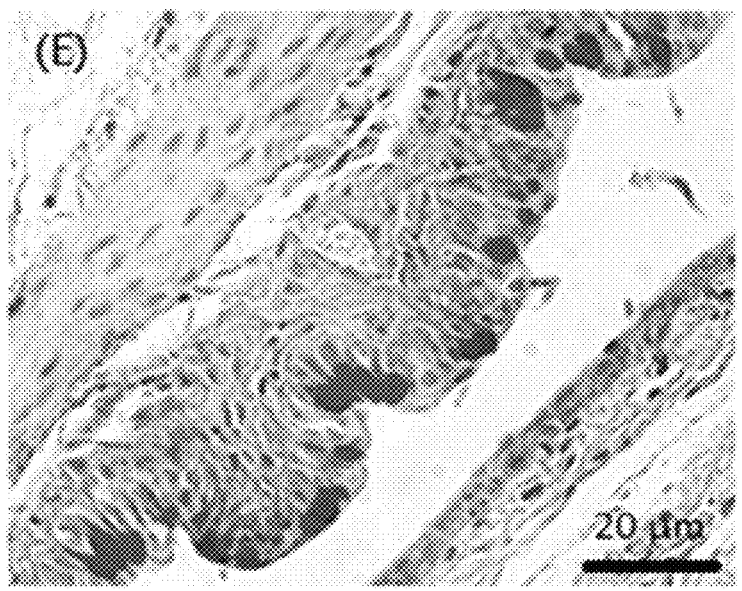
Figure 6F:
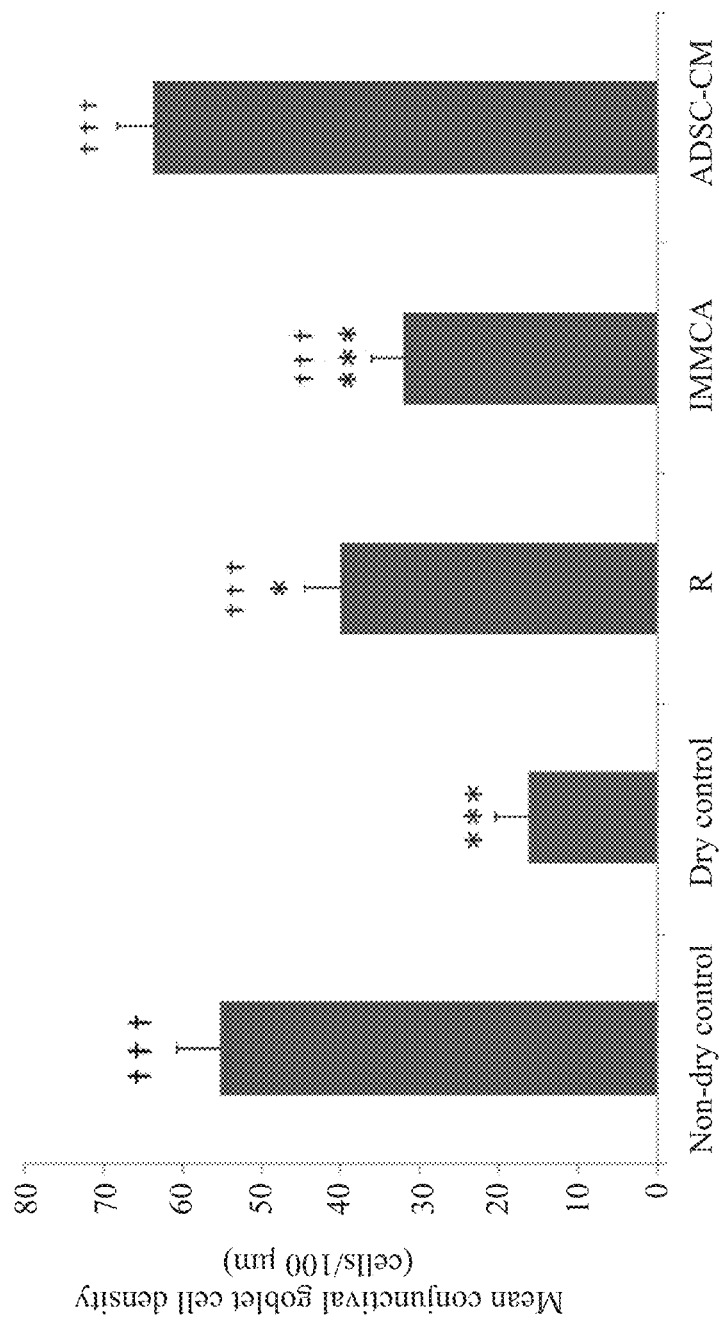
FIG. 6F shows the statistical comparison of the conjunctival goblet cell density between different groups of CEC induced dry eyes. * denotes comparison with non-dry control, *p<0.05, ***p<0.001. † denotes comparison with dry control, †p<0.05, †††p<0.001.

As shown in FIGS. 6A to 6E, the results of PAS staining showed that conjunctival goblet cells were reduced in the CEC-induced dry eyes. R and IMMCA partially reversed the reduction, while ADSC-CM best preserved the density of goblet cells. FIG. 6F provides a statistical comparison between the mean conjunctival goblet cell density observed in each group. As shown in FIG. 6F, ADSC-CM has the highest mean conjunctival goblet cell density among all the treatment groups, and is comparable to that of the non-dry control.

For MUC16 immunohistochemistry, the eyes were fixed in 10% formaldehyde. After paraffin embedding, 8-μm-thick sections were dewaxed in xylene, rehydrated in a series of ethanol solutions and washed twice in distilled water. Antigen retrieval was performed with DAKO Target Retrieval Solution, pH=9 (DAKO, Glostrup, Denmark) for 15 min at 90-95° C. MUC16 staining was performed on 8-μm-thick sections using Histofine Mouse Stain Kit (Nichirei, Tokyo, Japan). The sections were incubated with mouse anti-MUC16 (1:50; Santa Cruz, Santa Cruz, CA, USA) overnight at 4° C., and finally with Histofine Simple Stain Max PO for 10 min. The horseradish peroxidase reaction was developed with 3,3'-diaminobenzidine tetrahydrochloride with cobalt (D-0426, Sigma, Saint Louise, Missouri, USA). Negative control studies were also performed without using the primary antibodies. After dehydration in graded ethanol and xylene, sections were mounted in Histokit (Hecht Assistent, Sondheim, Germany) and analyzed.

Figure 7:
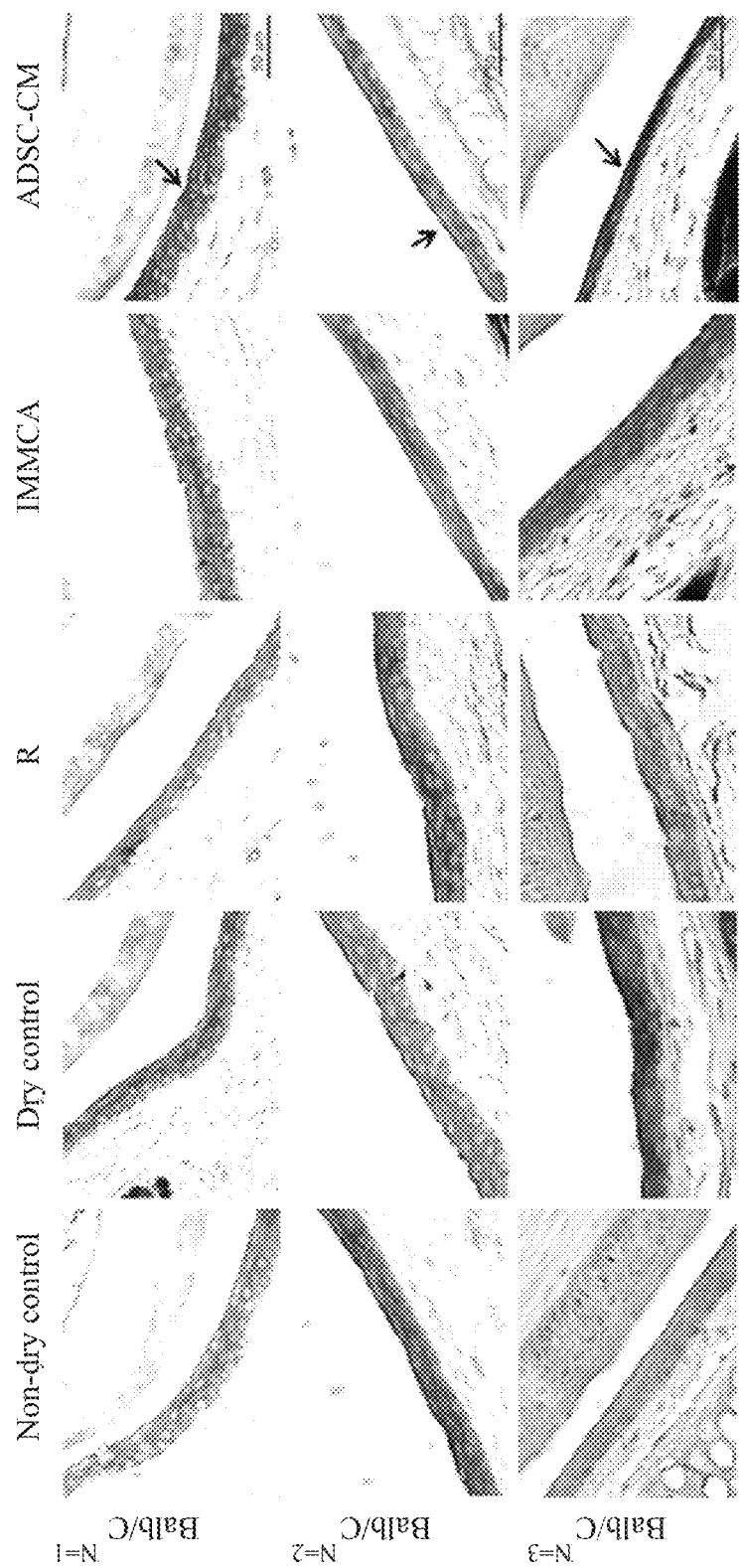
FIG. 7 shows the effects of different eye drops on the expression of membrane-associated mucins, MUC16, in conjunctival epithelium of the BALB/c mice in CEC by immunohistochemical analysis. The arrow in the ADSC-CM group indicates the conjunctival epithelium cell. Magnification: 400×. Scale bars: 50 µm, 5 µm sections.
Figure 8A:
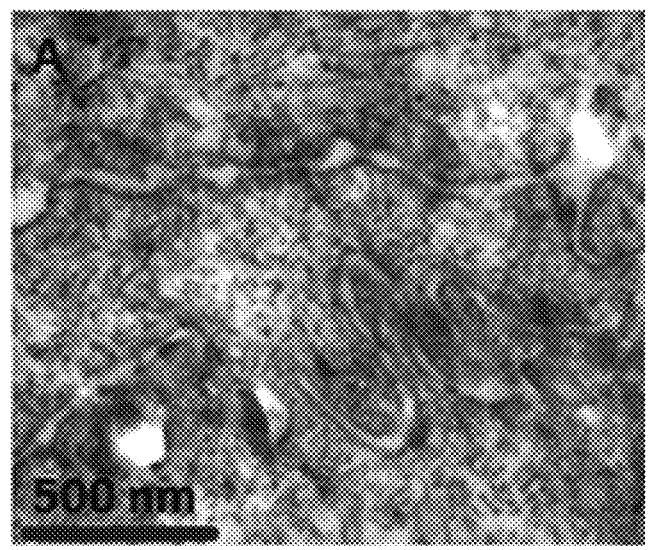
FIGS. 8A to 8E show the results of transmission electron microscopy of corneas from BALB/c mice housed in CEC treated with different eye drops.
Figure 8B:
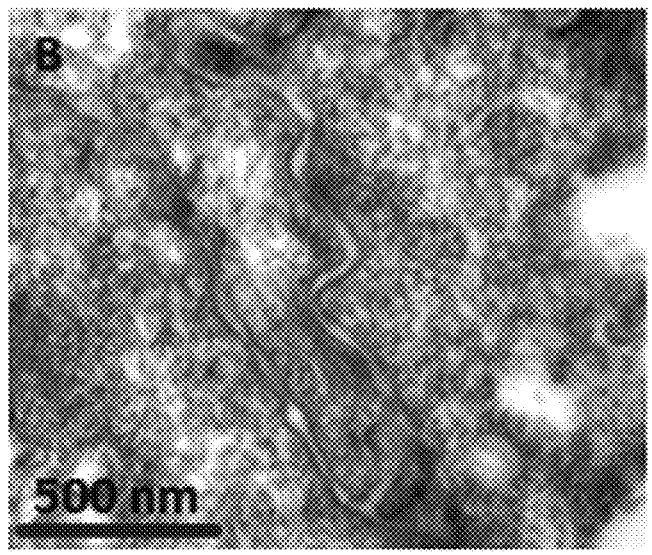
Figure 8C:
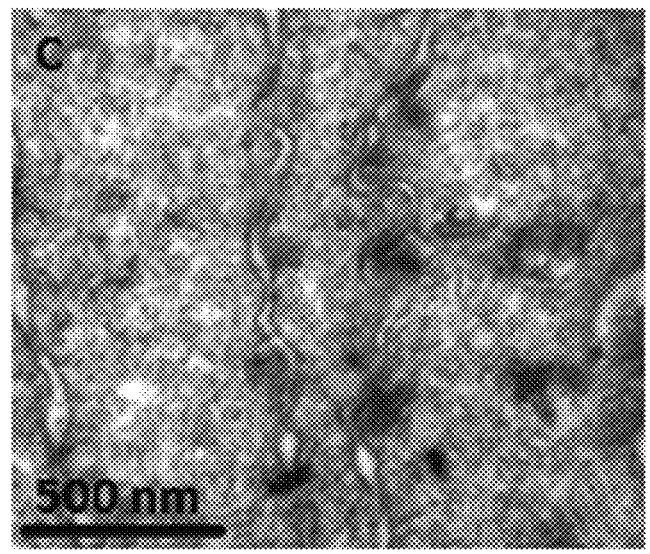
Figure 8D:
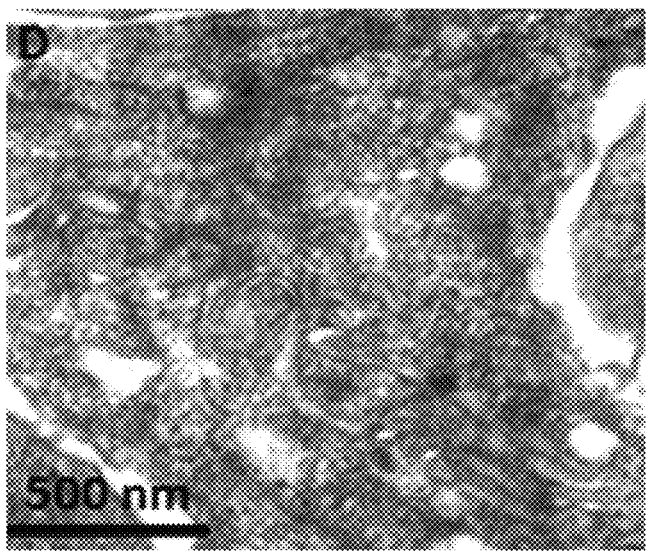
Figure 8E:
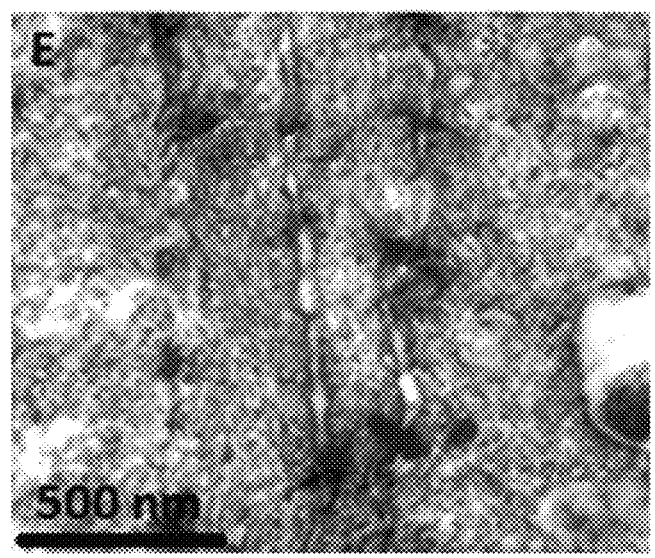
Figure 9A:
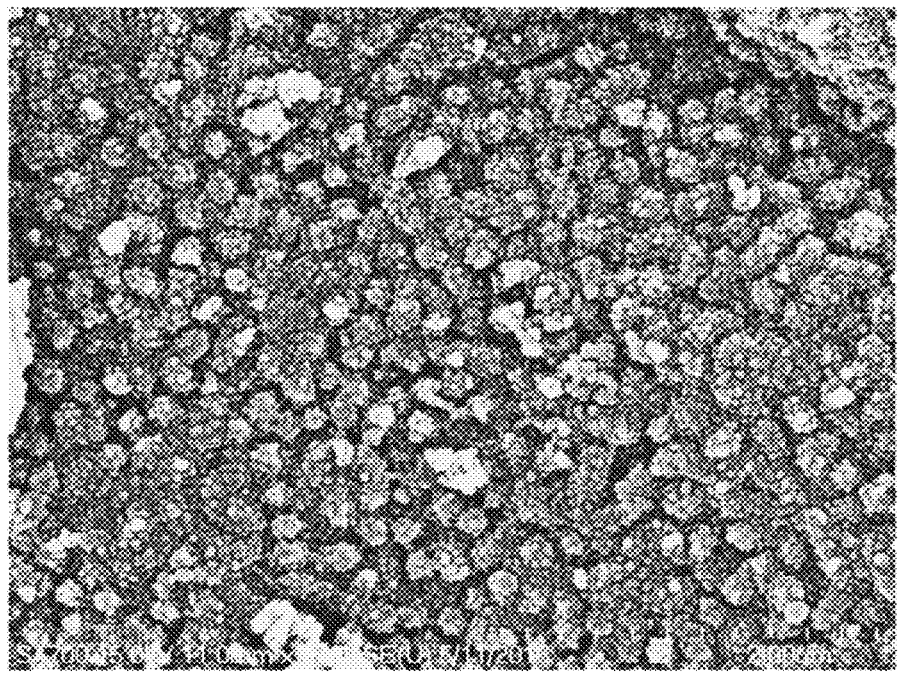
FIGS. 9A to 9E show the results of scanning electron microscopy of corneas from BALB/c mice housed in CEC treated with different eye drops.
Figure 9B:
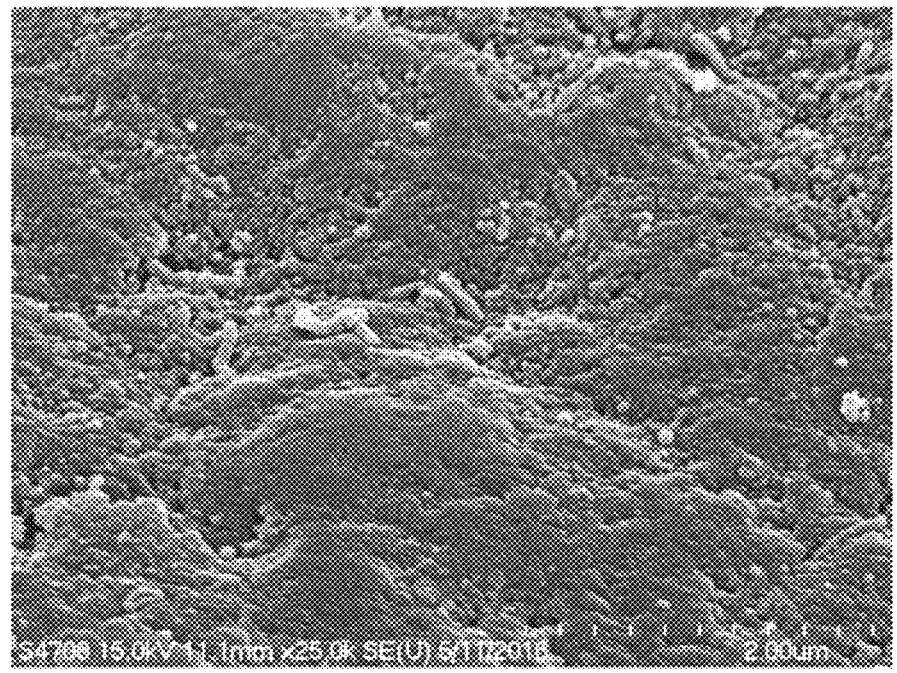
Figure 9C:
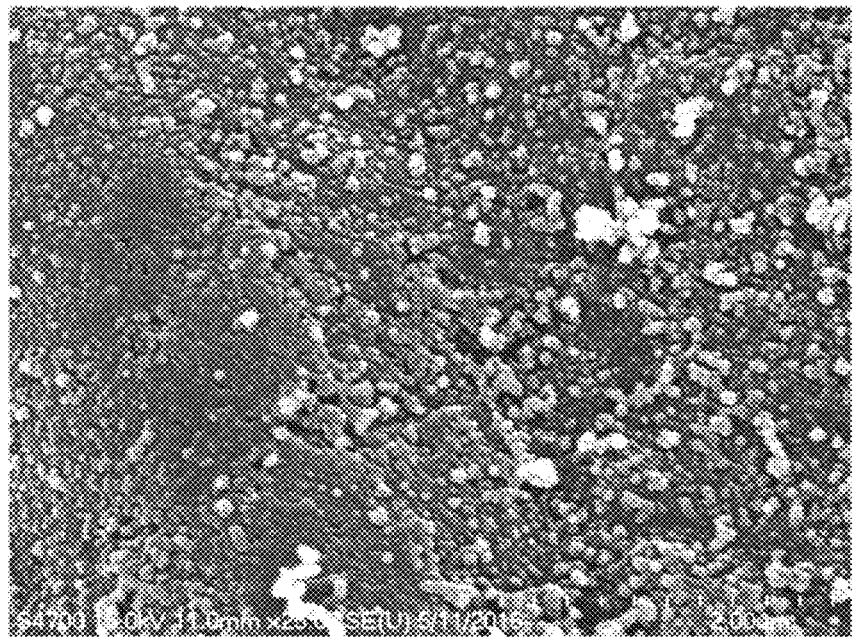
Figure 9D:
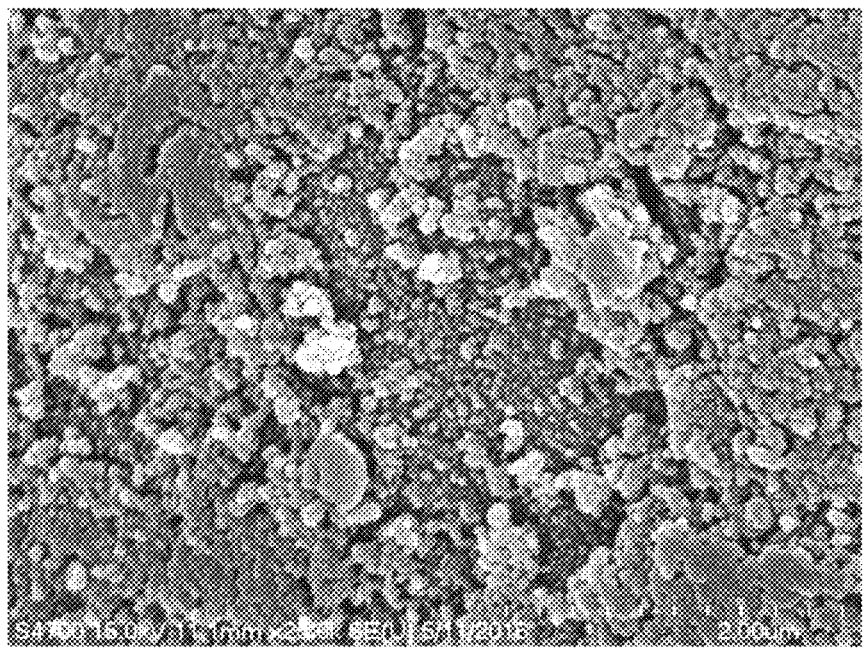
Figure 9E:
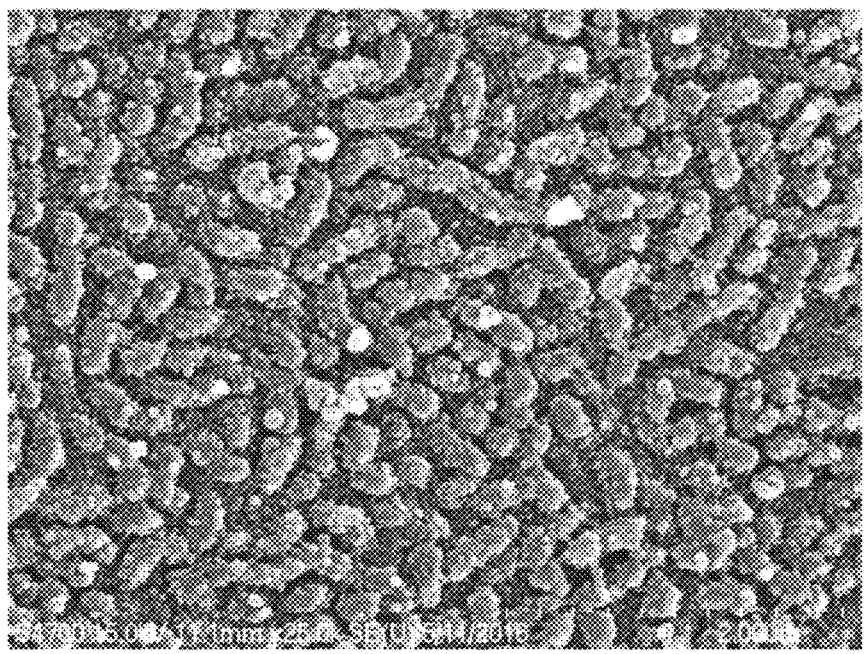
Figure 10A:
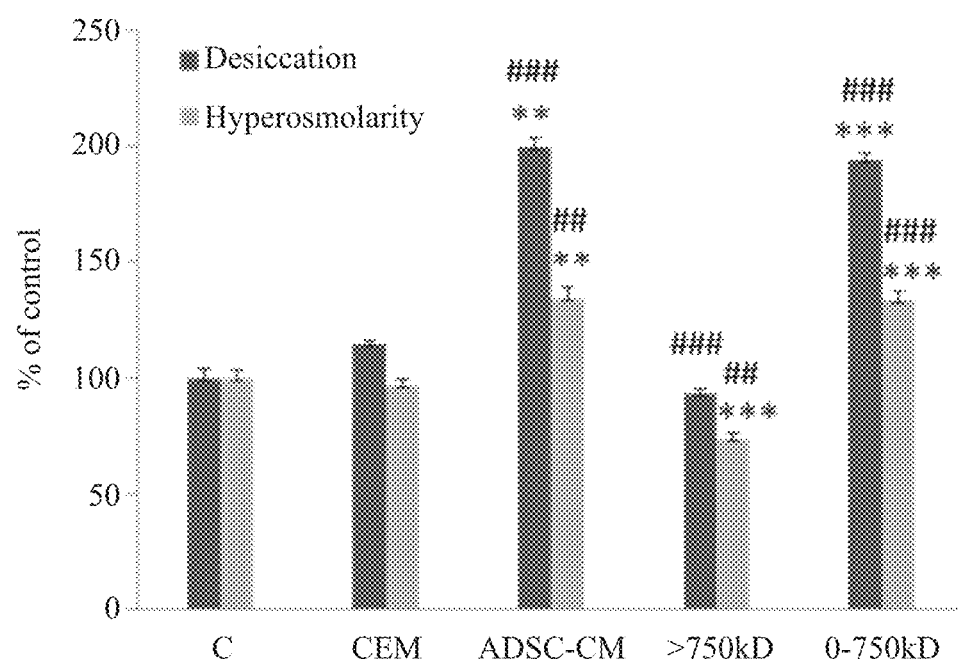
FIGS. 10A to 10D show the effect of different medium preparations and ADSC-CM fractions on viability of HCECs estimated by CCK-8 assay in a desiccation stress study and hyperosmolarity stress study. The values were presented as the means±SEM of three replicates. *P<0.05, P<0.01, *P<0.001 compared with the control. *P<0.05, ##P<0.01, " " P<0.001 compared with the CEM.
Figure 10B:
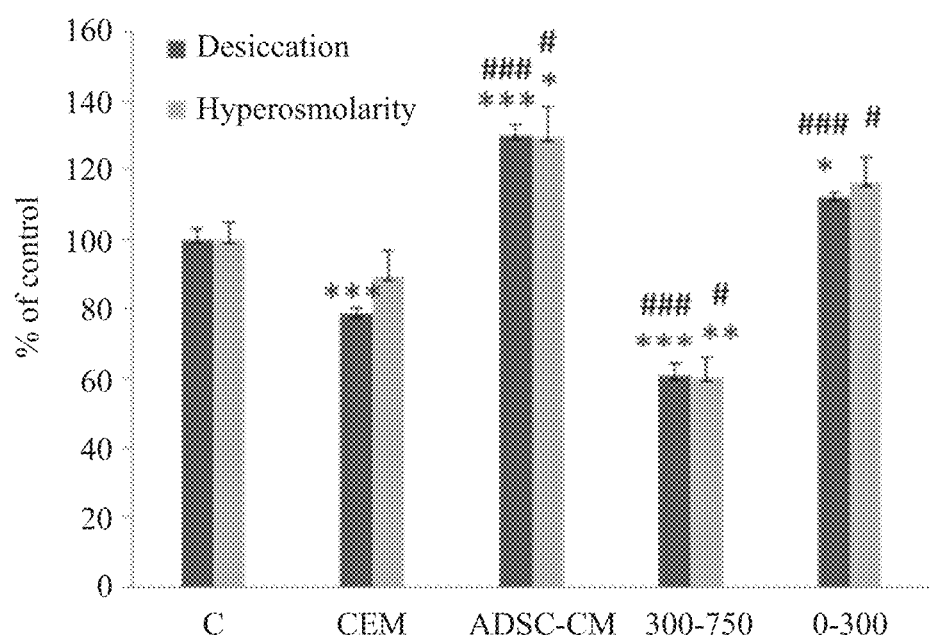
Figure 10C:
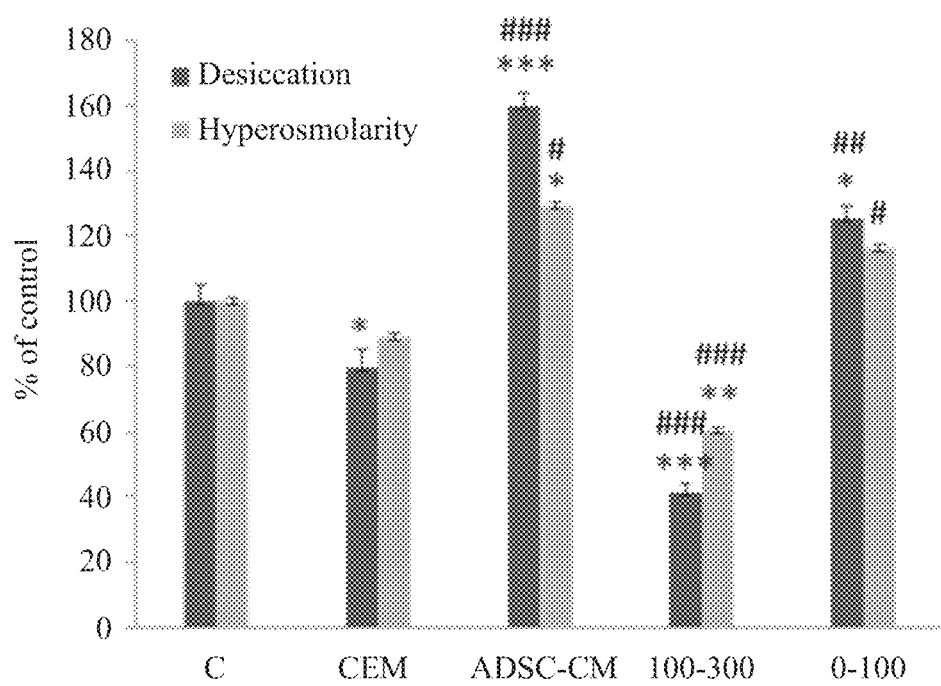
Figure 10D:
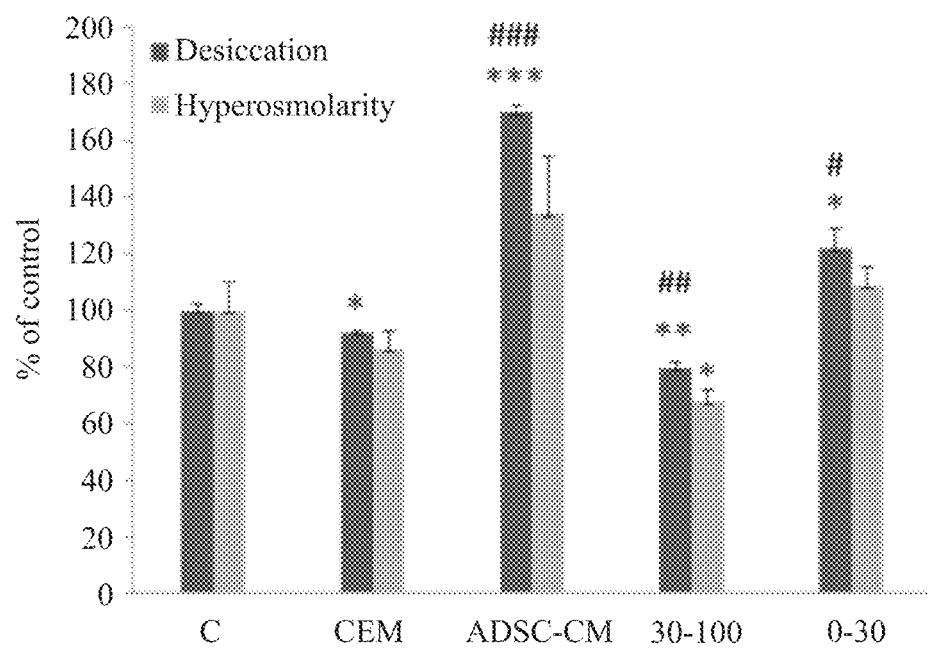

As shown in FIG. 7, the immunohistochemical analysis of MUC16 showed that conjunctival MUC16 expression was continuous in the non-dry group, but disrupted in the dry group, R group and IMMCA group. However, topical application of ADSC-CM in the CEC-dry eye mice helped keep the continuous expression of MUC16. Moreover, the results also showed that the ADSC-CM group had the best expression of MUC16. The arrow in the ADSC-CM group indicates the conjunctival epithelium cell.

6. Transmission Electron Microscopy (TEM) Analysis

Fresh corneal samples were first fixed in 2% paraformaldehyde for 24 hours, and were then fixed in 2.5% glutaraldehyde solution in 0.2 M cacodylate buffer and then plus 1% tannic acid at pH 7.0-7.3 for 24 hours, and postfixed for 1 hour with 1% osmium tetroxide solution in 0.2 M cacodylate buffer solution. After further postfixation, samples were en bloc-stained with 0.2% uranyl acetate for 2 hours, and then dehydrated by ethanol/acetone and embedded in pure Spurr's resin for 8 hours at room temperature. Finally, the samples were polymerized for 62° C. at 48 hours and then photographed under transmission electron microscope (Hitachi H-7500, Hitachi Ltd., Japan).

As shown in FIGS. 8A-8E, the TEM study revealed decreased tight junction and interdigitations between corneal epithelial cells in CEC-induced dry eye mice. Treatment with ADSC-CM increased the interdigitation and tight junction formation between adjacent corneal epithelial cells.

7. Scanning Electron Microscopy (SEM) Analysis

Fresh corneas were first fixed in 2% paraformaldehyde for 24 hours, and then in 2.5% glutaraldehyde solution in 0.2 M cacodylate buffer solution and 1% tannic acid at pH 7.0-7.3 for another 24 hours, followed by postfixation with 1% osmium tetroxide solution in 0.2 M cacodylate buffer solution for 1 hour. Samples were then dehydrated by critical point dryer (Hitachi Ltd., Japan), and coated with platinum in an ion sputter coater (Hitachi Ltd., Japan). Finally, the samples were observed and photographed with the scanning electron microscope (Hitachi Ltd., Japan).

As shown in FIGS. 9A-9E, the SEM study demonstrated that the microvilli of corneal epithelium were lost in the CEC-induced dry eye mice. Topical application of R and IMMCA partially preserved the microvilli of corneal epithelium, while ADSC-CM protected the microvilli best from dry damage.

Example 3: In Vitro Human Corneal Epithelial Cells (HCECs) Desiccation Stress Study with Different Size Fractions of ADSC-CM Different size fractions of ADSC-CM were prepared as described in preparation example 3 above. ADSC-CM fractions containing >750 kDa, 0-750 kDa, 300-750 kDa, 0-300 kDa, 100-300 kDa, 0-100 kDa, 30-100 kDa, and 0-30 kDa were obtained and subjected to desiccation stress and hyperosmolarity stress, and then evaluated by CCK-8 assay. Desiccation stress study by CCK-8 assay was as described above in Example 2. For the hyperosmolarity stress, the HCECs were grown to approximately 60% confluence and then treated for 24 hours with fresh medium (311 milliosmole (mOsM)) or the medium containing 90 mM NaCl (480 mOsM). After hypertonic treatment, the cells were cultured in different culture media. The cells were subjected to CCK-8 assay after 2 hours of incubation.

The results were shown in FIGS. 10A-10D. ADSC-CM fractions containing 0-750 kDa, 0-300 kDa, 0-100 kDa, and 0-30 kDa were shown to have the effect of maintaining the ADSC-CM's effects in protecting the cells from desiccation stress and hyperosmolarity stress.

Figure 11:
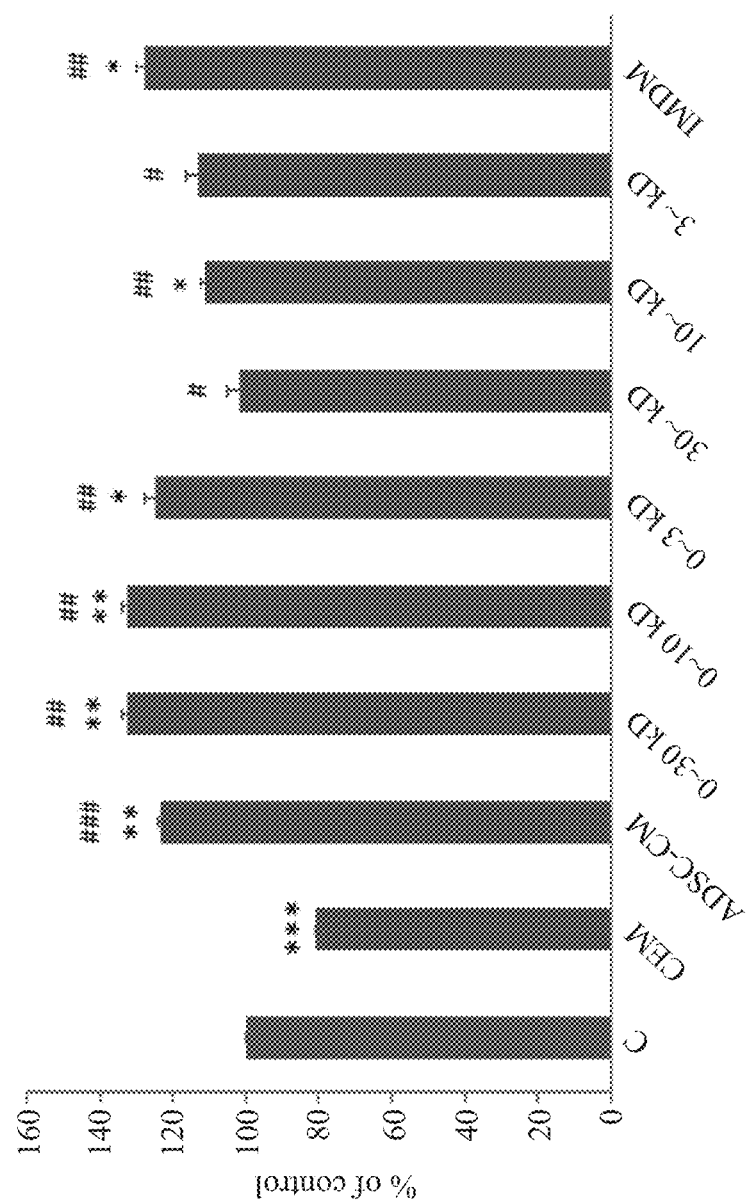
FIG. 11 shows the effect of different medium preparations and ADSC-CM fractions on viability of HCECs estimated by CCK-8 assay in a desiccation stress study. The values were presented as the means±SEM of three replicates. *P<0.05, P<0.01, *P<0.001 compared with the control. #P<0.05, ##P<0.01, ###P<0.001 compared with the CEM.

Further size fractions of ADSC-CM were prepared to analyze the size of the active ingredients in the ADSC-CM. ADSC-CM fractions containing 0-30 kDa, 0-10 kDa, 0-3 kDa, >30 kDa, >10 kDa, and >3 kDa were obtained and subjected to desiccation stress study evaluated by CCK-8 assay as described above. The results were shown in FIG. 11, indicating that ADSC-CM fractions containing 0-30 kDa, 0-10 kDa, and 0-3 kDa have a better effect in maintaining the ADSC-CM's effects in protecting the cells from desiccation stress than the ADSC-CM fractions containing >30 kDa, >10 kDa and >3 kDa.

Figure 12:
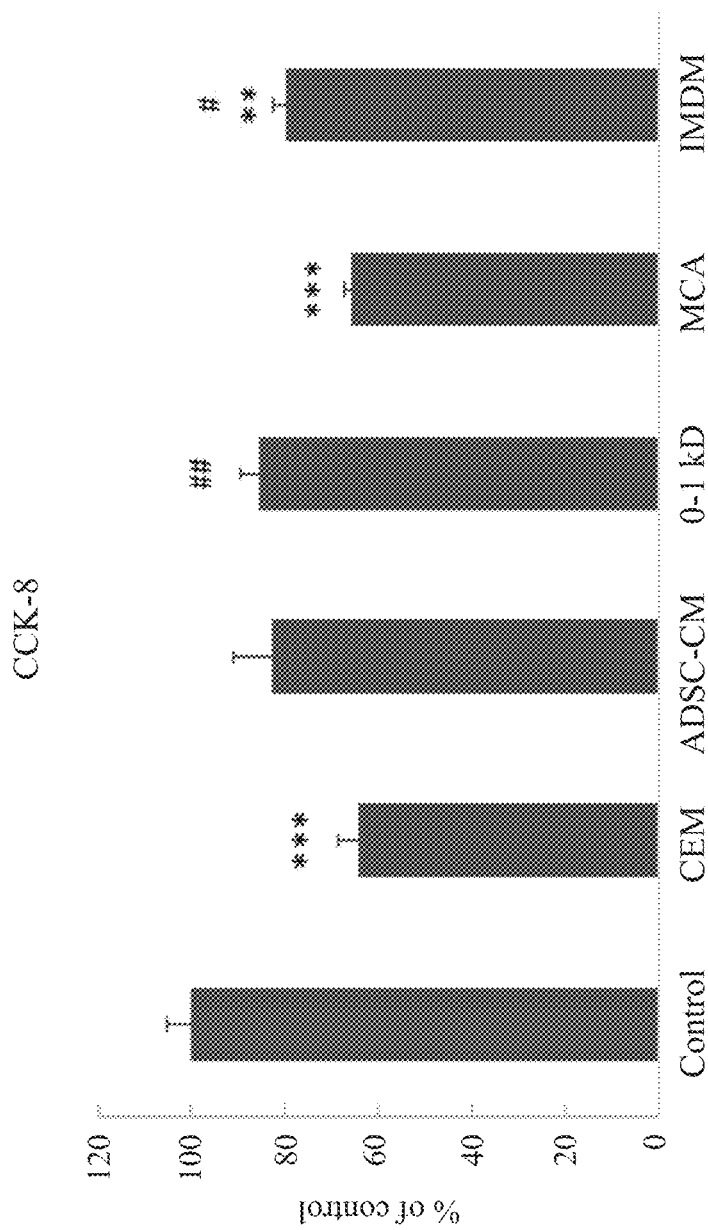
FIG. 12 shows the effect of different medium preparations and the ADSC-CM fraction of 0-1 kDa on viability of HCECs estimated by CCK-8 assay in a desiccation stress study. The values were presented as the means±SEM of three replicates. *P<0.05, P<0.01, *P<0.001 compared with the control. #P<0.05, ##P<0.01, ###P<0.001 compared with the CEM.

The same desiccation stress study evaluated by CCK-8 assay was repeated on ADSC-CM fractions containing 0-1 kDa, and the result was shown in FIG. 12. ADSC-CM fractions containing 0-1 kDa is still effective in protecting the cells from desiccation stress, with a similar percentage of cells preserved as those treated with ADSC-CM.

Example 4: In Vivo Animal Study of Dry Eyes with ADSC-CM in Different Size Fractions ADSC-CM fractions prepared from above were further evaluated for effects in treating dry eyes with in vivo animal study. Tear secretion assay, immunofluorescence double staining, histological analysis, immunohistochemistry (IHC) assay, transmission electron microscopy (TEM) analysis, and scanning electron microscopy (SEM) analysis were carried out as described above.

Figure 13A:
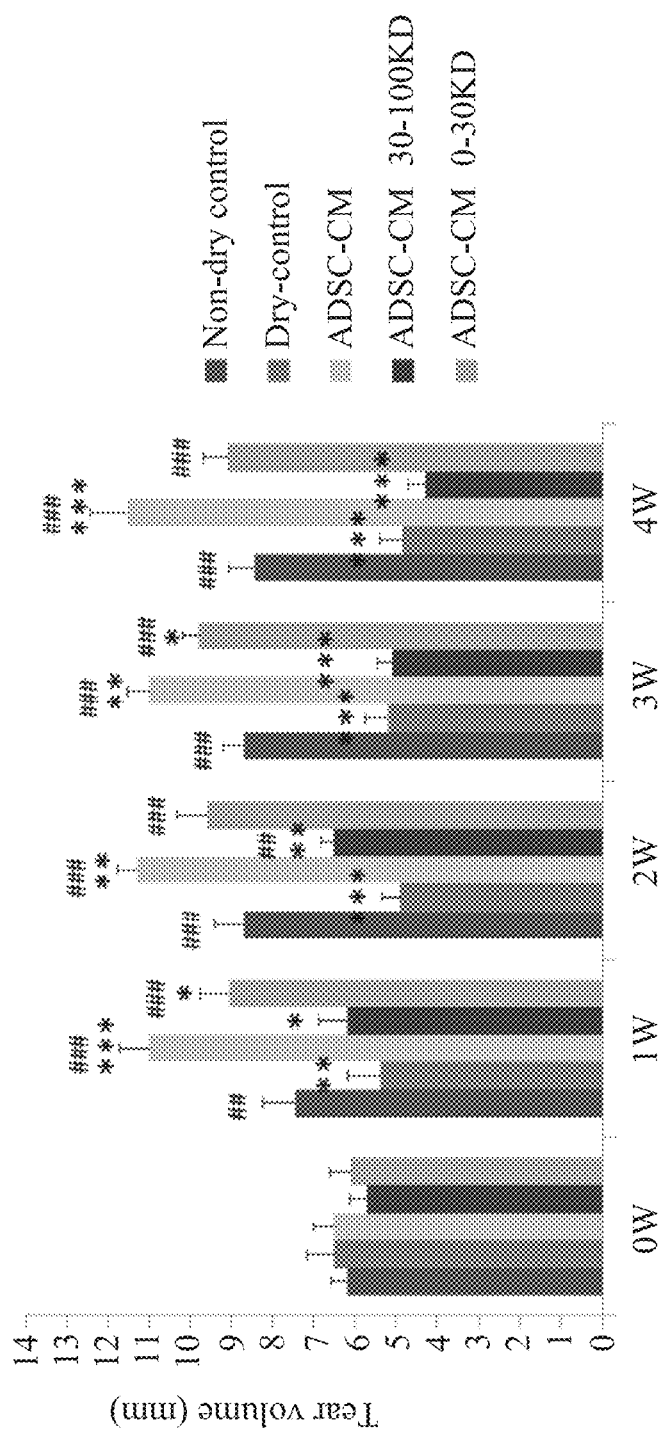
FIGS. 13A to 13C show the tear volume of mice housed in CEC chamber treated with different ADSC-CM fractions. Mean tear volumes in each group were shown. * compared with non-dry control, *p<0.05, p<0.01, *p<0.001. #compared with Dry control, #p<0.05, ##p<0.01, ###p<0.001. Mean SEM, N=4.
Figure 13B:
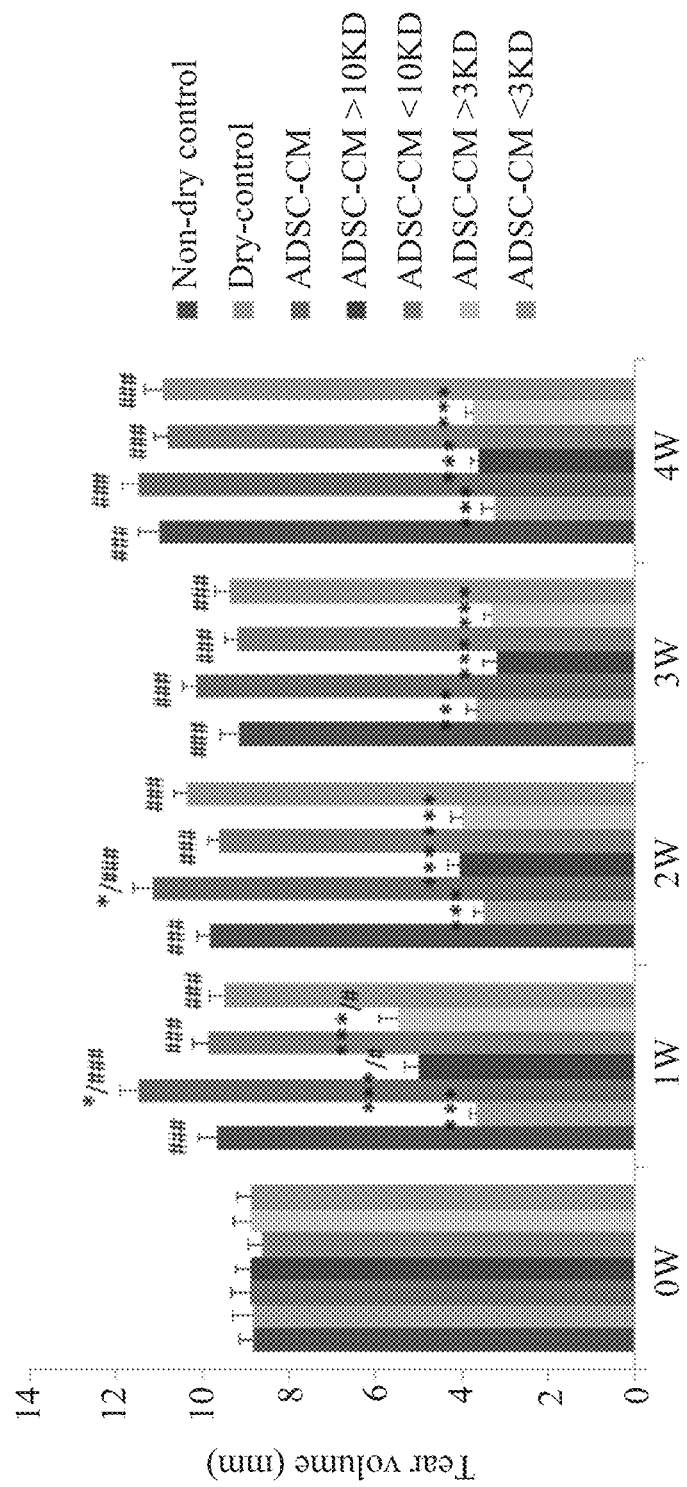
Figure 13C:
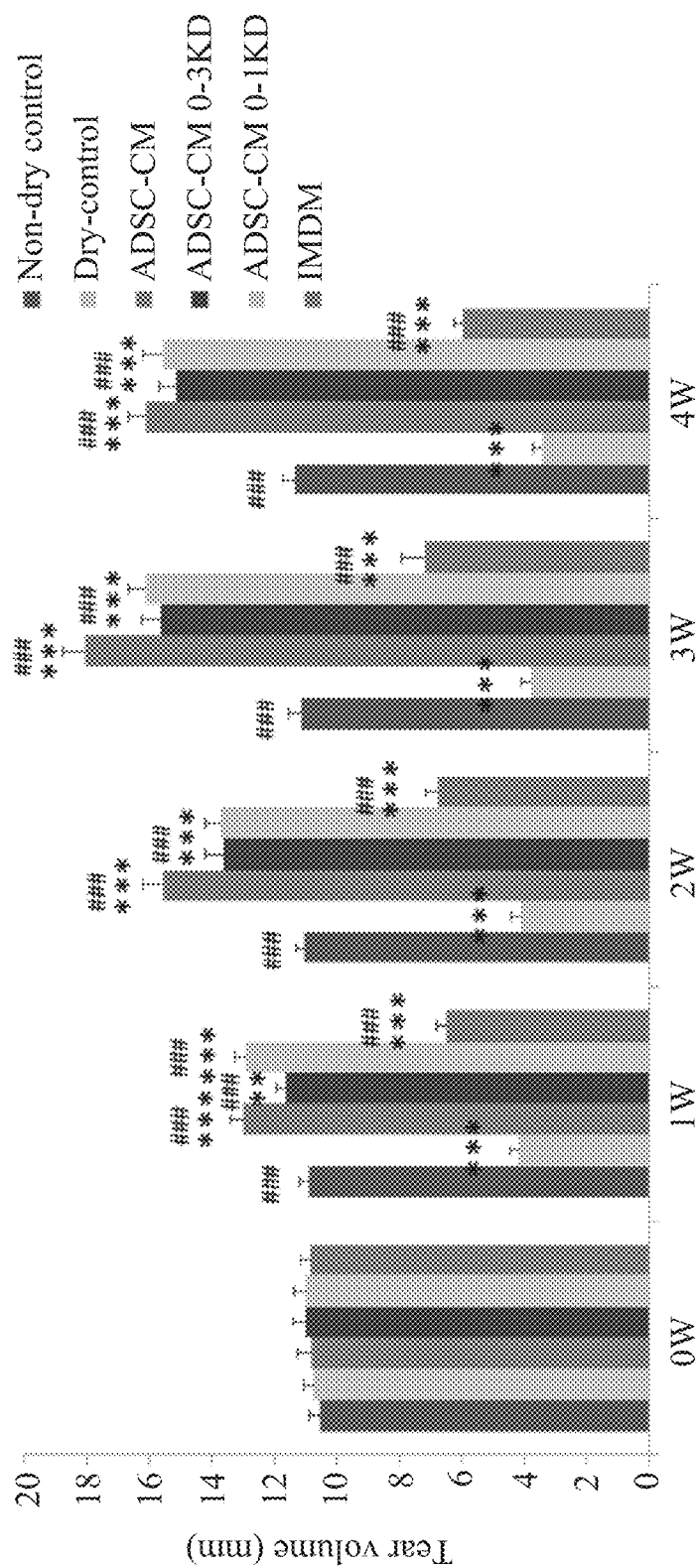
Figure 14A:
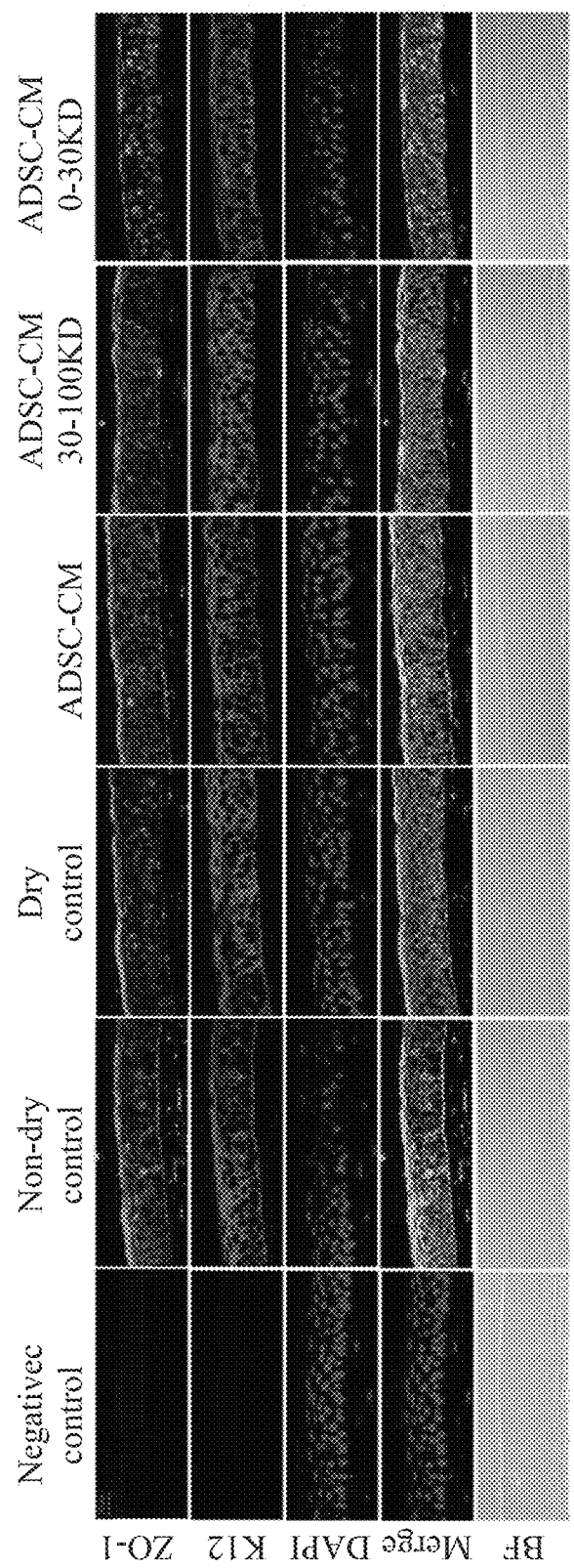
FIGS. 14A to 14B, FIGS. 15A to 15B and FIGS. 16A to 16B show the confocal microscopic examination of corneal epithelium and the integrity of tight junction barriers of corneal epithelium of BALB/c mice in the CEC-induced dry eye model with the treatment of different ADSC-CM fractions. BF: Bright Field.
Figure 14B:
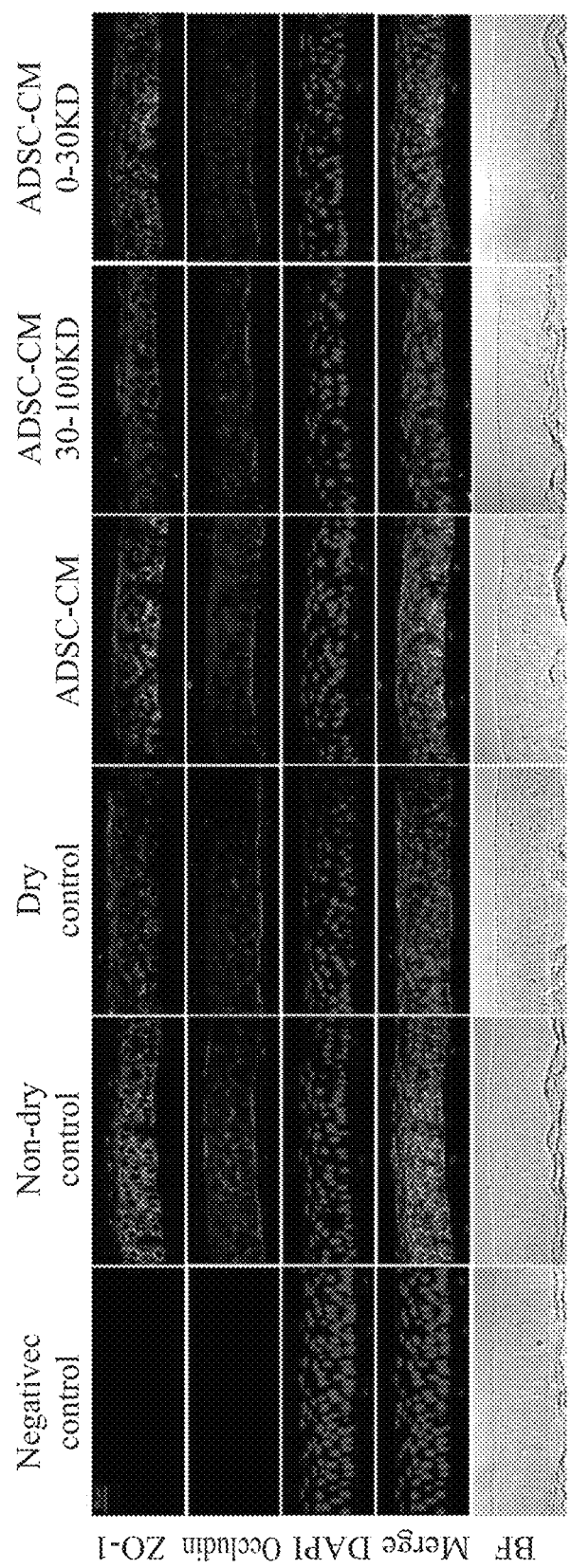
Figure 15A:
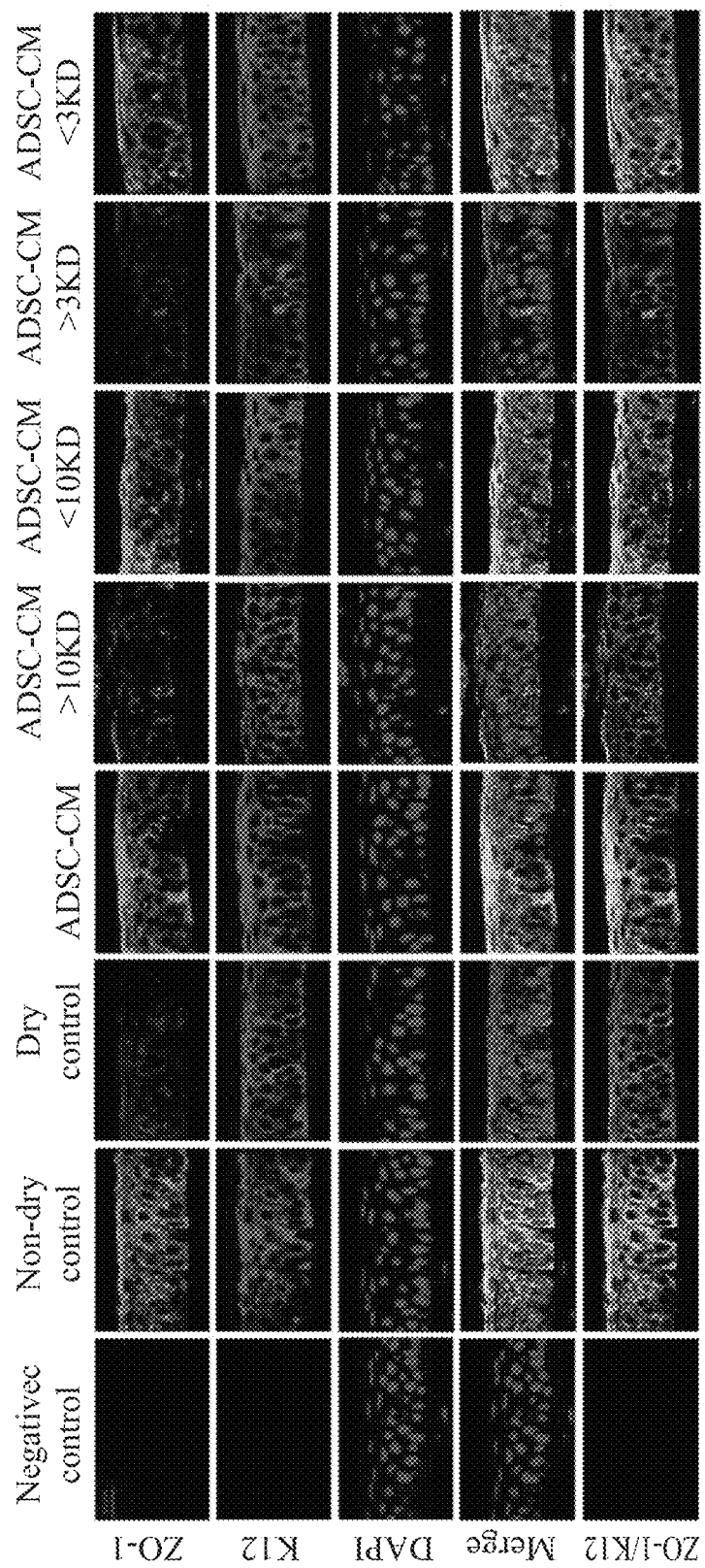
Figure 15B:
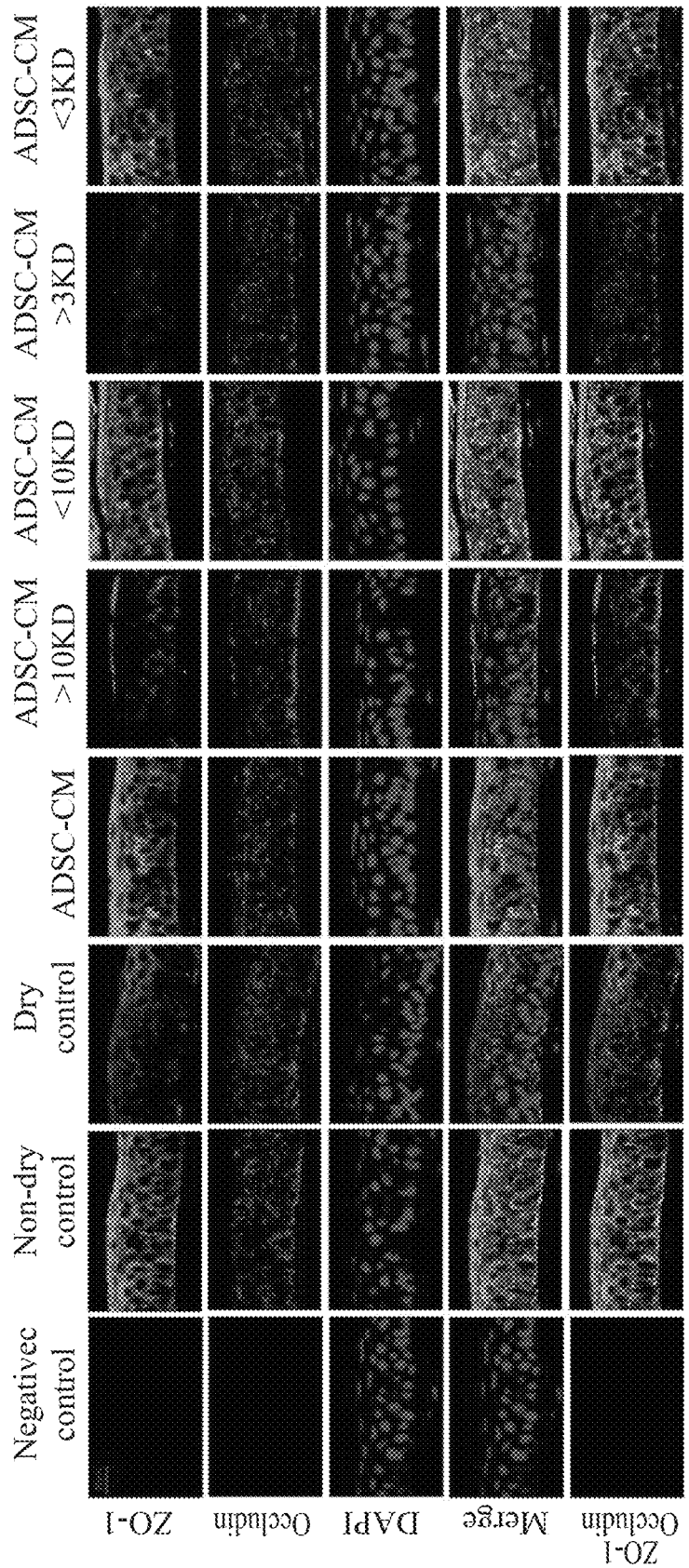
Figure 16A:
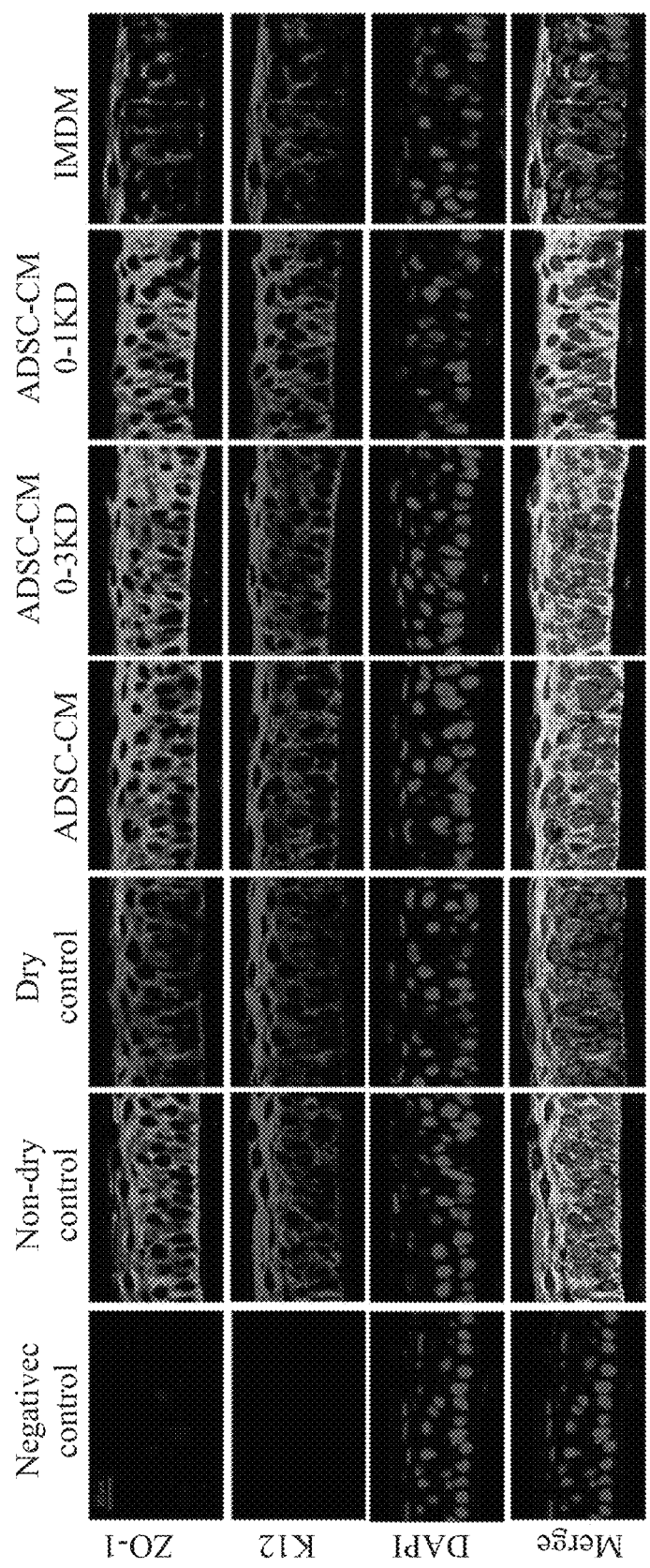
Figure 16B:
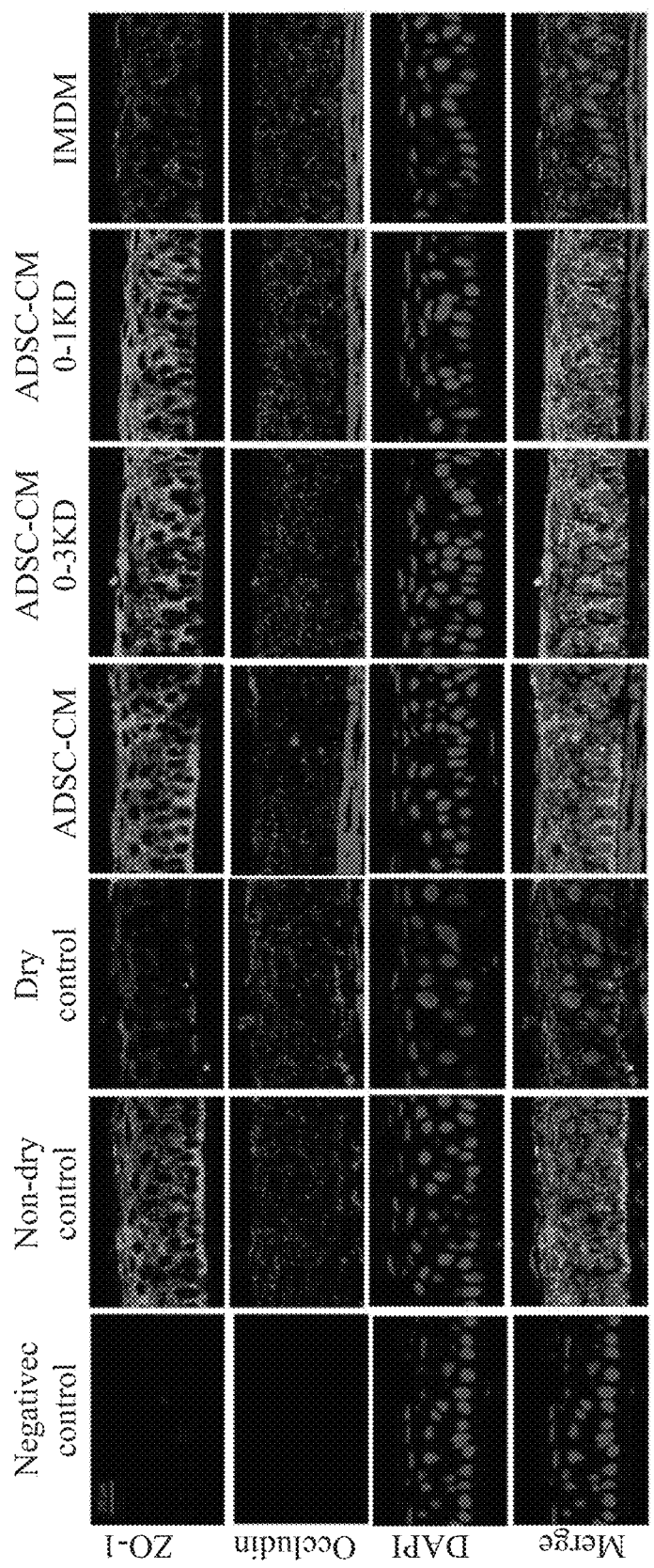
Figure 17A:
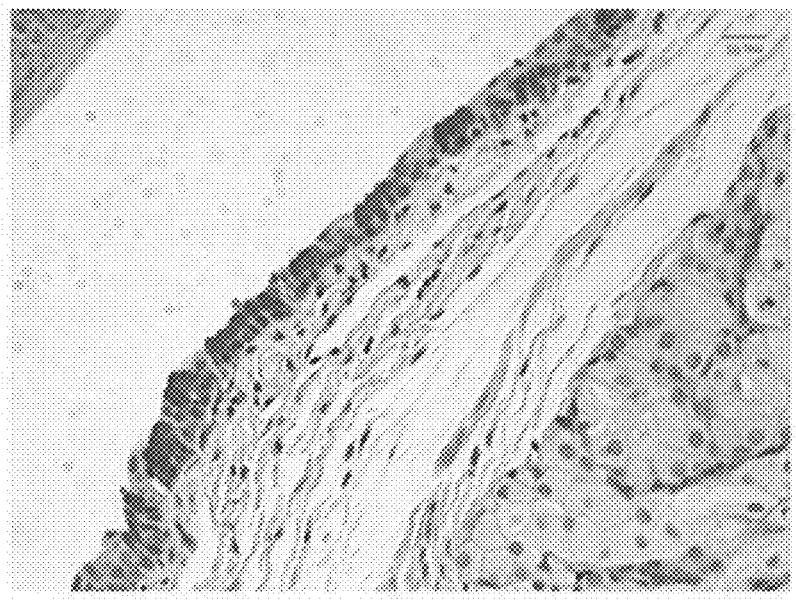
FIGS. 17A to 17E show the results of PAS staining of the conjunctival goblet cells in different groups of CEC induced dry eyes.
Figure 17B:
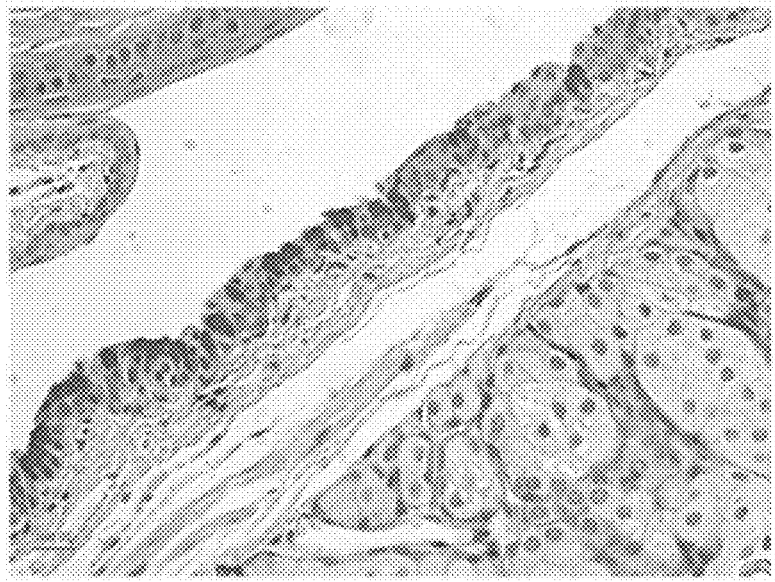
Figure 17C:
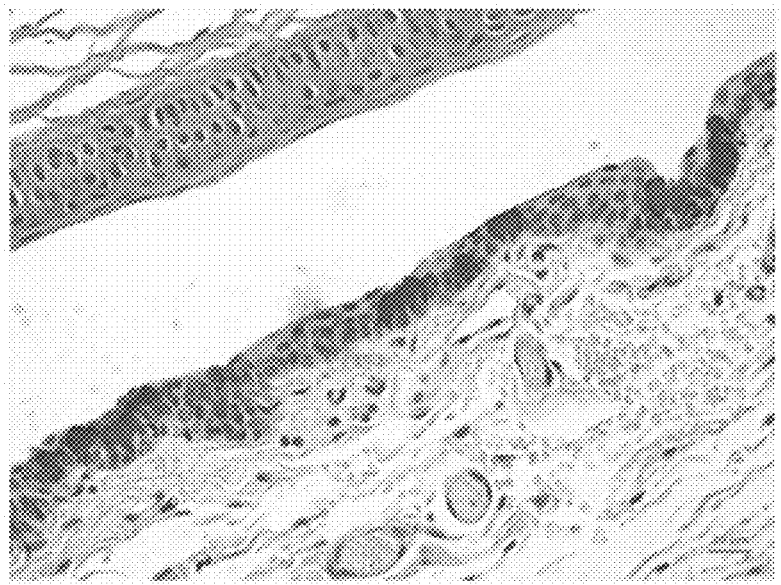
Figure 17D:
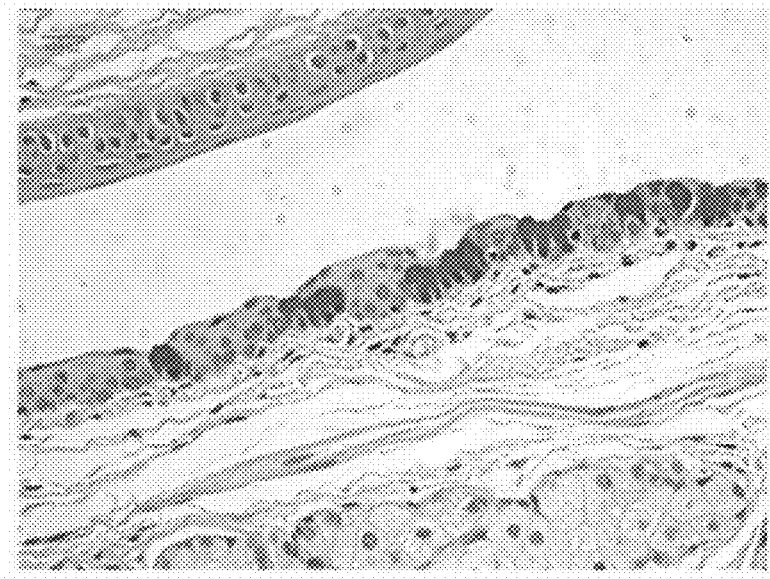
Figure 17E:
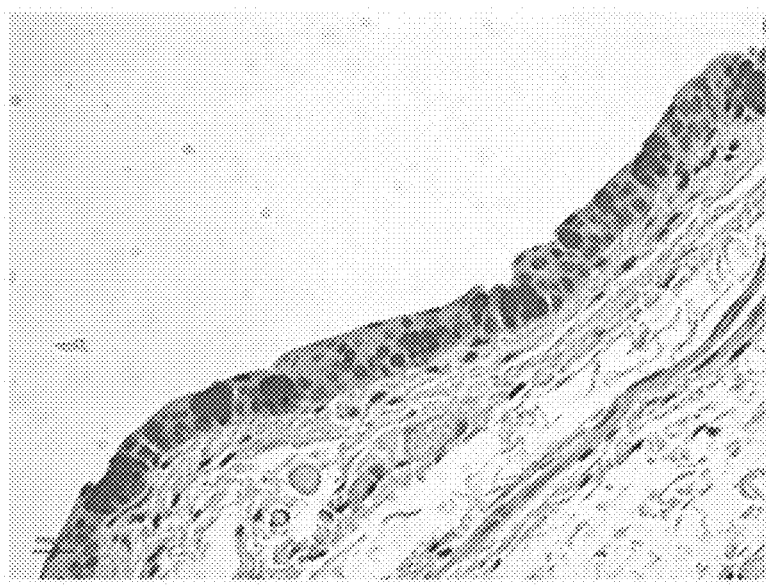
Figure 17F:
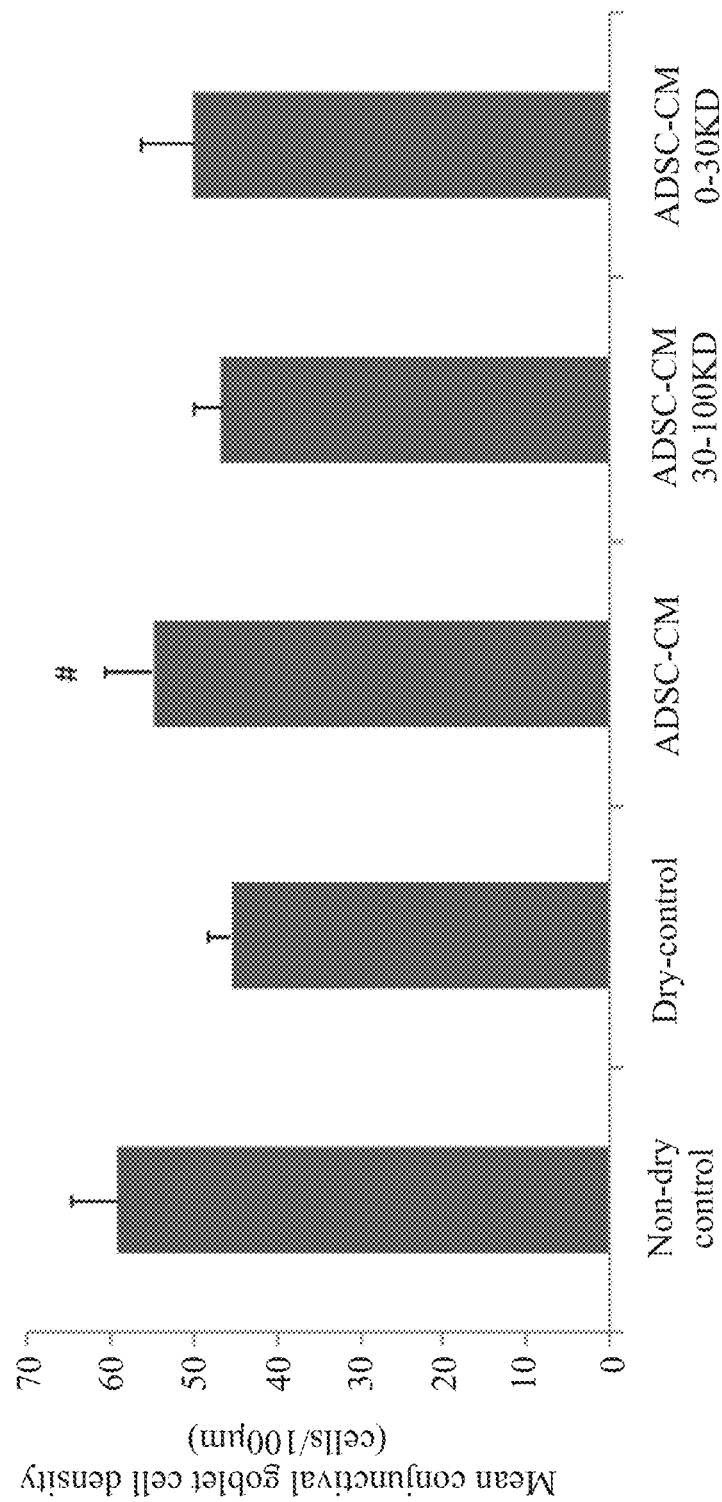
FIG. 17F shows the statistical comparison of the conjunctival goblet cell density between different groups of CEC induced dry eyes. #compared with Dry control, #p<0.05.
Figure 18A:
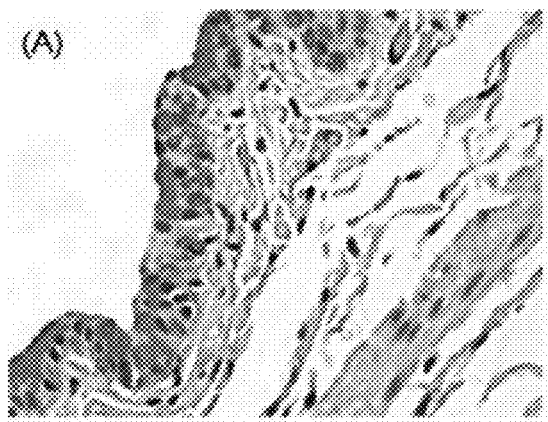
FIGS. 18A to 18G show the results of PAS staining of the conjunctival goblet cells in different groups of CEC induced dry eyes.
Figure 18B:
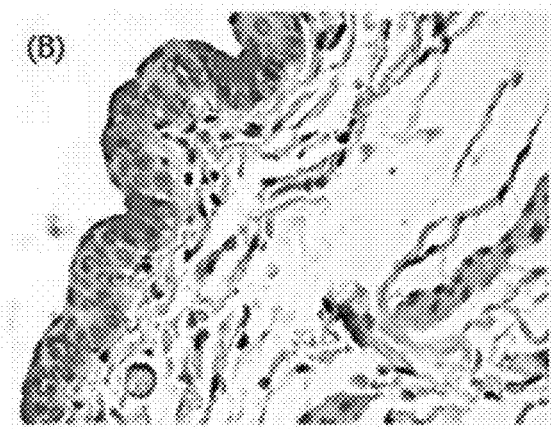
Figure 18C:
Figure 18D:
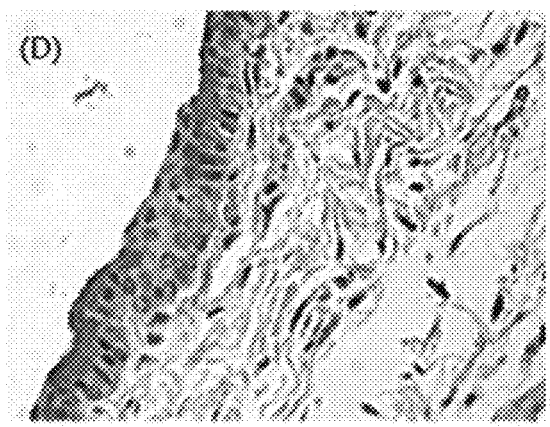
Figure 18E:
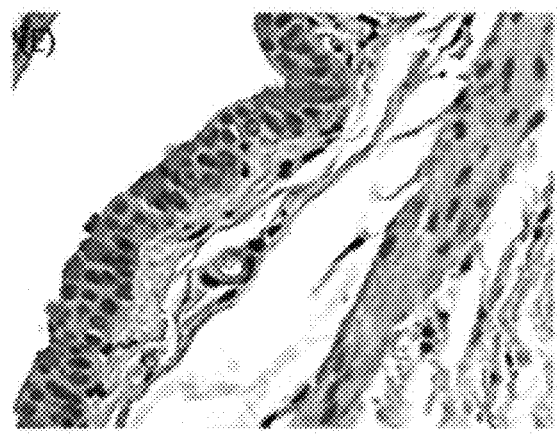
Figure 18F:
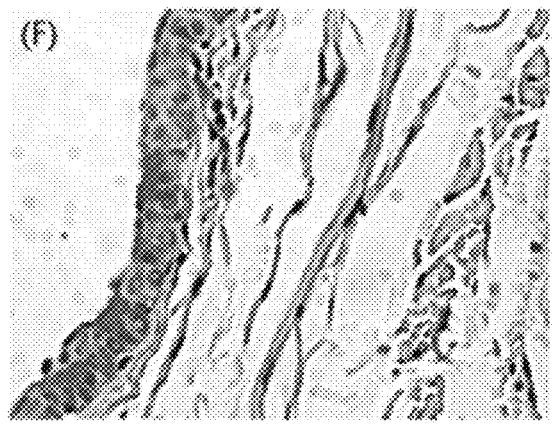
Figure 18G:
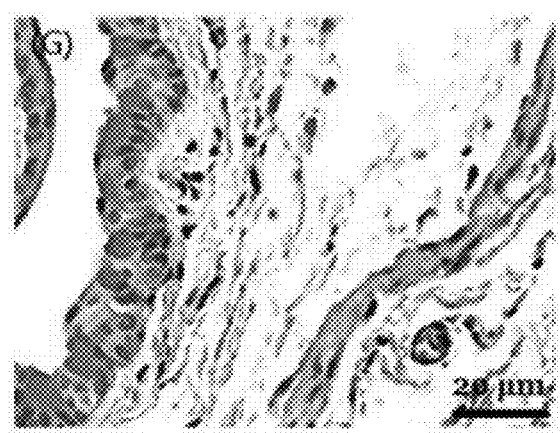
Figure 18H:
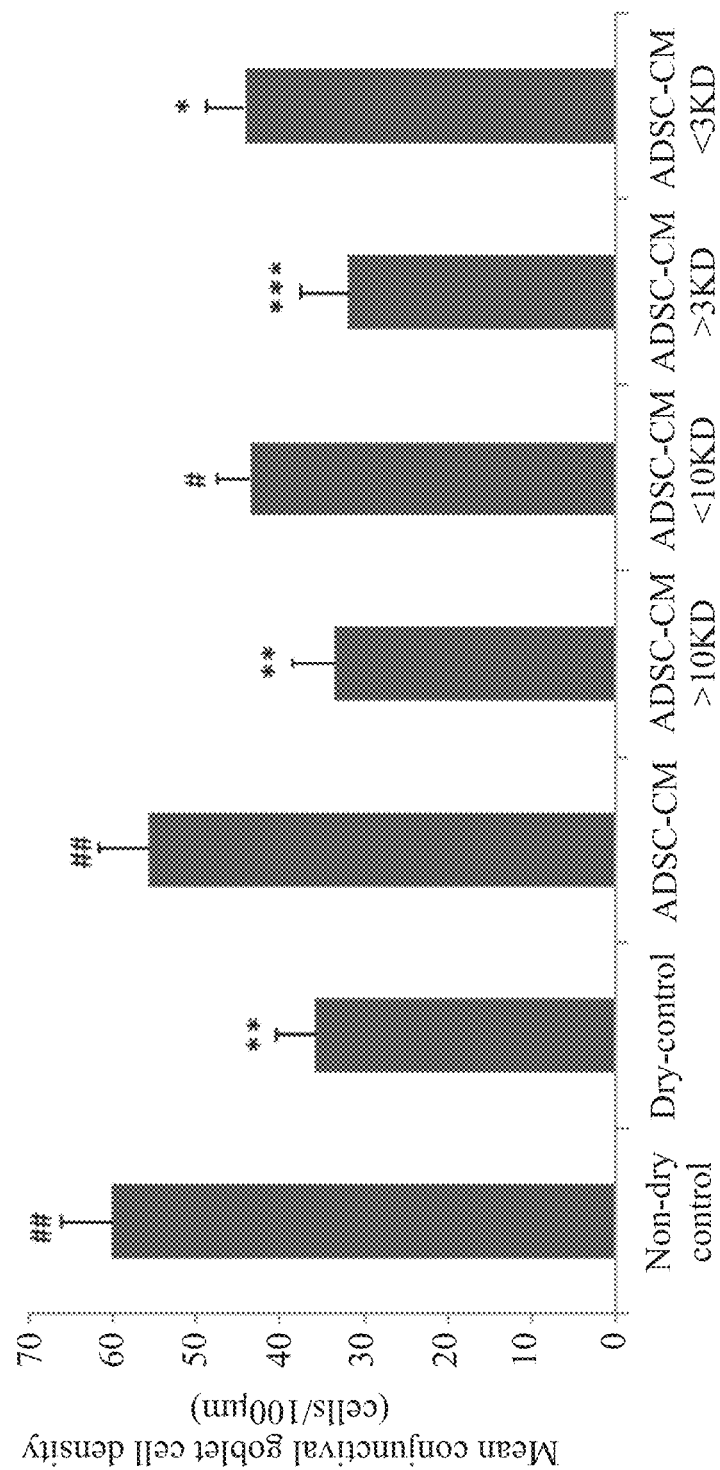
FIG. 18H shows the statistical comparison of the conjunctival goblet cell density between different groups of CEC induced dry eyes. * compared with non-dry control, *p<0.05, p<0.01, *p<0.001. #compared with Dry control, #p<0.05, ##p<0.01, ###p<0.001.
Figure 19A:
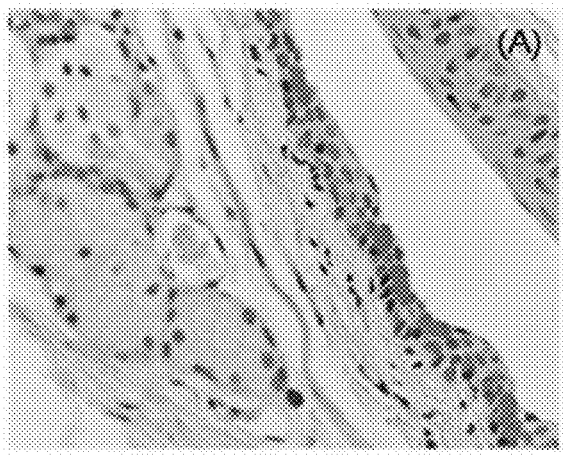
FIGS. 19A to 19F show the results of PAS staining of the conjunctival goblet cells in different groups of CEC induced dry eyes.
Figure 19B:
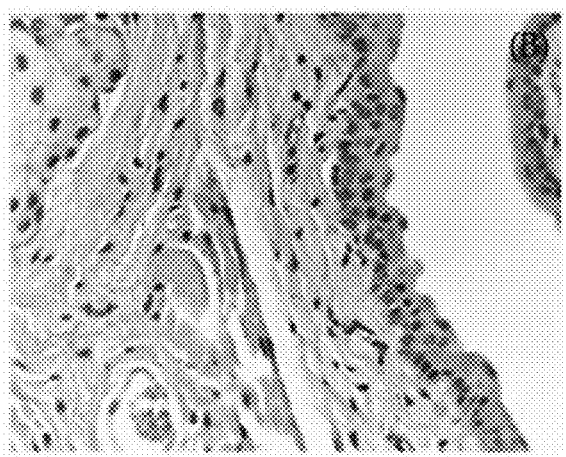
Figure 19C:
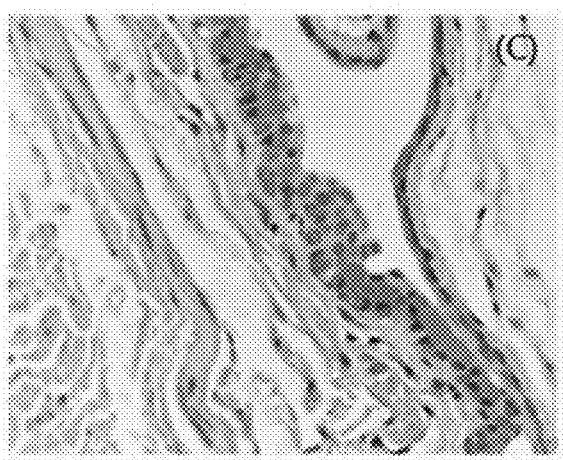
Figure 19D:
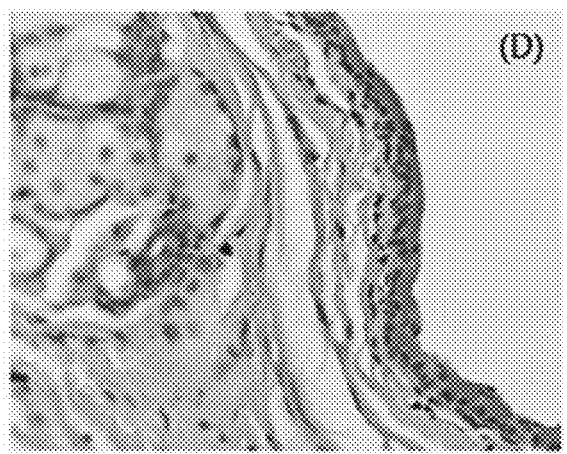
Figure 19E:
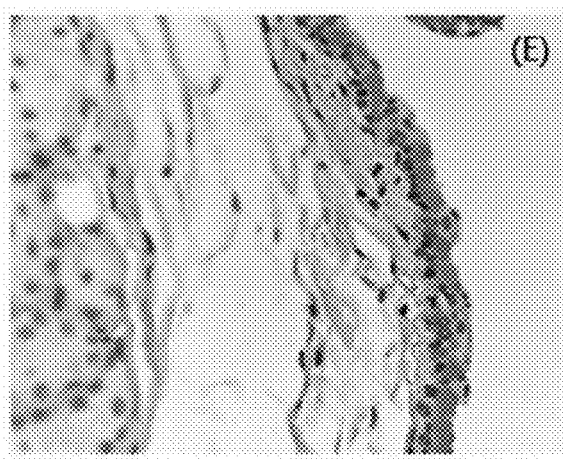
Figure 19F:
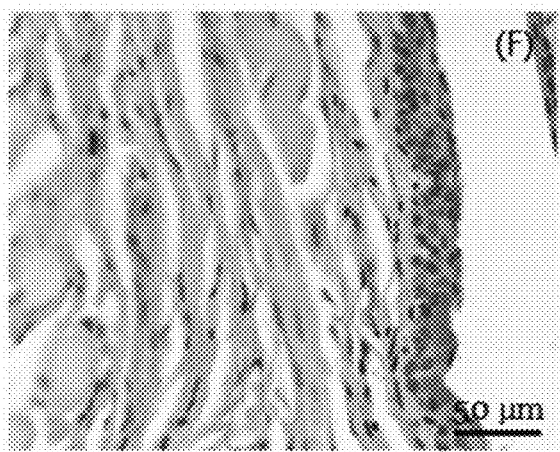
Figure 19G:
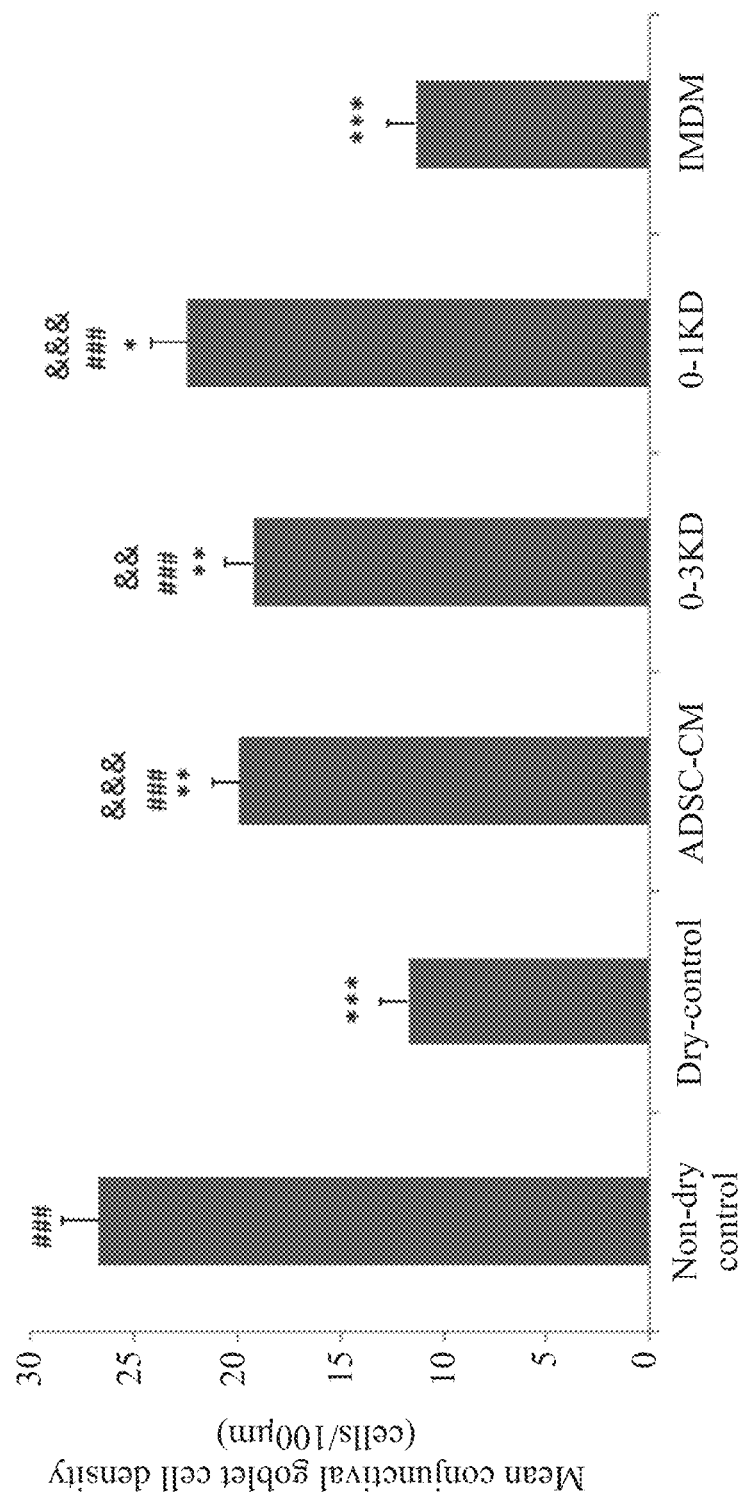
FIG. 19G shows the statistical comparison of the conjunctival goblet cell density between different groups of CEC induced dry eyes. * compared with non-dry control, *p<0.05, p<0.01, *p<0.001. #compared with dry control, #p<0.05, ##p<0.01, ###p<0.001. & compared with IMDM, & p<0.05, && p<0.01, &&& p<0.001.
Figure 20A:
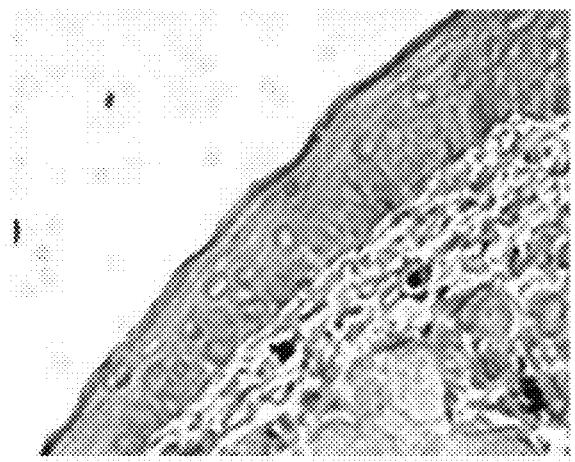
FIGS. 20A to 20E show the result of immunohistochemical analysis for MUC16 expression in mouse conjunctival epithelium.
Figure 20B:
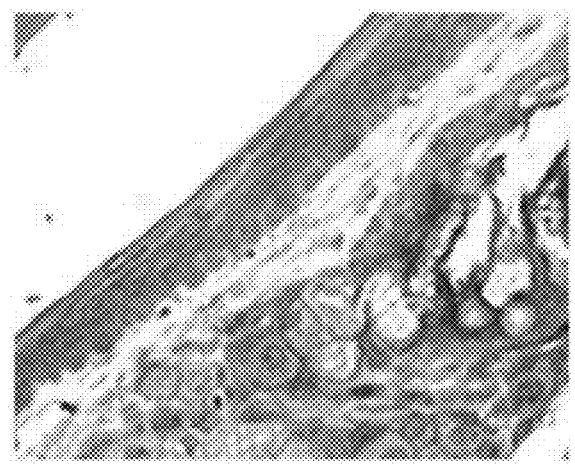
Figure 20C:
Figure 20D:
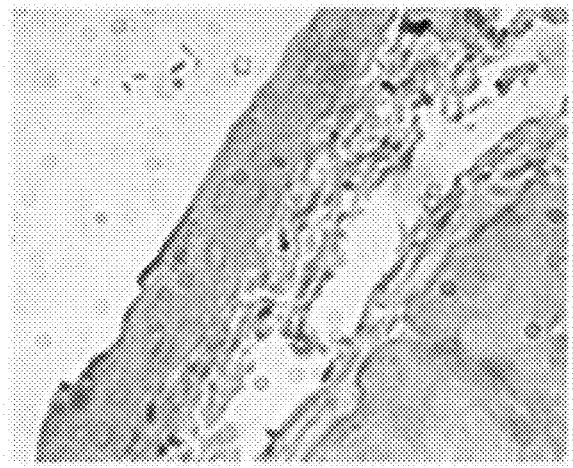
Figure 20E:
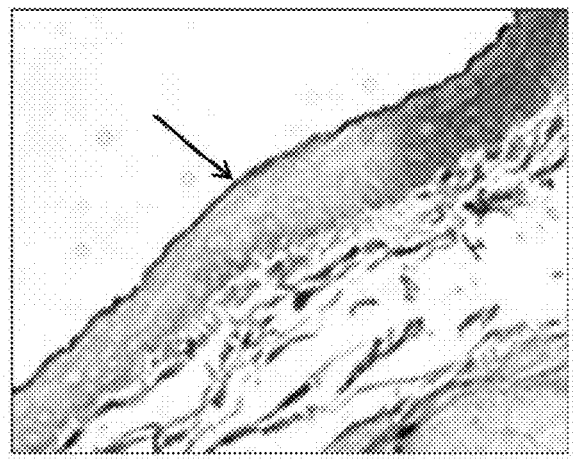

FIGS. 13A-13C showed the result of tear secretion assays conducted with different ADSC-CM fractions having 30-100 kDa, 0-30 kDa, >10 kDa, <10 kDa, >3 kDa, <3 kDa, 0-3 kDa and 0-1 kDa. The results showed that ADSC-CM fractions having 0-30 kDa, <10 kDa, <3 kDa, 0-3 kDa and 0-1 kDa were able to stimulate the treated mice in the dry chamber to secret tear volume as much as or even greater than that of the non-dry control.

Further, FIGS. 14A-14B, FIGS. 15A-15B, and FIGS. 16A-16B showed the immunofluorescence double staining results of the ADSC-CM fractions having 30-100 kDa, 0-30 kDa (FIGS. 14A-14B), >10 kDa, <10 kDa, >3 kDa, <3 kDa, (FIGS. 15A-15B), 0-3 kDa and 0-1 kDa (FIGS. 16A-16B), respectively, to analyze the effects of different eye drops on the expression of corneal epithelium-specific protein K12 and integrity of tight junction barrier by the expression of ZO-1 and occludin. From the results, expression of corneal epithelium-specific protein K12 was not altered with different eye drop treatment, while decreased expression levels of the tight junction-related proteins ZO-1 and occludin in mouse corneal epithelium were observed in dry-treated mice, but can be successfully prevented by ADSC-CM, and ADSC-CM fractions having 0-30 kDa, <10 kDa, <3 kDa, 0-3 kDa and 0-1 kDa.

Histological analysis was carried out as described above to compare the effects of the different ADSC-CM size fractions on the corneal epithelial morphology, the thickness of epithelium and stromal at the central cornea, and the mean conjunctival goblet cell densities. As shown in FIGS. 17A-17F, ADSC-CM and the ADSC-CM fraction having 0-30 kDa reversed the reduction of conjunctival goblet cells observed in the CEC-induced dry eyes, while the ADSC-CM fraction having 30-100 kDa failed to show the same effect.

In FIGS. 18A to 18H, ADSC-CM and the ADSC-CM fractions having <10 kDa and <3 kDa reversed the reduction of conjunctival goblet cells observed in the CEC-induced dry eyes, while the ADSC-CM fractions having >10 kDa and >3 kDa failed to show the same effect. In FIGS. 19A-19G, ADSC-CM and the ADSC-CM fractions having 0-3 kDa and 0-1 kDa reversed the reduction of conjunctival goblet cells observed in the CEC-induced dry eyes, while IMDM treatment failed to show the same effect.

In addition, IHC assays were conducted to examine the expression of MUC4 and MUC16 in mice treated with different ADSC-CM size fractions. FIGS. 20A-20E showed the results of MUC 16 expression in mice housed in CEC treated with ADSC-CM and different ADSC-CM fractions. It is shown that ADSC-CM (FIG. 20C) and the ADSC-CM fraction having 0-30 kDa (FIG. 20D) induced the MUC 16 expression that was observed to be suppressed in the CEC-induced dry eye, while the ADSC-CM fraction having 30-100 kDa (FIG. 20E) failed to show the same effect. The arrow in FIG. 20E indicates the conjunctival epithelium cells.

Figure 21A:
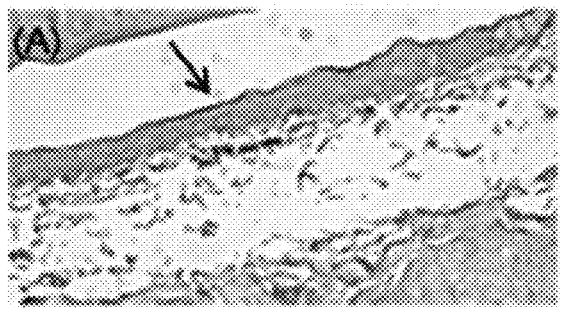
FIGS. 21A to 21G show the results of immunohistochemical analysis for MUC16 expression in mouse conjunctival epithelium.
Figure 21B:
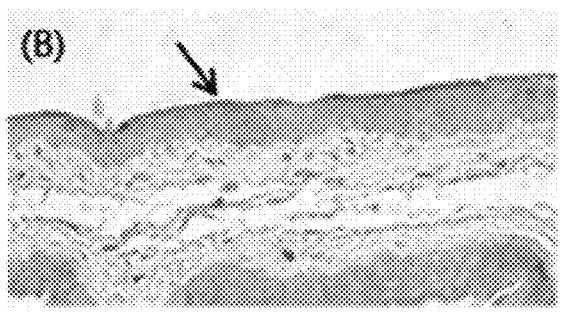
Figure 21C:
Figure 21D:
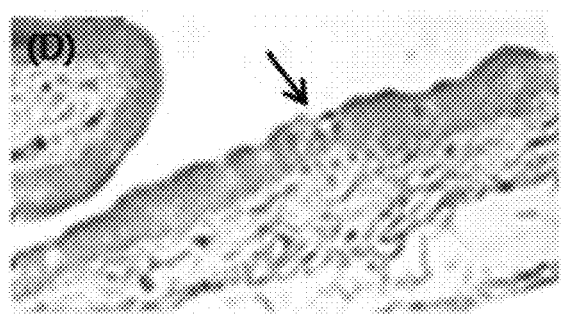
Figure 21E:
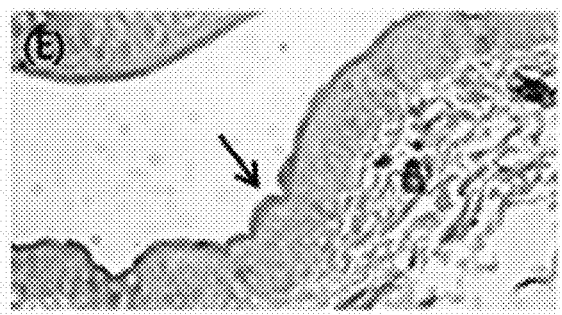
Figure 21F:
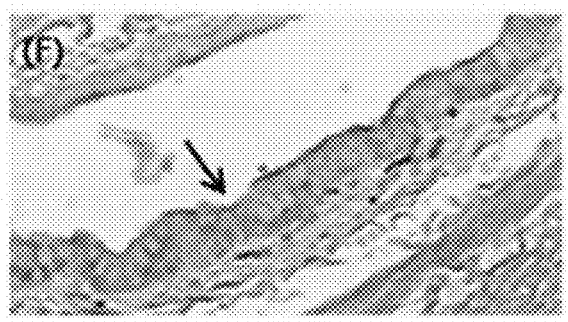
Figure 21G:
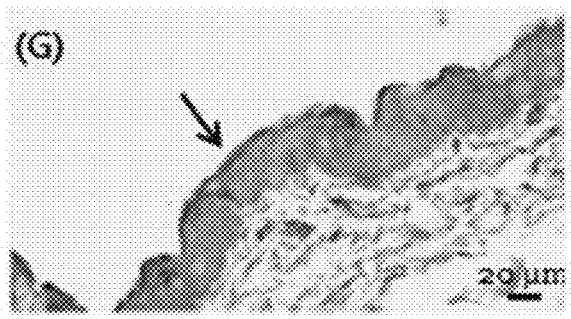
Figure 22A:
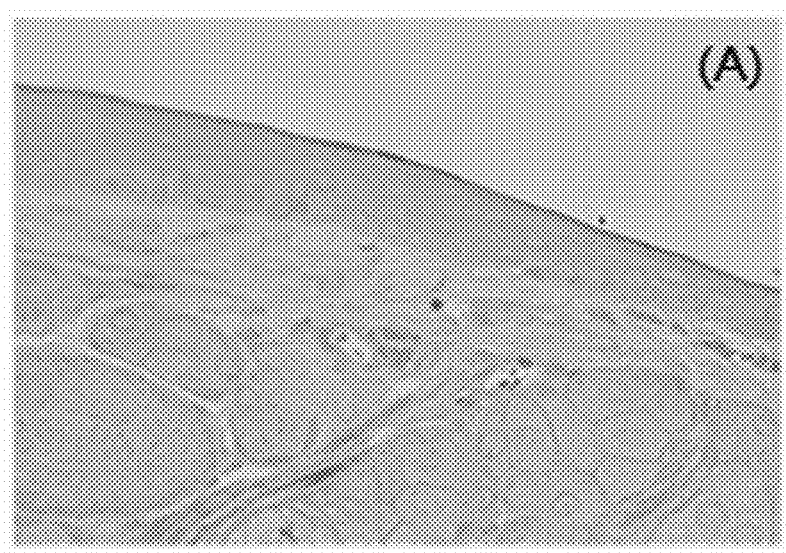
FIGS. 22A to 22F show the results of immunohistochemical analysis for MUC16 expression in mouse conjunctival epithelium.
Figure 22B:
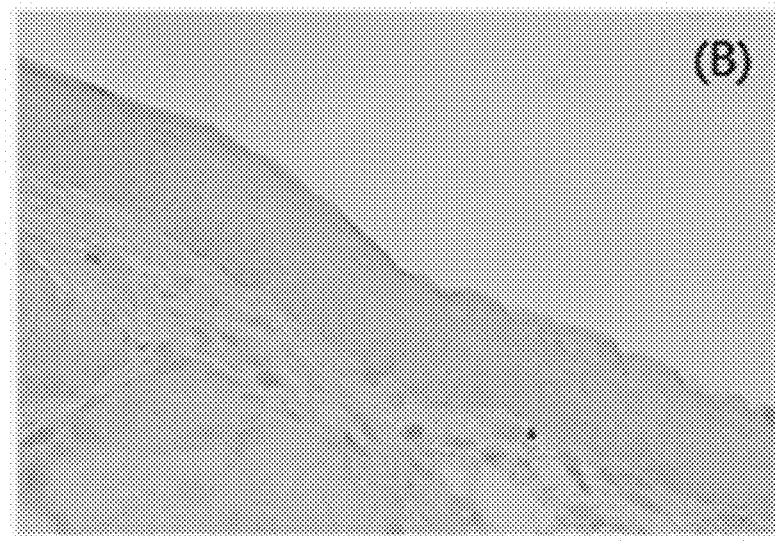
Figure 22C:
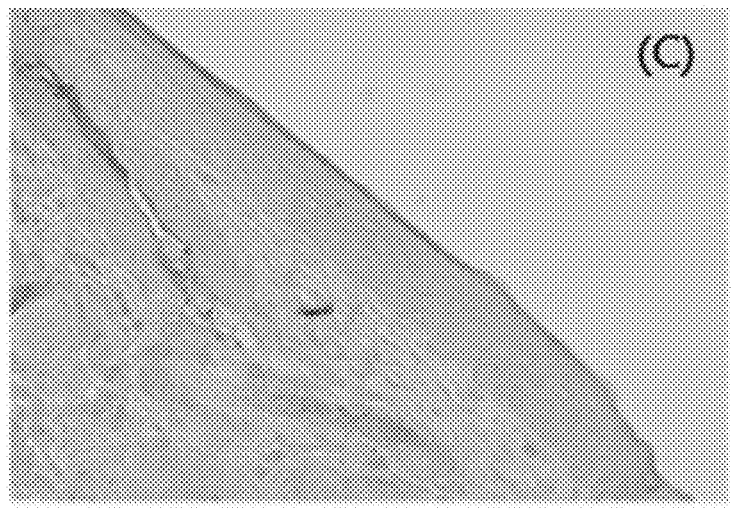
Figure 22D:
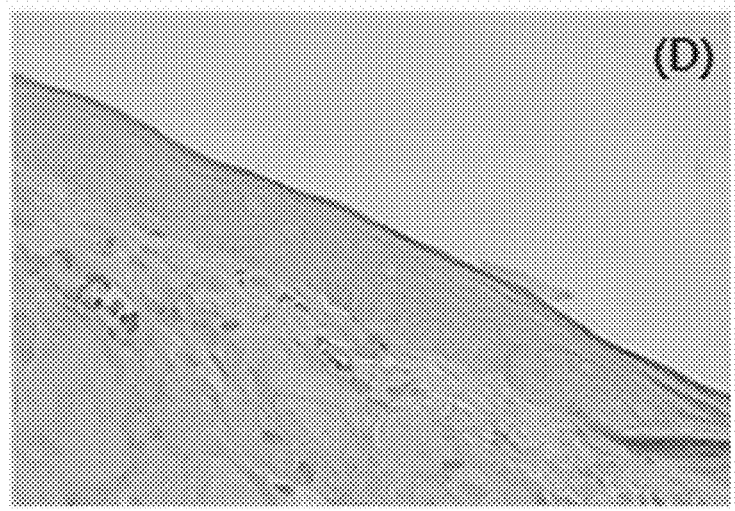
Figure 22E:
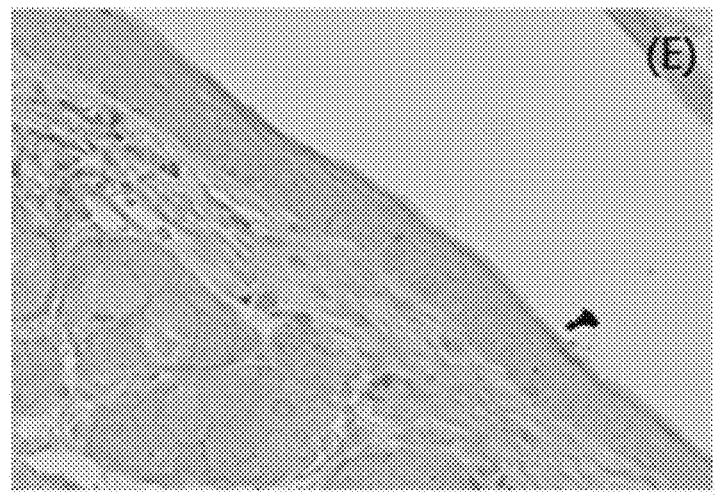
Figure 22F:
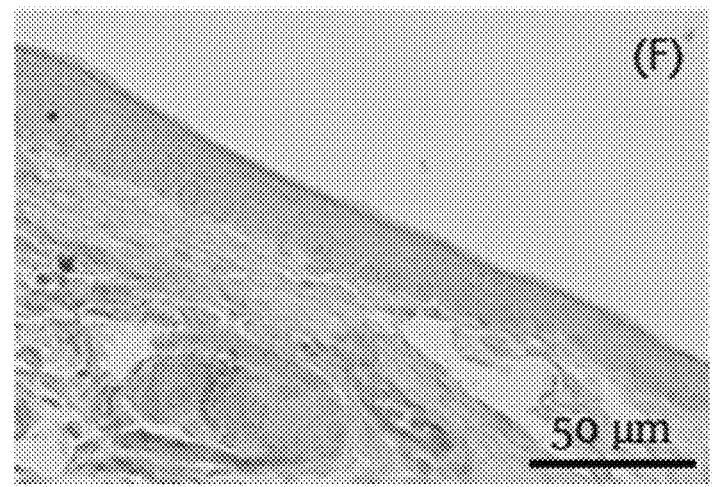

FIGS. 21A-21G showed the result of MUC16 expression in mice housed in CEC treated with ADSC-CM and different ADSC-CM fractions. Dry eyes treated with ADSC-CM (FIG. 21C) and the ADSC-CM fractions having <10 kDa (FIG. 21D) and <3 kDa (FIG. 21E) have more MUC16 expression than the ADSC-CM fraction having >10 kDa (FIG. 21F) and >3 kDa (FIG. 21G).

FIGS. 22A-22F showed the results of MUC16 expression in mice housed in CEC treated with ADSC-CM and the ADSC-CM fractions having 0-3 kDa and 0-1 kDa. Dry eyes treated with ADSC-CM (FIG. 22C) and the ADSC-CM fractions having 0-3 kDa (FIG. 22D) and 0-1 kDa (FIG. 22E) have similar MUC 16 expression to the non-dry control and those treated with ADSC-CM, while those treated with IMDM (FIG. 22F) have less MUC16 expression similar to the dry control.

Figure 23A:
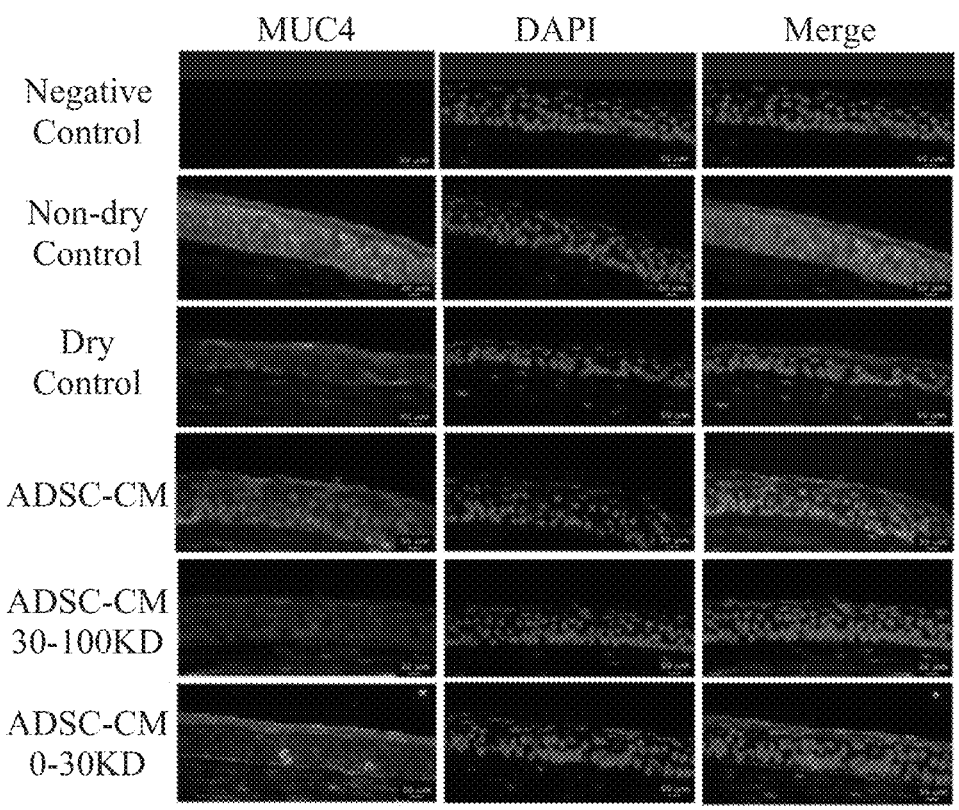
FIG. 23A shows immunohistochemical analysis for MUC4 in mouse corneal epithelium treated with the ADSC-CM fractions having 0-30 kDa or 30-100 kDa. Magnification: 400×. Scale bars: 20 µm, 3 µm sections.
Figure 23B:
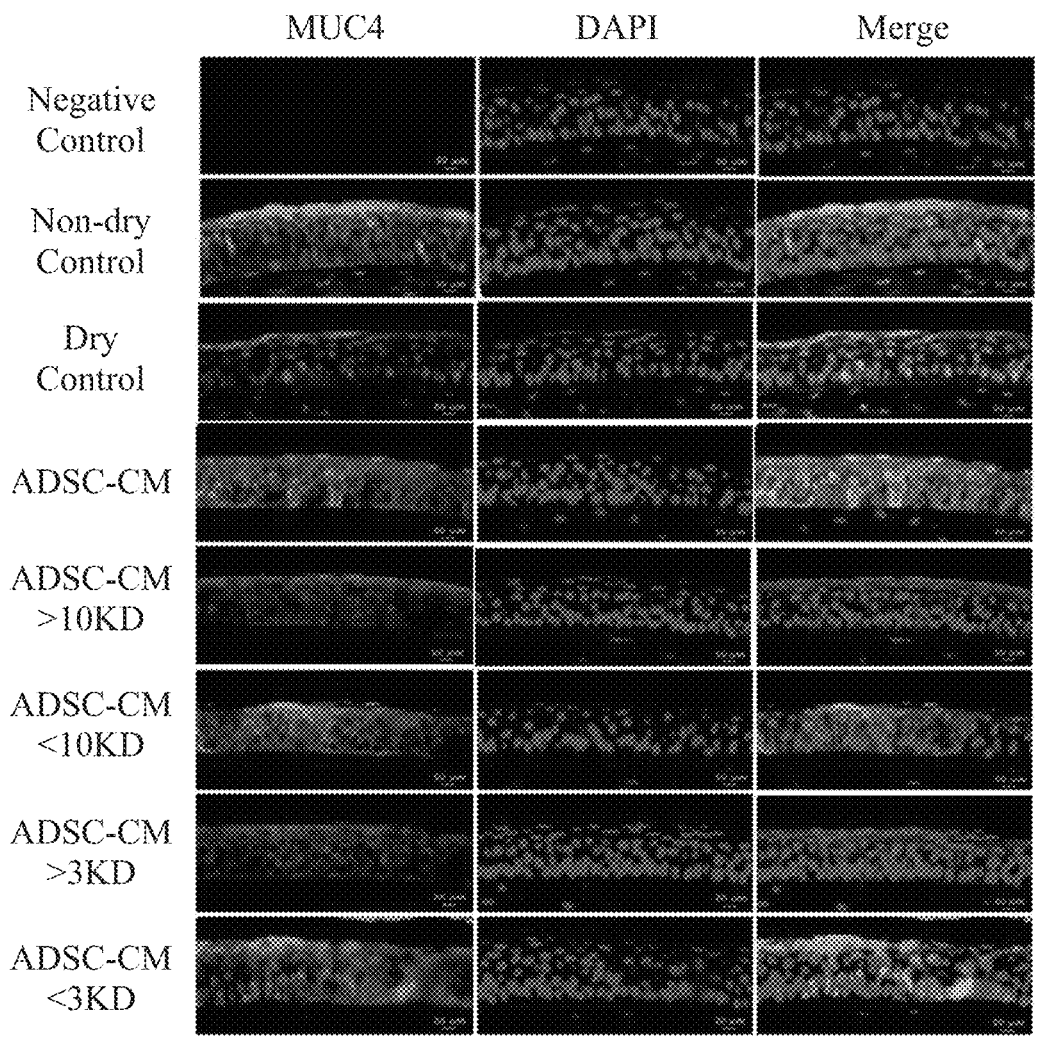
FIG. 23B shows immunohistochemical analysis for MUC4 in mouse corneal epithelium treated with the ADSC-CM fractions having >10 kDa, <10 kDa, >3 kDa or <3 kDa. Magnification: 400×. Scale bars: 20 µm, 3 µm sections.

Similarly, MUC4 expression levels were also examined in the animal model housed in CEC and treated with different ADSC-CM fractions. FIG. 23A showed the results of MUC4 expression levels of ADSC-CM and the ADSC-CM fractions having 30-100 kDa and 0-30 kDa, while FIG. 23B showed the results of MUC4 expression levels of ADSC-CM and the ADSC-CM fractions having >10 kDa, <10 kDa, >3 kDa, and <3 kDa. It was shown that the ADSC-CM fractions having 0-30 kDa, <10 kDa and <3 kDa showed the similar expression level of MUC4 in non-dry control and that treated with ADSC-CM, while reduction of MUC4 was observed in dry control and the ADSC-CM fractions having >10 kDa and >3 kDa.

Figure 24:
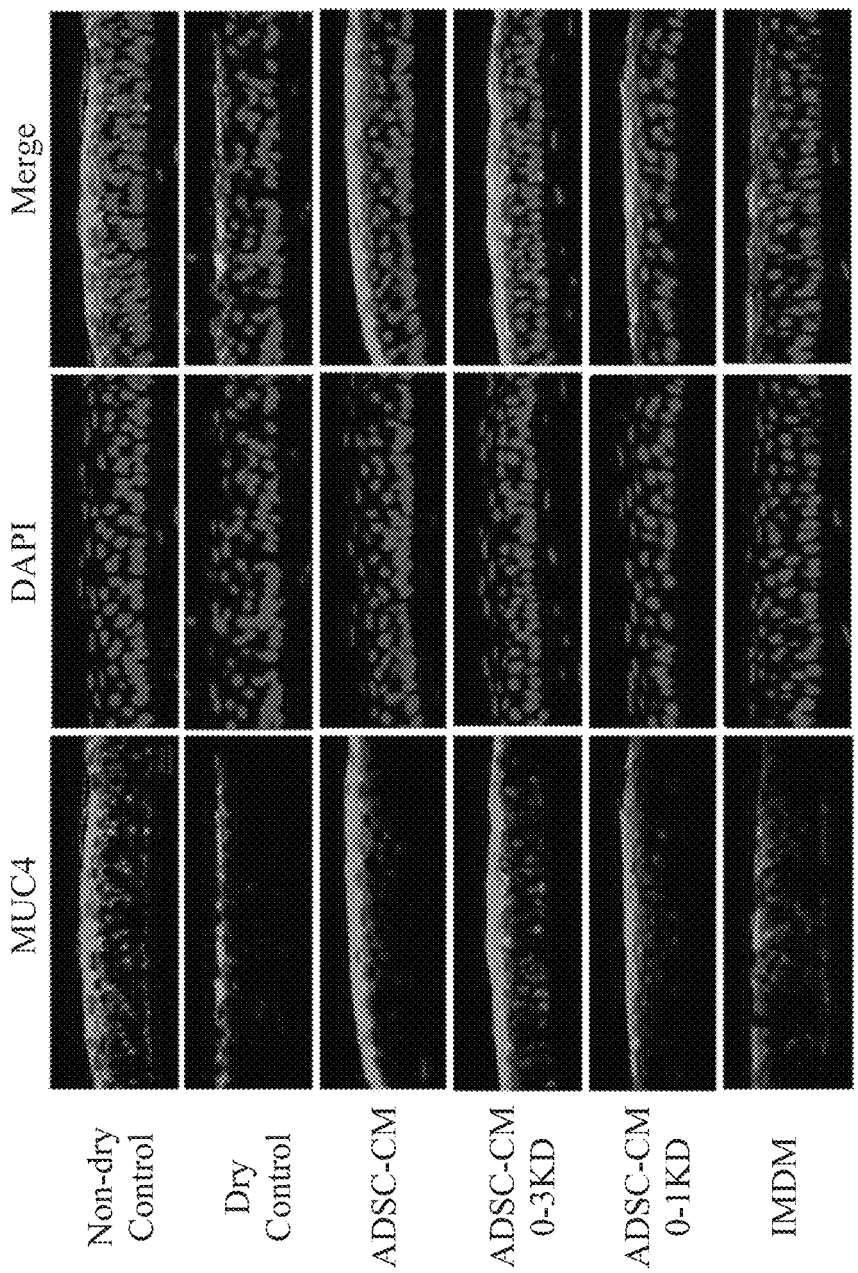
FIG. 24 shows immunohistochemical analysis for MUC4 in mouse corneal epithelium treated with the ADSC-CM fractions having 0-3 kDa or 0-1 kDa. Magnification: 400×. Scale bars: 20 µm, 3 µm sections.

FIG. 24 showed the results of MUC4 expression levels of ADSC-CM and the ADSC-CM fractions having 0-3 kDa and 0-1 kDa. Both ADSC-CM fractions having 0-3 kDa and 0-1 kDa showed similar MUC4 expression levels to that in non-dry control and that treated with ADSC-CM, while mice treated with IMDM showed reduction of the MUC4 expression level similar to that observed in the dry control.

Figure 25A:
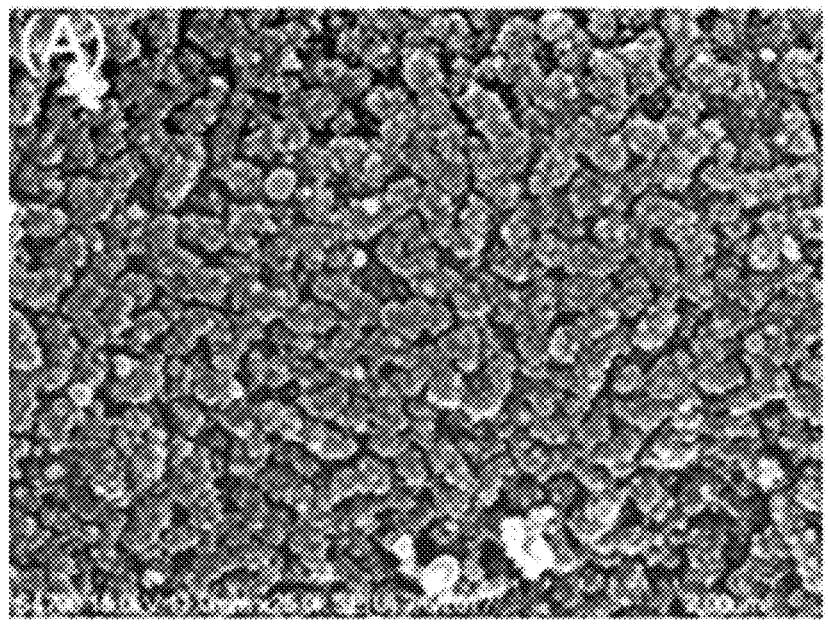
FIGS. 25A to 25E show the results of scanning electron microscopy of corneas from BALB/c mice housed in CEC treated with different eye drops.
Figure 25B:
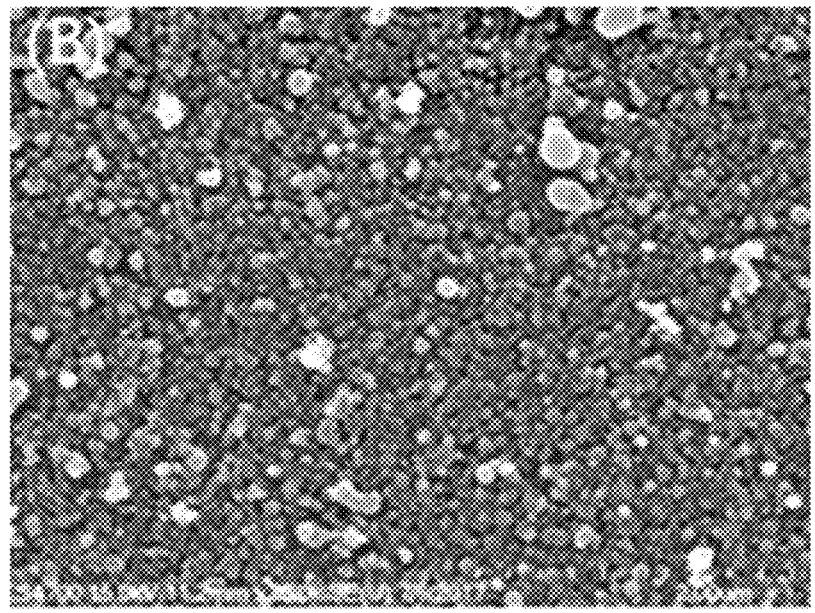
Figure 25C:
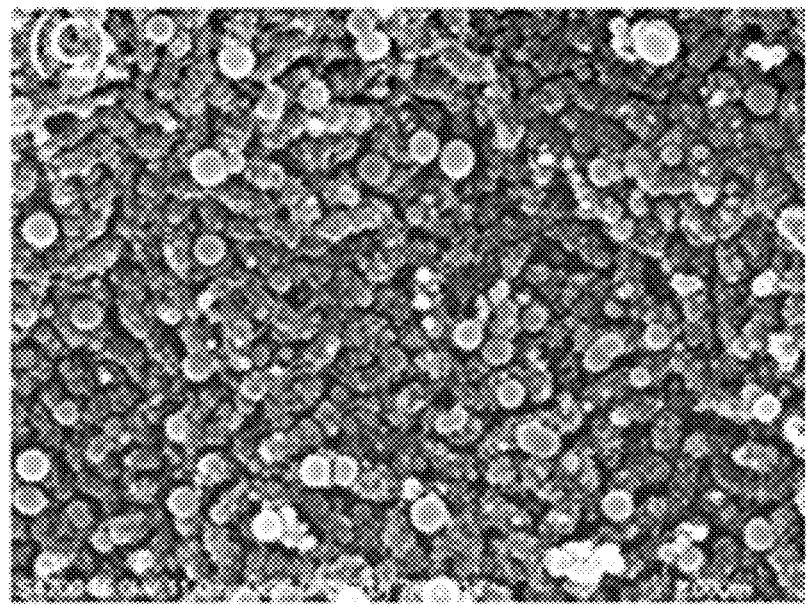
Figure 25D:
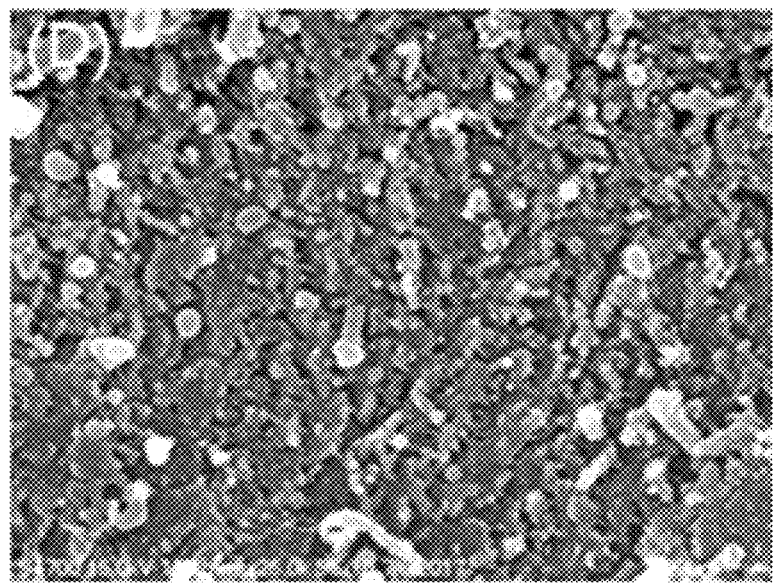
Figure 25E:
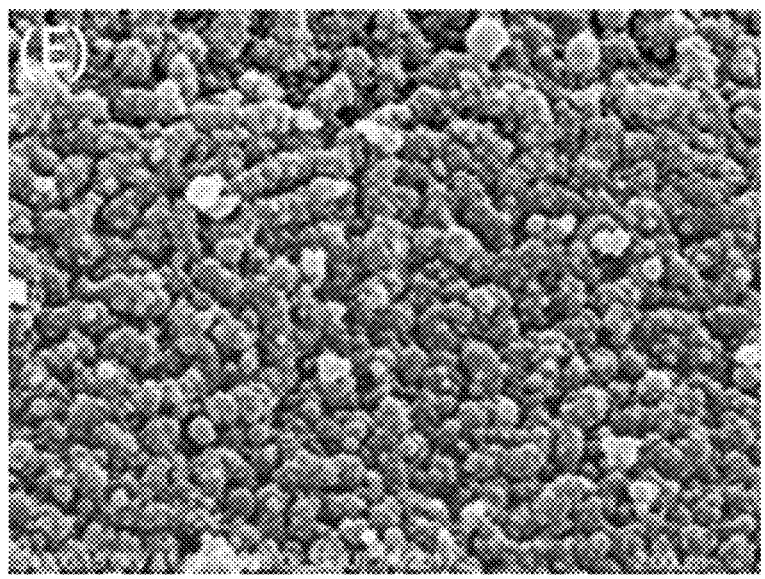

In addition, SEM study was carried out as described above with mice housed in CEC and treated with different ADSC-CM fractions. As shown in FIGS. 25A to 25E, microvilli of corneal epithelium were degenerated and lost in the CEC-induced dry eye mice (FIG. 25B). Topical application of the ADSC-CM fraction having <30 kDa (FIG. 25E) preserved the microvilli of corneal epithelium and had the similar effect to that applied with ADSC-CM (FIG. 25C) and in non-dry control. However, the ADSC-CM fraction having 30-100 kDa (FIG. 25D) did not show the same effect.

Figure 26A:
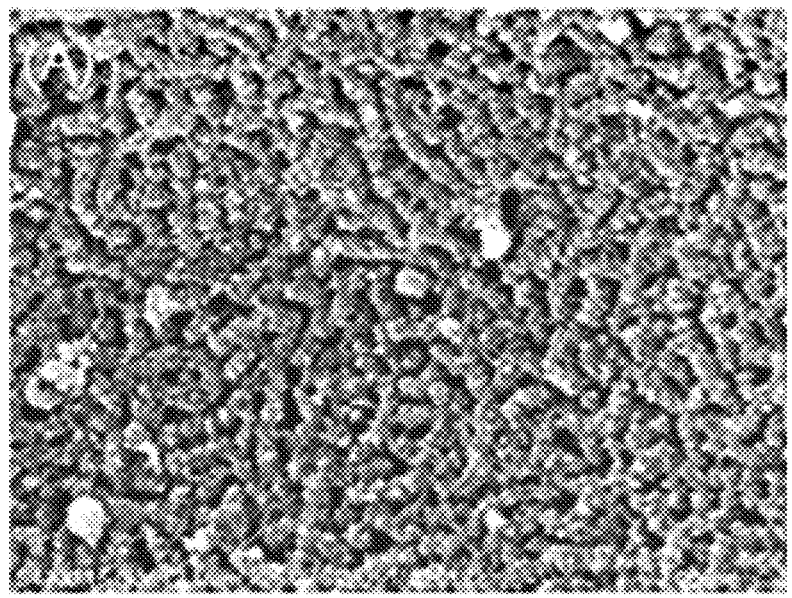
FIGS. 26A to 26G show the results of scanning electron microscopy of corneas from BALB/c mice housed in CEC treated with different eye drops.
Figure 26B:
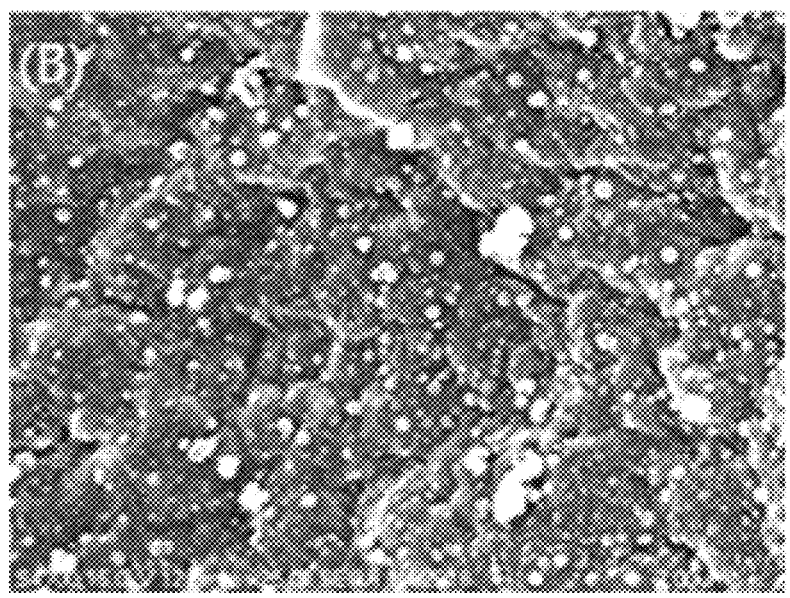
Figure 26C:
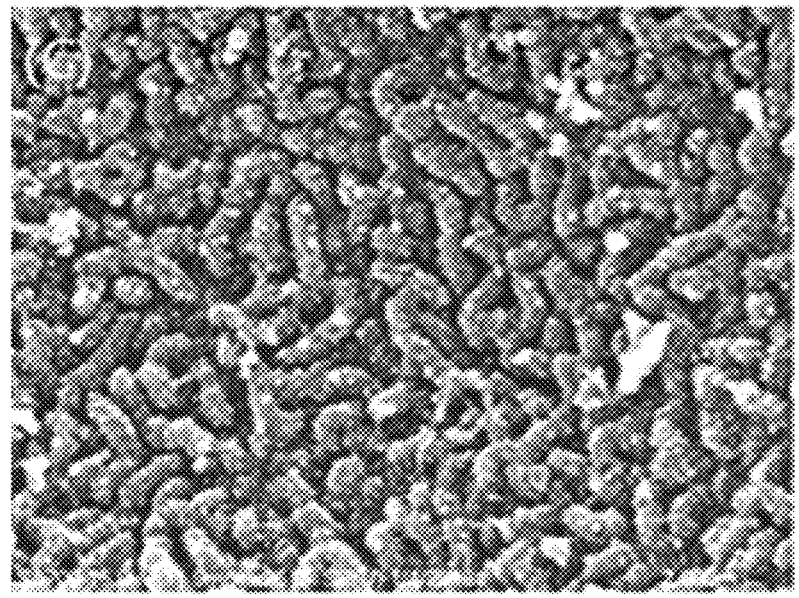
Figure 26D:
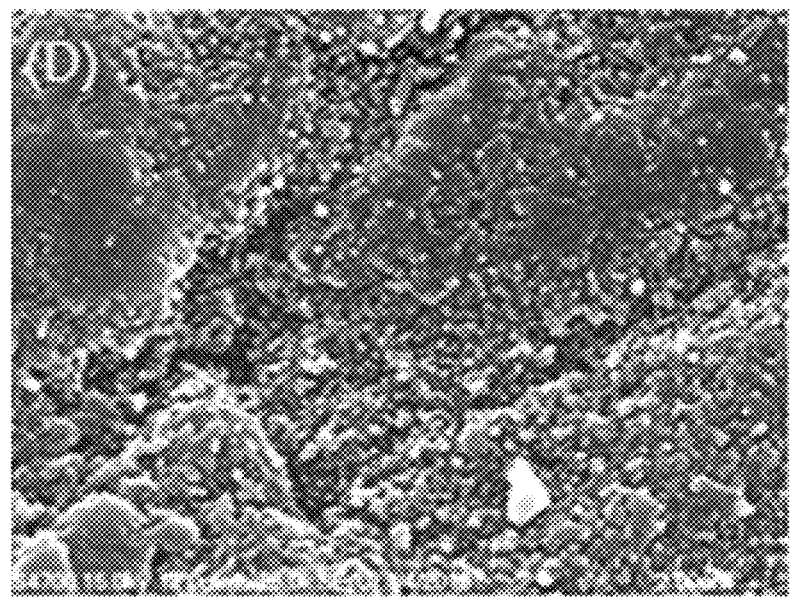
Figure 26E:
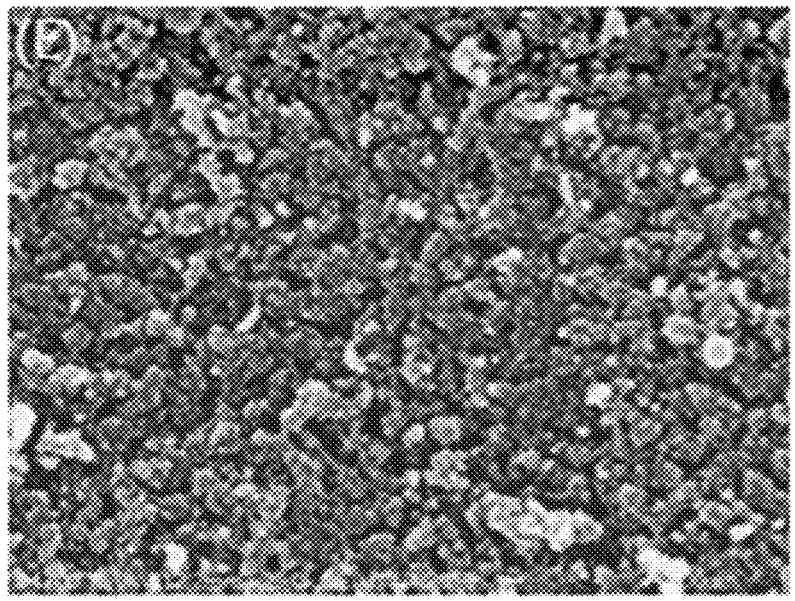
Figure 26F:
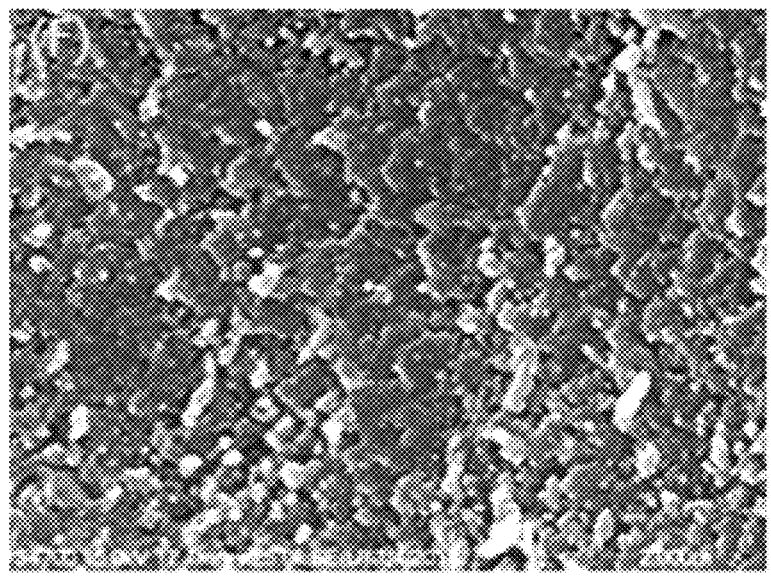
Figure 26G:
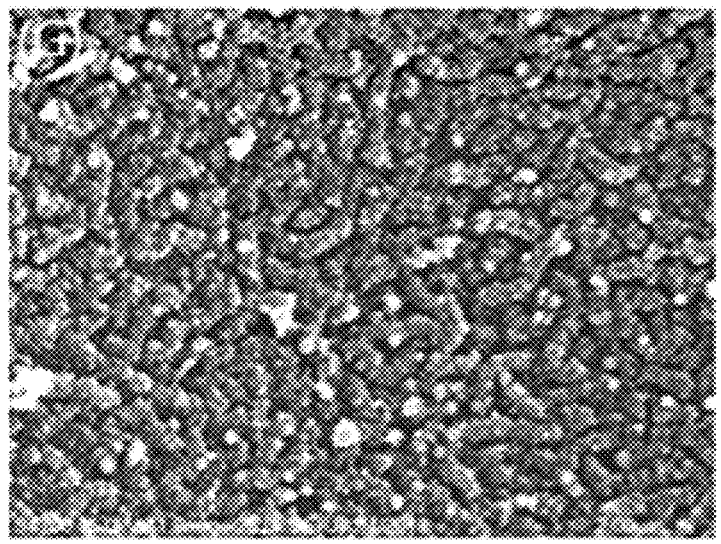

Similarly, FIGS. 26A to 26G showed the results of SEM with ADSC-CM fractions having >10 kDa, <10 kDa, >3 kDa and <3 kDa. Topical application of ADSC-CM fractions having <10 kDa (FIG. 26E) and <3 kDa (FIG. 26G) preserved the microvilli of corneal epithelium and had the similar effect to that applied with ADSC-CM (FIG. 26C) and in non-dry control (FIG. 26A). However, dry eyes treated ADSC-CM fractions having >10 kDa (FIG. 26D) and >3 kDa (FIG. 26F) were not able to preserve the microvilli of corneal epithelium induced in dry eyes.

Figure 27A:
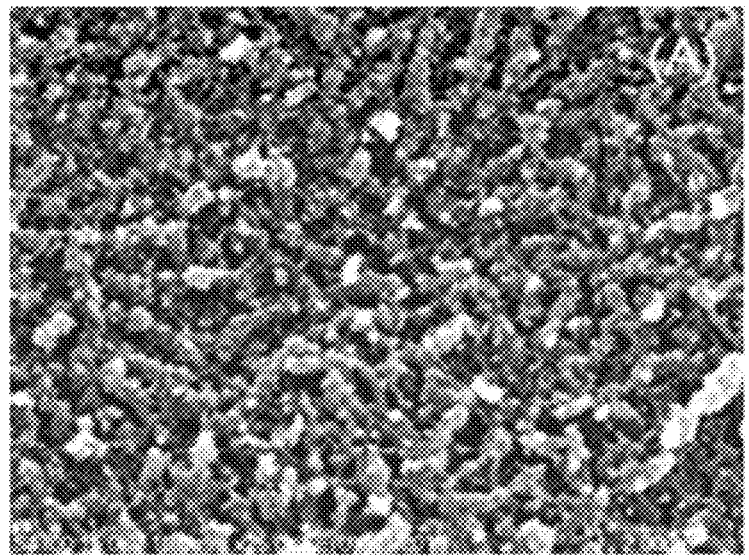
FIGS. 27A to 27F show the results of scanning electron microscopy of corneas from BALB/c mice housed in CEC treated with different eye drops.
Figure 27B:
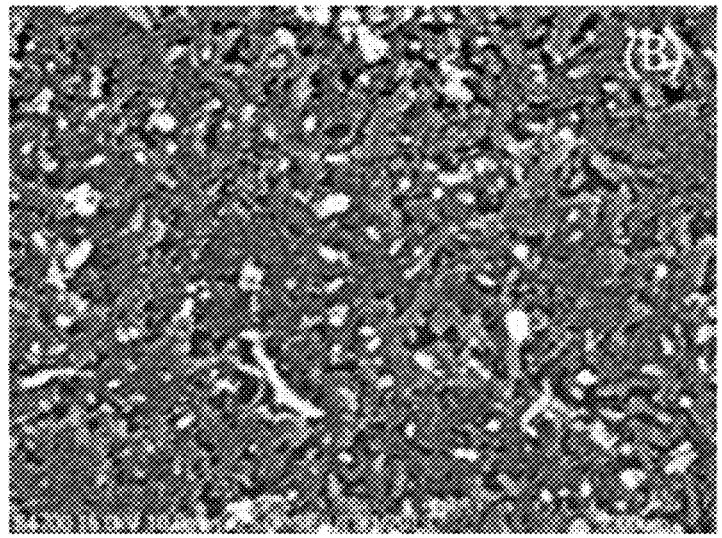
Figure 27C:
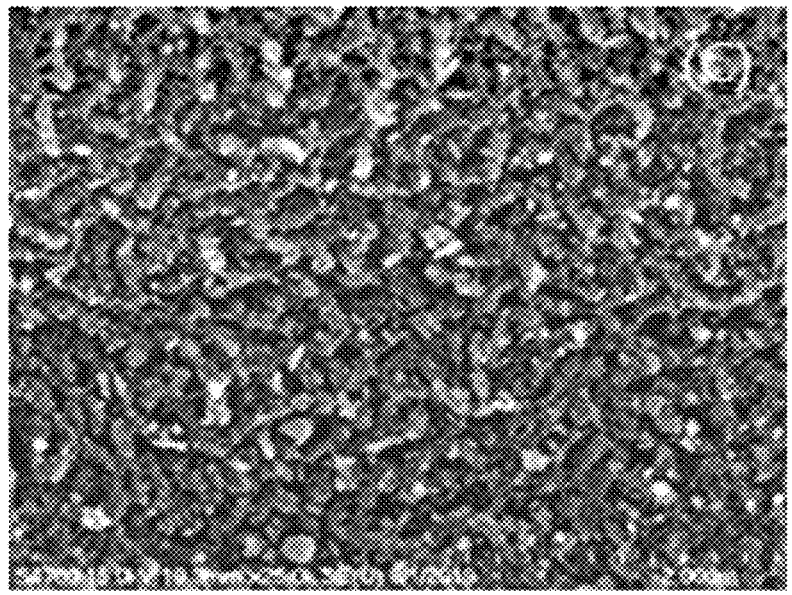
Figure 27D:
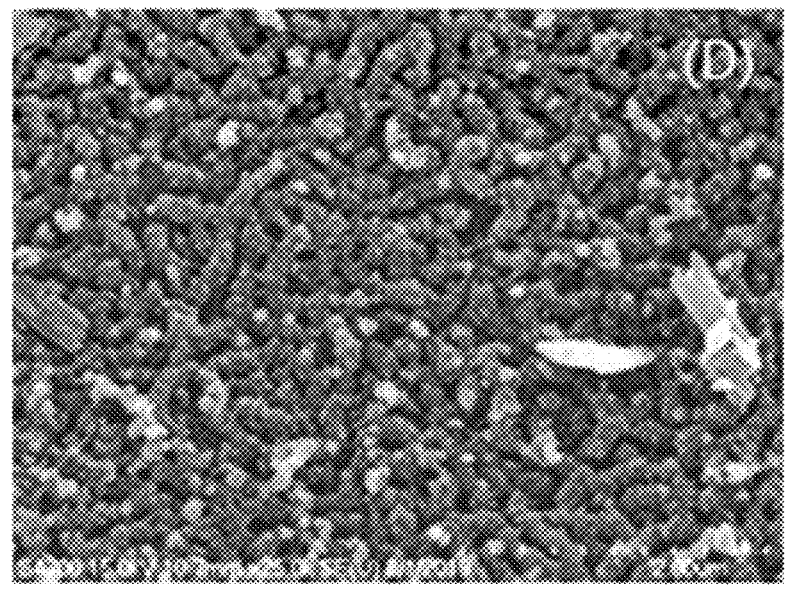
Figure 27E:
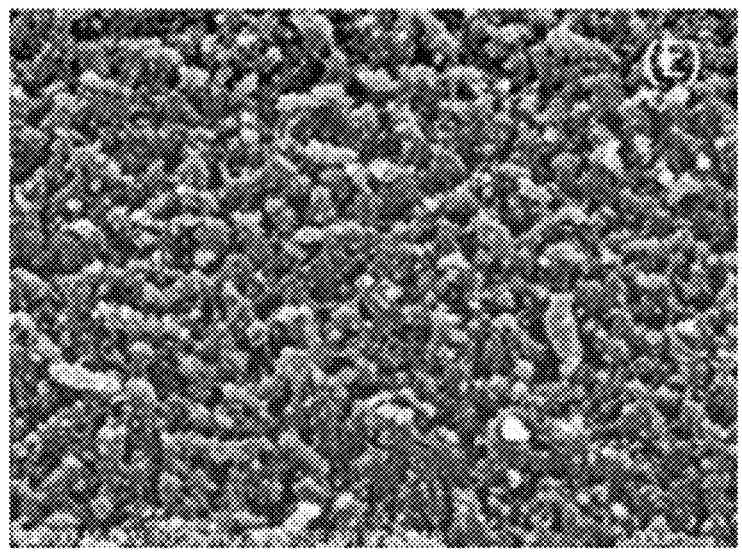
Figure 27F:
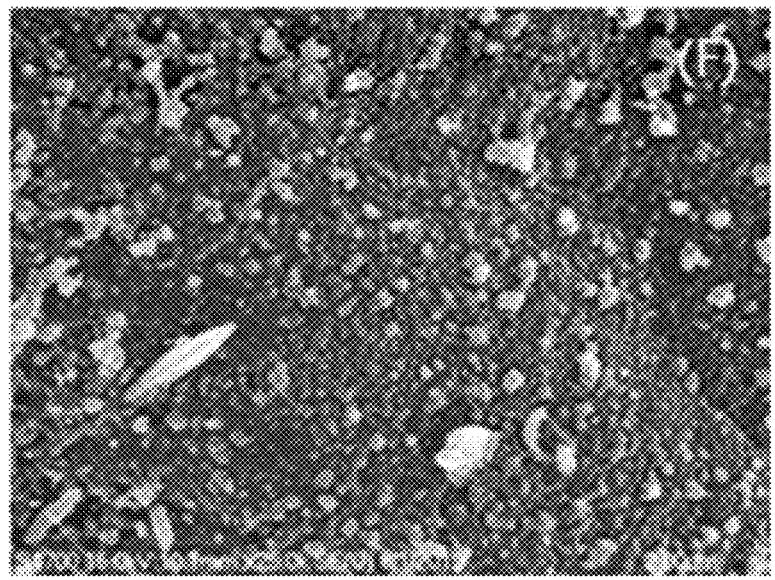

Further, FIGS. 27A to 27F showed the SEM results of dry eyes treated with ADSC-CM fractions having 0-3 kDa and 0-1 kDa. Both ADSC-CM fractions having 0-3 kDa (FIG. 27D) and 0-1 kDa (FIG. 27E) showed similar preservation of microvilli of corneal epithelium as observed in non-dry control (FIG. 27A) and that treated with ADSC-CM (FIG. 27C), while mice treated with IMDM (FIG. 27F) showed loss and degeneration of microvilli of corneal epithelium similar to that observed in the dry control (FIG. 27B).

From the above Examples 1 to 4, it clearly showed that ADSC-CM comprising the active ingredients having the molecular weight of less than 30 kDa, less than 3 kDa, or less than 1 kDa efficiently treated dry eyes in a subject.

In the in vitro HCECs desiccation stress study, desiccation for ten minutes caused decreased viability of HCECs, which was not alleviated by Refresh, IMDM, or IMMCA, but was significantly rescued by ADSC-CM and the ADSC-CM fractions having active ingredients with the molecular weight of less than 30 kDa, less than 3 kDa, or less than 1 kDa. The concomitant western blot analysis also revealed increased expression of P38 and p-Erk1/2 of HCECs cultured in ADSC-CM.

Mice in the dry CEC had more evaporation and hence more corneal fluorescein staining and rose bengal staining. The staining was lightest in the ADSC-CM group. The immunohistochemical study of the corneas also revealed that the mice in the CEC had significantly decreased expression of ZO-1 and occludin, which are markers of tight junction. The decreased expressions of ZO-1 and occludin from dry injury were almost reversed or even better by application of ADSC-CM and its fractions having less than 30 kDa, less than 3 kDa, or less than 1 kDa. The corneal epithelium in the ADSC-CM group also showed the best expression of K12, which meant preserving the characteristics of corneal epithelium. The beneficial effect of ADSC-CM and its fractions on the tight junction of the corneas was not only revealed by confocal immunohistochemical study, but was also demonstrated in the TEM study. The preservation of tight junction by ADSC-CM might help the corneal epithelium carry out housekeeping functions that borders the external environment, including provision of a barrier to fluid loss, toxin irritation and pathogen entrance.

ADSC-CM and its fractions not only protected the tight junction of corneal epithelial cells, but also protected the conjunctival goblet cells and membrane-associated mucin MUC16 expression. Conjunctival goblet cell density was significantly decreased in the CEC mice, which was alleviated by Refresh, IMMCA or ADSC-CM. ADSC-CM and its fractions increased the goblet cell density best to a level higher than that of non-dry mice. The MUC16 expression was continuous in the non-dry control group and interrupted in the dry control group. ADSC-CM and its fractions helped preserve the integrity of MUC16 expression.

Dry injury caused loss of the microvilli of the corneal epithelium. While lubrication by Refresh or IMMCA alleviated the loss of microvilli caused by dry stress, ADSC-CM and its fractions preserved the microvilli best.

In conclusion, the disclosure demonstrated the effects of ADSC-CM on dry-induced ocular surface injury, probably through activation of Erk1/2 and P38.

The present disclosure has been described using exemplary embodiments. However, it should be understood that the scope of the disclosure is not limited to the disclosed embodiments. On the contrary, it is intended to cover various modifications and similar rearrangement. The scope of the claims therefore should be accorded the broadest interpretation so as to encompass all such modifications and similar arrangements.

REFERENCES

1. The definition and classification of dry eye disease: report of the Definition and Classification Subcommittee of the International Dry Eye WorkShop (2007). Ocul. Surf. 2007; 5(2):75-92.
2. Coursey T G, de Paiva C S. Managing Sjogren's Syndrome and non-Sjogren Syndrome dry eye with anti-inflammatory therapy. Clinical ophthalmology. 2014; 8:1447-58.
3. Pan Q, Angelina A, Marrone M, Stark W J, Akpek E K. Autologous serum eye drops for dry eye. Cochrane Database Syst. Rev. 2017; 2:CD009327.
4. Chen L, Tredget E E, Wu P Y, Wu Y. Paracrine factors of mesenchymal stem cells recruit macrophages and endothelial lineage cells and enhance wound healing. PLoS One. 2008; 3(4):e1886.
5. Osugi M, Katagiri W, Yoshimi R, Inukai T, Hibi H, Ueda M. Conditioned media from mesenchymal stem cells enhanced bone regeneration in rat calvarial bone defects. Tissue Eng. Part A. 2012; 18(13-14):1479-89.
6. Kwon S H, Bhang S H, Jang H K, Rhim T, Kim B S. Conditioned medium of adipose-derived stromal cell culture in three-dimensional bioreactors for enhanced wound healing. J. Surg. Res. 2015; 194(1):8-17.
7. Beyazyildiz E, Pinarli F A, Beyazyildiz O, Hekimoglu E R, Acar U, Demir M N, et al. Efficacy of topical mesenchymal stem cell therapy in the treatment of experimental dry eye syndrome model. Stem Cells Int. 2014; 2014:250230.
8. Pawitan J A. Prospect of stem cell conditioned medium in regenerative medicine. Biomed. Res. Int. 2014; 2014:965849.
9. Griesche N, Luttmann W, Luttmann A, Stammermann T, Geiger H, Baer P C. A simple modification of the separation method reduces heterogeneity of adipose-derived stem cells. Cells Tissues Organs. 2010; 192(2):106-15.
10. Sun L Y, Hsieh D K, Yu T C, Chiu H T, Lu S F, Luo G H, et al. Effect of pulsed electromagnetic field on the proliferation and differentiation potential of human bone marrow mesenchymal stem cells. Bioelectromagnetics. 2009; 30(4):251-60.
11. Sun L Y, Hsieh D K, Syu W S, Li Y S, Chiu H T, Chiou T W. Cell proliferation of human bone marrow mesenchymal stem cells on biodegradable microcarriers enhances in vitro differentiation potential. Cell Prolif 2010; 43(5):445-56.
12. Matsuo T. Trehalose protects corneal epithelial cells from death by drying. The British Journal of Ophthalmology. 2001; 85(5):610-2.
13. Higuchi A, Kawakita T, Tsubota K. IL-6 induction in desiccated corneal epithelium in vitro and in vivo. Mol. Vis. 2011; 17:2400-6.
14. Zheng X, Goto T, Shiraishi A, Ohashi Y. In vitro efficacy of ocular surface lubricants against dehydration. Cornea. 2013; 32(9):1260-4.
15. Barabino S, Shen L, Chen L, Rashid S, Rolando M, Dana M R. The controlled-environment chamber: a new mouse model of dry eye. Investigative Ophthalmology & Visual Science. 2005; 46(8):2766-71.
16. Pauly A, Brignole-Baudouin F, Labbe A, Liang H, Warnet J M, Baudouin C. New tools for the evaluation of toxic ocular surface changes in the rat. Investigative Ophthalmology & Visual Science. 2007; 48(12):5473-83.
17. van Bijsterveld O P. Diagnostic tests in the Sicca syndrome. Archives of Ophthalmology. 1969; 82(1):10-4.
18. Schaumberg D A, Sullivan D A, Buring J E, Dana M R. Prevalence of dry eye syndrome among US women. American Journal of Ophthalmology. 2003; 136(2):318-26.
19. Tsubota K, Kawashima M, Inaba T, Dogru M, Ogawa Y, Nakamura S, et al. The era of antiaging ophthalmology comes of age: antiaging approach for dry eye treatment. Ophthalmic Res. 2010; 44(3):146-54.
20. Tsubota K, Kawashima M, Inaba T, Dogru M, Matsumoto Y, Ishida R, et al. The antiaging approach for the treatment of dry eye. Cornea. 2012; 31 Suppl. 1:S3-8.
21. Harman D. Aging: a theory based on free radical and radiation chemistry. J. Gerontol. 1956; 11(3):298-300.
22. Yang D, Wang W, Li L, Peng Y, Chen P, Huang H, et al. The relative contribution of paracrine effect versus direct differentiation on adipose-derived stem cell transplantation mediated cardiac repair. PLoS One. 2013; 8(3):e59020.
23. Burlacu A, Grigorescu G, Rosca A M, Preda M B, Simionescu M. Factors secreted by mesenchymal stem cells and endothelial progenitor cells have complementary effects on angiogenesis in vitro. Stem Cells Dev. 2013; 22(4):643-53.
24. Bian S, Zhang L, Duan L, Wang X, Min Y, Yu H. Extracellular vesicles derived from human bone marrow mesenchymal stem cells promote angiogenesis in a rat myocardial infarction model. J. Mol. Med. (Berl). 2014; 92(4):387-97.
25. Lopez-Verrilli M A, Caviedes A, Cabrera A, Sandoval S, Wyneken U, Khoury M. Mesenchymal stem cell-derived exosomes from different sources selectively promote neuritic outgrowth. Neuroscience. 2016; 320:129-39.
26. Monsel A, Zhu Y G, Gudapati V, Lim H, Lee J W. Mesenchymal stem cell derived secretome and extra-

What is claimed is:

1. A method for preventing or treating environmentally-induced evaporative dry eye syndrome in a subject in need thereof, comprising administering to the eye of said subject a therapeutically effective amount of a formulation comprising a composition comprising a fraction with molecular weights less than 30 kDa prepared by:
   obtaining adipose-derived stem cells (ADSCs) from adipose tissue of the subject, wherein the subject is human;
   culturing the ADSCs in a medium supplemented with serum and mesenchymal stem cell culture adjuvant (MCA) for 2 to 5 passages,
   wherein the medium is selected from the group consisting of alpha minimum essential medium (alpha-MEM), Dulbecco's Modified Eagle's Medium (DMEM), Roswell Park Memorial Institute (RPM!) medium, improved minimum essential medium (IMEM), and Iscove's Modified Dulbecco's Medium (IMDM),
   wherein the serum is fetal bovine serum or human serum having a concentration in a range of from 5% to 15% in the medium,
   wherein the MCA comprises at least one of fibroblast growth factor 2 (FGF2), N-acetyl-L-cysteine (NAC) and L-ascorbic acid-2-phosphate (AsA2P);
   harvesting the medium from the culture of 2 to 5 ADSC passages;
   centrifuging the harvested medium followed by filtering; and
   obtaining the fraction with molecular weights less than 30 kDa from the filtered medium.

2. The method of claim 1, wherein the fibroblast growth factor 2 (FGF2) has a concentration in a range of from 5 ng/mL to 15 ng/mL in the mesenchymal stem cell culture adjuvant (MCA).

3. The method of claim 1, wherein the N-acetyl-L-cysteine (NAC) has a concentration in a range of from 1 mM to 5 mM in the mesenchymal stem cell culture adjuvant (MCA).

4. The method of claim 1, wherein the L-ascorbic acid-2-phosphate (AsA2P) has a concentration in a range of from 0.1 mM to 0.5 mM in the mesenchymal stem cell culture adjuvant (MCA).

5. The method of claim 1, wherein the fraction with molecular weights less than 30 kDa comprises a fraction with molecular weight less than 10 kDa.

6. The method of claim 5, wherein the fraction with molecular weights less than 10 kDa comprises a fraction with molecular weight less than 3 kDa.

7. The method of claim 6, wherein the fraction with molecular weights less than 3 kDa comprises a fraction with molecular weight less than 1 kDa.

8. A composition comprising the fraction with molecular weights less than 30 kDa according to claim 1.

* * * * *